United States Patent [19]
Himmelsbach et al.

[11] Patent Number: 5,821,240
[45] Date of Patent: Oct. 13, 1998

[54] PYRIMIDO[5,4]-DIPYRIMIDINES, PHARMACEUTICALS CONTAINING THEM, THEIR USE AND PROCESSES FOR THE PREPARATION THEREOF

[75] Inventors: Frank Himmelsbach, Mittelbiberach; Georg Dahmann, Ummendorf, both of Germany; Thomas von Rüden, Baden; Thomas Metz, Vienna, both of Austria

[73] Assignee: Dr. Karl Thomae GmbH, Biberach, Germany

[21] Appl. No.: 811,907

[22] Filed: Mar. 5, 1997

[30] Foreign Application Priority Data

Mar. 6, 1996 [DE] Germany ............ 196 08 588.8

[51] Int. Cl.$^6$ ............ C07D 487/04; A61K 31/505; A61K 31/535
[52] U.S. Cl. ............ 514/212; 514/218; 514/228.5; 514/234.2; 514/253; 514/254; 514/258; 540/575; 540/600; 544/61; 544/118; 544/256
[58] Field of Search ............ 544/256, 118, 544/61; 514/258, 234.2, 218, 254, 228.2, 212, 228.5; 540/575, 600

[56] References Cited

U.S. PATENT DOCUMENTS 5,707,989 1/1998 Himmelsbach et al. ............ 514/228.2

FOREIGN PATENT DOCUMENTS 44 31 867 3/1996 Germany.
WO 96/07657 3/1996 Germany.

OTHER PUBLICATIONS

Burke, Terrance, "Protein–Tyrosine Kinases: Potential Targets for Anticancer Drug Development," Stem Cells, (12), pp. 1–6, 1994.

*Primary Examiner*—Mukund J. Shah
*Assistant Examiner*—Ann M. Kessinger
*Attorney, Agent, or Firm*—Robert P. Raymond; Alan R. Stempel; Mary-Ellen Devlin

[57] ABSTRACT

Pyrimido[5,4-d]pyrimidines of the general formula

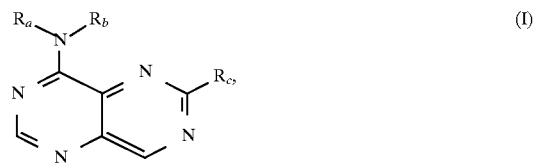

which have an inhibitory effect on signal transduction mediated by tyrosine kinases, their use for the treatment of disorders, in particular of oncoses, and their preparation. Exemplary compounds are:

4-[(3-Chloro-4-fluorophenyl)amino]-6-[1-methyl-4-piperidinylamino]pyrimido[5,4-d]pyrimidine, and 4-[(3-Chloro-4-fluorophenyl)amino]-6-[trans-4-dimethyl-aminocycohexylamino]pyrimido[5,4-d]pyrimidine.

6 Claims, No Drawings

PYRIMIDO[5,4]-DIPYRIMIDINES, PHARMACEUTICALS CONTAINING THEM, THEIR USE AND PROCESSES FOR THE PREPARATION THEREOF

The application PCT/EP95/03482, which is not a prior publication, has already described pyrimido[5,4-d]pyrimidines of the general formula

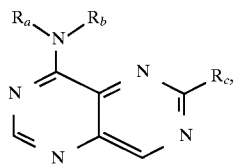

their tautomers, their stereoisomers and their salts, in particular their physiologically tolerated salts with inorganic or organic acids or bases, which have valuable pharmacological properties, in particular an inhibitory effect on signal transduction mediated by tyrosine kinases, their use for the treatment of disorders, in particular of oncoses, and their preparation.

It has now been found that other pyrimido[5,4-d]pyrimidines of the above general formula I have the same valuable pharmacological properties.

The present invention therefore relates to the novel pyrimido[5,4-d]pyrimidines of the above general formula I in which $R_a$ denotes a hydrogen atom, $R_b$ denotes a phenyl group which is substituted by the radicals $R_1$ to $R_3$, which can be identical or different, where $R_1$ represents a hydrogen, fluorine, chlorine or bromine atom, a trifluoromethoxy, methyl, hydroxymethyl, trifluoromethyl, ethynyl, nitro, cyano, phenoxy, phenyl, benzyloxy, benzyl, 1,1,2,2-tetrafluoroethoxy or methoxy group, $R_2$ represents a hydrogen atom, an amino, methylamino or dimethylamino group and $R_3$ represents a hydrogen, fluorine, chlorine or bromine atom;

or $R_a$ and $R_b$ denote, together with the nitrogen atom lying between them, a 1-indolinyl or 1,2,3,4-tetrahydroquinolin-1-yl group and $R_c$ denotes a cyclopentyloxy group in which the methylene group in position 3 is replaced by an oxygen atom or by an N-alkylimino group, a cyclohexyloxy group in which the methylene group in position 4 is replaced by an oxygen atom or by an N-alkylimino group, a 1-pyrrolidinyl group which is substituted in position 3 by an amino, alkylamino, dialkylamino or 4-hydroxyphenyl group and optionally additionally by a methyl group, a 1-piperidinyl group which can be substituted by an aminomethyl, alkylaminomethyl, dialkylaminomethyl, (1-pyrrolidinyl)methyl, (1-piperidinyl)methyl, (1-piperazinyl)methyl, (4-methyl-1-piperazinyl)methyl, morpholinomethyl, alkylcarbonylaminomethyl, alkylsulphonylaminomethyl, cyanomethyl, aminocarbonylmethyl, aminocarbonyl, (1-piperazinyl)carbonyl, (4-methyl-1-piperazinyl)carbonyl, 2-carboxyethyl, 2-alkoxycarbonylethyl, 2-(morpholinocarbonyl)ethyl, 2-aminoethyl, 2-aminocarbonylethyl, 2-alkylaminocarbonylethyl, 2-dialkylaminocarbonylethyl, 2-(1-pyrrolidinylcarbonyl)ethyl, carboxymethyloxy, alkoxycarbonylmethyloxy, aminocarbonylmethyloxy, alkylaminocarbonylmethyloxy, dialkylaminocarbonylmethyloxy, morpholinocarbonylmethyloxy, (1-pyrrolidinyl)carbonylmethyloxy, 4-piperidinyl or 1-methyl-4-piperidinyl group, a 1-piperidinyl group which is substituted in position 3 or 4 by an amino group and optionally additionally by one or two methyl groups or by one hydroxyl, alkoxy, formylamino, alkylamino, dialkylamino, morpholinocarbonylamino, alkoxycarbonylamino, alkylcarbonylamino, morpholino, 1-pyrrolidinyl, 1-piperidinyl, 1-piperazinyl, 4-methyl-1-piperazinyl, 4-dimethylamino-1-piperidinyl, 4-amino-1-piperidinyl, 2-oxo-1-pyrrolidinyl, 4-hydroxy-1-piperidinyl, 4-methylamino-1-piperidinyl, 3-oxo-1-piperazinyl, 4-methyl-3-oxo-1-piperazinyl, N-acetyl-N-methylamino, N-methyl-N-methylsulphonylamino, 2-oxo-1-imidazolidinyl or 3-methyl-2-oxo-1-imidazolidinyl group, a 1-azacycloheptyl group which is optionally substituted in position 3 or 4 by an amino, hydroxyl, alkoxy, alkylamino, dialkylamino, alkoxycarbonylamino or alkylcarbonylamino group, a morpholino group which is optionally substituted by 1 or 2 methyl groups, a 1-piperazinyl group which is substituted in position 4 by a 2-aminoethyl, 2-alkylaminoethyl, 2-dialkylaminoethyl, morpholinocarbonyl or by a phenyl group substituted by an alkoxy group, a 1-homopiperazinyl group which is optionally substituted in position 4 by an alkyl group, an 8-azabicyclo[3.2.1]-8-octyl group which is substituted in position 3 by an amino, alkylamino, dialkylamino, alkylcarbonylamino or alkoxycarbonylamino group or an ($R_4NR_5$) group in which $R_4$ represents a hydrogen atom or an alkyl group and $R_5$ represents a hydrogen atom, a methyl group which is substituted by a $C_{5-6}$-cycloalkyl group and in which the cycloalkyl moiety is substituted in position 3 or 4 by an amino, aminomethyl, alkylaminomethyl or dialkylaminomethyl group, or a methylene group in the cycloalkyl moiety is replaced by an oxygen atom, an imino, N-alkylimino, N-alkylcarbonylimino, N-alkocarbonylimino, (1-pyrrolidinyl)carbonylimino or morpholinocarbonylimino group, a cyclohexylmethyl group which is substituted in position 3 or 4 of the cyclohexyl moiety by an alkoxycarbonylamino or benzyloxycarbonylamino group, a 4-quinuclidinylmethyl group, an ethyl group which is substituted by a carboxyl, alkoxycarbonyl, aminocarbonyl, alkylaminocarbonyl, dialkylaminocarbonyl, (1-pyrrolidinyl)carbonyl or morpholinocarbonyl group, an ethyl group which is substituted in position 2 by a hydroxyl, amino, cyano or 4-aminocyclohexyl group, by a 4-piperidinyl group which can be substituted in position 1 by an alkyl, alkylcarbonyl or alkoxycarbonyl group, or is substituted by a cyclopentyl group in which a methylene group is replaced by an imino or N-alkylimino group, by a 1-piperazinyl group which can be substituted in position 4 by an alkyl, alkoxycarbonyl, alkylcarbonyl, 1-pyrrolidinylcarbonyl or morpholinocarbonyl group, or is substituted by a 3-oxo-1-piperazinyl group which can be substituted in position 4 by an alkyl group, or is substituted by a 2-oxo-1-imidazolidinyl group which can be substituted in position 3 by an alkyl group, a 2,2-dialkoxyethyl group, a $C_{3-5}$-alkyl group which is substituted by an amino group, with the proviso that the two nitrogen atoms of the $R_c$ radical are separated from one another by at least two carbon atoms, an alkyl group which is substituted by a 1-piperazinylcarbonyl group which can be substituted in position 4 by an alkyl, alkoxycarbonyl group or alkylcarbonyl group, a $C_{3-4}$-alkyl group which is substituted by a 4-aminophenyl, phenoxy, $C_{5-6}$-alkyleneimino, alkylamino, dialkylamino, morpholino, alkylcarbonylamino, alkylsulphonylamino, alkoxycarbonylamino, 1-pyrrolidinylcarbonylamino or morpholinocarbonylamino group, with the proviso that the two nitrogen atoms in the $R_c$ radical are separated from one another by at least two carbon atoms, a phenyl group which is substituted in position 4 by an alkycarbonylamino, $(R_8NR_7)$—CO— or $(R_8NR_7)$—CO—$NR_6$— group, where $R_6$, $R_7$ and $R_8$, which can be identical or different, each represent a hydrogen atom or an alkyl group, a cyclohexyl group which is substituted in position 4 by a hydroxyl, amino, alkylamino, dialkylamino, alkoxycarbonylamino, alkylcarbonylamino or N-(alkyl)-N-alkylcarbonylimino group, by an $(R_8NR_7)$—CO—$NR_6$— group, where $R_6$, $R_7$ and $R_8$ are defined as mentioned above, by a benzoylamino, phenylsulphonylamino, phenylacetylamino or 2-phenyipropionylamino group, by a 5- to 6-membered alkyleneimino group, where in the abovementioned 1-piperidinyl groups the methylene group in position 4 can be replaced by an oxygen atom, by an imino, N-alkylimino, N-alkylcarbonylimino, N-alkoxycarbonylimino or N-alkylsulphonylimino group, or is substituted by a 3-oxo-1-piperazinyl group which can be substituted in position 4 by an alkyl group, or is substituted by a cyano, carboxyl, alkoxycarbonyl or an (alkyleneimino)carbonyl group which is optionally substituted by one or two $C_{1-2}$-alkyl groups and has in each case 5 to 6 ring atoms in the alkyleneimino moiety, where in the abovementioned 1-piperidinyl groups the methylene group in position 4 can be replaced by an oxygen or sulphur atom, by a sulphinyl, sulphonyl, imino, N-alkylimino, N-alkylcarbonylimino, N-alkoxycarbonylimino or N-alkylsulphonylimino group, or is substituted by an (alkyleneimino)-$C_{1-2}$-alkyl group having in each case 5 to 6 ring atoms in the alkyleneimino moiety, where in the abovementioned 1-piperidinyl groups the methylene group in position 4 can be replaced by an oxygen atom, by an imino or N-alkylimino group, or is substituted by a $c_{1-2}$-alkyl group which is substituted by an amino, alkylamino, dialkylamino, 1-pyrrolidinyl-carbonyl, 1-piperidinylcarbonyl or morpholinocarbonyl group, a cyclohexyl group which is substituted in position 3 by an amino, alkylamino or dialkylamino group, a cyclohexyl group in which the methylene group in position 3 or 4 is replaced by an imino or N-alkylimino group or the methylene group in position 4 is replaced by an oxygen or sulphur atom, a sulphinyl, suiphonyl, N-formylimino, N-cyanimino, N-alkylcarbonylimino, N-alkoxycarbonylimino, N-(2-aminoethyl)imino, N-aminocarbonylimino, N-alkylaminocarbonylimino, N-(dialkylaminocarbonyl)imino, N-(morpholinocarbonyl)imino or N-(1-pyrrolidinylcarbonyl)imino group, a 4-oxocyclohexyl group, a cyclopentyl group which is substituted in position 3 by an amino, alkylamino, dialkylamino, carboxyl, alkoxycarbonyl, aminocarbonyl, alkylaminocarbonyl, dialkylaminocarbonyl, morpholinocarbonyl or 1-pyrroli-dinylcarbonyl group or in position 1 also by a hydroxy-$C_{1-2}$-alkyl group, a 3-pyrrolidinyl group which is substituted in position 1 by an (alkyleneimino)carbonyl group having in each case 5 to 6 ring atoms in the alkyleneimino moiety, where in the abovementioned 1-piperidinyl groups the methylene group in position 4 can be replaced by an oxygen atom or by an imino, N-allkylimino, N-alkoxycarbonylimino or N-alkylcarbonylimino group, a benzyl group which is substituted in position 4 by an amino, alkylamino or dialkylamino group, a cycloheptyl group in which the methylene group in position 4 is replaced by an imino, N-benzylimino, N-alkylimino, N-alkylcarbonylimino, N-alkoxycarbonylimino or N-alkylsulphonylimino group, or a 3-quinuclidinyl group, where, unless otherwise indicated, the abovementioned alkyl, alkylene and alkoxy moieties each contain 1 to 4 carbon atoms, with the proviso that (i) the $R_aNR_b$ group does not represent a (3-chloro-4-fluorophenyl)amino group when $R_c$ simultaneously represents a 1-piperidinyl group which is substituted in position 4 by an amino or dimethylamino group, a 1-methyl-4-piperidinyloxy, trans-4-hydroxycyclohexylamino, morpholino, N-(4-hydroxycyclohexyl)-N-methylamino or tetrahydro-furfurylamino group, (ii) the $R_aNR_b$ group does not represent a (3-methylphenyl)amino group when $R_c$ simultaneously represents 1-piperidinyl group which is optionally substituted in position 3 or 4 by a hydroxyl group or in position 4 by an aminocarbonyl, amino, acetylamino, methoxycarbonylamino or formylamino group, an amino, $C_{1-4}$-alkyamino, cis-2,5-dimethylmorpholino, 3-quinuclidinylamino, 2-hydroxyethylamino, 4-tetrahydropyranylamino, N-(4-hydroxycyclohexyl)-N-methyl-amino, 4-oxo-cyclohexylamino or cis-4-hydroxycyclohexylamino group, a 4-piperidinylamino group which is optionally substituted in position 1 by a methyl, acetyl, methoxycarbonyl or ethoxycarbonyl group, a cyclohexylamino group which is substituted in position 4 in the trans-configuration by a carboxyl, methoxycarbonyl, (1-pyrrolidinyl)carbonyl, morpholinocarbonyl, amino, dimethylamino, acetylamino, 4-tert-butyloxycarbonylamino or hydroxyl group, (iii) the $R_aNR_b$ group does not represent a phenylamino, (3-methylphenyl)amino, (3-bromophenyl)amino, (3-chlorophenyl)amino or (3-fluorophenyl)amino group when $R_c$ simultaneously represents a morpholino group, (iv) the $R_aNR_b$ group does not represent a (3-fluorophenyl)amino, (3-chlorophenyl)amino or (3-bromophenyl)amino group when $R_c$ simultaneously represents an isopropylamino group, or (v) the $R_aNR_b$ group does not represent a (3-fluorophenyl)amino, (3-chloro-4-methoxyphenyl) amino, (4-chloro-3-nitrophenyl)amino, (4-amino-3-nitrophenyl)amino, (4-amino-3,5-dichlorophenyl) amino, (4-amino-3-cyanophenyl)amino, (4-amino-3,5-dibromophenyl)amino, (3,4-dichlorophenyl) amino, (3-chlorophenyl)amino or (3-bromophenyl) amino group when $R_c$ simultaneously represents a trans-4-hydroxycyclohexylamino group, pharmaceuticals containing these compounds, their use for the treatment of disorders, in particular of oncoses, and their preparation.

However, preferred compounds according to the invention are the abovementioned compounds of the general formula I with the proviso that (i) the $R_aNR_b$ group does not represent a (3-chloro-4-fluorophenyl)amino group when $R_c$ simultaneously represents a 1-piperidinyl group which is substituted in position 3 by an amino, dimethylamino, acetylamino or methoxycarbonylamino group or in position 4 by an amino or dimethylamino group, a 3-piperidinylamino group which is optionally substituted in position 1 by a methyl group, a 1-pyrrolidinyl group which is substituted in position 3 by an amino or dimethylamino group, a 1-piperazinyl group which is substituted in position 4 by a 2-aminoethyl group, a cyclohexylamino group which is substituted in position 4 by a carboxyl, (1-pyrrolidinyl)carbonyl, morpholinocarbonyl, 2-(morpholinocarbonyl)ethyl, amino, dimethylamino, acetylamino, hydroxyl, N-acetyl-N-methylamino, 1-pyrrolidinyl or morpholino group, an N-(4-hydroxycyclohexyl)-N-methylamino group, an n-propylamino group which is substituted in position 3 by a methoxycarbonylamino or morpholino group, a 2-(1-piperazinyl)ethylamino group which is optionally substituted in position 4 of the piperazinyl moiety by a methyl, acetyl or methoxycarbonyl group, a 1-hydroxymethylcyclopentylamino, N-(2-hydroxyethyl)-N-ethylamino, 2-(acetylamino) ethylamino, tetrahydrofurfurylamino, 4-tetrahydropyranylamino, 4-oxocyclohexylamino, morpholino, 4-piperidinylamino, 1-methyl-4-piperidinylamino, tert-butylamino-, isopropylamino, 3-tetrahydrofuranyloxy, 4-tetrahydropyranyloxy, 1-methyl-4-piperidinyloxy or 1-methyl-3-pyrrolidinyloxy group, (ii) the $R_aNR_b$ group does not represent a (3-methylphenyl)amino group when $R_c$ simultaneously represents a 1-piperidinyl group which is optionally substituted in position 3 or 4 by a hydroxyl group or in position 4 by an aminocarbonyl, amino, acetylamino, methoxycarbonylamino or formylamino group, a cyclohexylamino group which is substituted in position 4 by a carboxyl, methoxycarbonyl, (1-pyrrolidinyl) carbonyl, morpholinocarbonyl, amino, dimethylamino, acetylamino, tert-butyloxycarbonylamino or hydroxyl group, a 4-piperidinylamino group which is optionally substituted in position 1 by a methyl, acetyl, methoxycarbonyl, N-methylaminocarbonyl, N,N-dimethylaminocarbonyl, formyl, cyano, aminocarbonyl or ethoxycarbonyl group, an amino, $C_{1-4}$-alkylamino, 2-hydroxyethylamino, 4-oxocyclohexylamino, N-(4-hydroxycyclohexyl)-N-methylamino, tetrahydrofurfurylamino, 4-tetrahydropyranylamino, 3-methylmorpholino or 3-quinuclidinylamino group, a 3,3-, 3,5-, cis-2,5- or trans-2,5-dimethylmorpholino group, (iii) the $R_aNR_b$ group does not represent a phenylamino, (3-methylphenyl)amino, (3-bromophenyl)amino, (3-chlorophenyl)amino, (3-fluorophenyl)amino, (4-amino-3-nitrophenyl)amino, (3,4-dichlorophenyl) amino, (3-nitrophenyl)amino or (3-ethynylphenyl) amino group when $R_c$ simultaneously represents a morpholino group, (iv) the $R_aNR_b$ group does not represent a (3,4-dichlorophenyl)amino, (3-chlorophenyl)amino, (3-bromophenyl)amino, (3-nitrophenyl)amino or (3-ethynylphenyl)amino group when $R_c$ simultaneously represents a cyclohexylamino group which is substituted in position 4 by a carboxyl, (1-pyrrolidinyl) carbonyl, morpholinocarbonyl, amino, dimethylamino, acetylamino or hydroxyl group, a tert-butylamino, isopropylamino, N-(4-hydroxycyclohexyl)-N-methylamino, 4-tetrahydropyranylamino, tetrahydrofurfurylamino, 4-oxocyclohexylamino, 4-piperidinylamino or 1-methyl-4-piperidinylamino group, (v) the $R_aNR_b$ group does not represent a (3-fluorophenyl)amino group when $R_c$ simultaneously represents an isopropylamino group, or (vi) the $R_aNR_b$ group does not represent a (3-fluorophenyl)amino, (3-chloro-4-methoxyphenyl) amino, (4-chloro-3-nitrophenyl)amino, (4-amino-3-nitrophenyl)amino, (4-amino-3,5-dichlorophenyl) amino, (4-amino-3-cyanophenyl)amino, (4-amino-3,5-dibromophenyl)amino, (4-amino-3-chloro-5-bromophenyl)amino or (3,5-dichloro-4-dimethylaminophenyl)amino group when $R_c$ simultaneously represents a 4-hydroxycyclohexylamino group, their tautomers, their stereoisomers and their salts.

Particularly preferred compounds of the general formula I are those in which $R_a$ denotes a hydrogen atom, $R_b$ denotes a 3-chlorophenyl, 3-chloro-4-fluorophenyl, 3-(1,1,2,2-tetrafluoroethoxy)phenyl, 4-amino-3,5-dibromophenyl, 4-amino-3,5-dichlorophenyl, 4-(benzyl)phenyl, 3-(benzyloxy)phenyl, 4-(benzyloxy) phenyl, 4-(benzyloxy)-3-chlorophenyl, 3-(hydroxymethyl)phenyl, 4-biphenylyl, 3-phenoxyphenyl, 4-phenoxyphenyl, 3-chloro-4-phenoxyphenyl, 3-cyanophenyl, 3-trifluoromethoxyphenyl, 3-trifluoromethylphenyl, 3,4-difluorophenyl, 3-nitrophenyl, 3-ethynylphenyl, 4-amino-3-nitrophenyl, 4-chloro-3-nitrophenyl, 3-chloro-4-cyanophenyl or 4-chloro-3-cyanophenyl group or $R_a$ and $R_b$ denote, together with the nitrogen atom located between them, a 1-indolinyl or 1,2,3,4-tetrahydroquinolin-1-yl group and $R_c$ denotes a 3-tetrahydrofuranyloxy or 4-tetrahydropyranyloxy group, a 1-pyrrolidinyl group which is substituted in position 3 by an amino, methylamino or ethylamino group, a 1-pyrrolidinyl group which is substituted in position 4 by a 4-hydroxyphenyl group and additionally in position 2 by a methyl group, a 1-piperidinyl group which is substituted in position 2 by an aminomethyl, (1-pyrrolidinyl) methyl or dimethylaminomethyl group, a 1-piperidinyl group which is substituted in position 3 by an amino, aminomethyl, aminocarbonyl, aminocarbonylmethyl, acetylaminomethyl or methylsulphonylaminomethyl group, a 1-piperidinyl group which is optionally substituted in position 4 by an amino, hydroxyl, formylamino, methoxy, methylamino, ethylamino, morpholinocarbonylamino, methoxycarbonylamino, acetylamino, aminomethyl, methylaminomethyl, ethylaminomethyl, 2-carboxyethyl, 2-methoxycarbonylethyl, 2-(morpholinocarbonyl)ethyl, 2-aminoethyl, 2-aminocarbonylethyl, 2-methylaminocarbonylethyl, 2-dimethylaminocarbonylethyl, 2-(pyrrolidinocarbonyl)ethyl, carboxymethyloxy, methoxycarbonylmethyloxy, aminocarbonylmethyloxy, methylaminocarbonylmethyloxy, dimethylaminocarbonylmethyloxy, morpholinocarbonylmethyloxy, (1-pyrrolidinyl)carbonylmethyloxy, morpholino, 1-pyrrolidinyl, 1-piperidinyl, 4-piperidinyl, 1-methyl-4-piperidinyl, 1-piperazinyl, 4-methyl-1-piperazinyl, 4-dimethylamino-1-piperidinyl, 4-amino-1-piperidinyl, 2-oxo-1-pyrrolidinyl, 4-hydroxy-1-piperidinyl, 4-methylamino-1-piperidinyl, 3-oxo-1-piperazinyl, 4-methyl-3-oxo-1-piperazinyl, N-acetyl-N-methylamino, N-methyl-N-methylsulphonylamino, (1-piperidinyl)methyl, (1-piperazinyl)methyl, (4-methyl-1-piperazinyl)methyl, morpholinomethyl, (1-pyrrolidinyl)methyl, dimethylaminomethyl, acetylaminomethyl, methylsulphonylaminomethyl, cyanomethyl, (1-piperazinyl)carbonyl, (4-methyl-1-piperazinyl)carbonyl, 2-oxo-1-imidazolidinyl or 3-methyl-2-oxo-1-imidazolidinyl group, a 1-piperidinyl group which is substituted by a methyl group and additionally in position 4 by an amino group, a 1-azacycloheptyl or 4-amino-1-azacycloheptyl group, a morpholino or 2,6-dimethylmorpholino group, a 1-piperazinyl group which is substituted in position 4 by a 2-aminoethyl, 2-methoxyphenyl, 3-methoxyphenyl, 4-methoxyphenyl or morpholinocarbonyl group, a 1-homopiperazinyl or 4-methyl-1-homopiperazinyl group, an 8-azabicyclo[3.2.1]-8-octyl group which is substituted in position 3 by an amino, methylamino, dimethylamino or acetylamino group or an ($R_4NR_5$) group in which
$R_4$ denotes a hydrogen atom, a methyl or ethyl group,
$R_5$ denotes a hydrogen atom,
an isopropyl or tert-butyl group,
a methyl group which is substituted by a 2-piperidinyl, 3-piperidinyl, 4-piperidinyl, 1-methyl-4-piperidinyl, 1-tert-butyloxycarbonyl-4-piperidinyl, 1-acetyl-4-piperidinyl, 1-(morpholinocarbonyl)-4-piperidinyl, 1-ethyl-2-pyrrolidinyl, 1-ethyl-3-pyrrolidinyl, 3-aminomethylcyclopentyl, 3-tetrahydrofuryl, 4-quinuclidinyl, 1-piperazinylcarbonyl, 4-methyl-1-piperazinylcarbonyl or 4-acetyl-1-piperazinylcarbonyl group, an ethyl group which is substituted in position 1 by a carboxyl, methoxycarbonyl, aminocarbonyl, methylaminocarbonyl, dimethylaminocarbonyl, 1-pyrrolidinylcarbonyl, morpholinocarbonyl, 1-piperazinylcarbonyl, 4-methyl-1-piperazinylcarbonyl, 4-acetyl-1-piperazinylcarbonyl group or in position 2 by a hydroxyl, amino, cyano, 4-piperidinyl, 1-acetyl-4-piperidinyl, 1-methoxycarbonyl-4-piperidinyl, 1-methyl-2-pyrrolidinyl, 1-piperazinyl, 3-oxo-1-piperazinyl, 4-methyl-3-oxo-1-piperazinyl, 4-tert-butyloxycarbonyl-1-piperazinyl, 4-acetyl-1-piperazinyl, 4-(morpholinocarbonyl)-1-piperazinyl, 2-oxo-1-imidazolidinyl, 3-methyl-2-oxo-1-imidazolidinyl or 4-aminocyclohexyl group, a 2,2-dimethoxyethyl group, a 1-propyl group which is substituted in position 2 by an amino group and optionally additionally in position 2 by a methyl group, a 1-propyl group which is substituted in position 3 by an amino, morpholino, acetylamino, methylsulphonylamino, methoxycarbonylamino or morpholinocarbonylamino group, a 2-propyl group which is substituted in position 1 by an amino, phenoxy, 4-aminophenyl, 1-piperidinyl or diethylamino group, a 2-propyl group which is substituted in position 1 by an amino group and additionally in position 2 by a methyl group, a 2-propyl group which is substituted in position 2 by a (1-piperazinyl)carbonyl, (4-methyl-1-piperazinyl)carbonyl or (4-acetyl-1-piperazinyl)carbonyl group, a 4-aminobutyl or a 5-aminopentyl group, a phenyl group which is substituted in position 4 by an acetylamino, dimethylaminocarbonyl, dimethylaminocarbonylamino, ethylaminocarbonylamino or N-(dimethylaminocarbonyl)-N-methylamino group, a cyclohexyl group which is substituted in position 4 by a hydroxyl, amino, methylamino, ethylamino, dimethylamino, methoxycarbonylamino, N-acetyl-N-methylamino, dimethylaminocarbonylamino, ethylaminocarbonylamino, benzoylamino, phenylsulphonylamino, phenylacetylamino, 2-phenylpropionylamino, morpholino, 1-pyrrolidinyl, 1-piperidinyl, 4-amino-1-piperidinyl, 4-dimethylamino-1-piperidinyl, 1-piperazinyl, 1-methyl-4-piperazinyl, 3-oxo-1-piperazinyl, 4-methyl-3-oxo-1-piperazinyl, 4-acetyl-1-piperazinyl, cyano, carboxyl, morpholinocarbonyl, (1-pyrrolidinyl)carbonyl, methoxycarbonyl, (4-methyl-1-piperazinyl)carbonyl, (1-piperazinyl)carbonyl, (2,6-dimethylmorpholino)carbonyl, thiomorpholinocarbonyl, thiomorpholinocarbonyl S-oxide, thiomorpholinocarbonyl S,S-dioxide, (4-acetyl-1-piperazinyl)carbonyl, aminomethyl, methylaminomethyl, ethylaminomethyl, dimethylaminomethyl, 1-piperidinylmethyl, 1-pyrrolidinylmethyl, morpholinomethyl, 1-piperazinylethyl, 4-methyl-1-piperazinylmethyl, 2-aminoethyl, 2-(morpholinocarbonyl)ethyl or 2-(1-pyrrolidinylcarbonyl)ethyl group, a 3-aminocyclohexyl or 3-dimethylaminocyclohexyl group, a 4-oxocyclohexyl group, a cyclohexylmethyl group which is substituted in the cyclohexyl moiety in position 4 by an amino, aminomethyl or benzyloxycarbonylamino group or in position 3 by an aminomethyl group, a 3-piperidinyl group which is optionally substituted in position 1 by a methyl or ethyl group, a 4-piperidinyl group which is optionally substituted in position 1 by a formyl, cyano, methyl, tert-butylooxycarbonyl, methoxycarbonyl, 2-aminoethyl, morpholinocarbonyl or (N,N-dimethylamino) carbonyl group, a cyclopentyl group which is substituted in position 1 by a hydroxymethyl or in position 3 by an amino, carboxyl, methoxycarbonyl or morpholinocarbonyl group, a 4-aminobenzyl group, a 4-tetrahydropyranyl, 4-tetrahydrothiopyranyl S-oxide or 4-tetrahydrothiopyranyl S,S-dioxide group, a 3-quinuclidinyl, 1-benzyl-4-(azacycloheptyl), 1-tert-butyloxycarbonyl-4-(azacycloheptyl), 4-(azacycloheptyl) or 1-(morpholinocarbonyl)-3-pyrrolidinyl group, with the proviso that the compounds 4-[(4-amino-3,5-dibromophenyl)amino]-6-[(trans-4-hydroxycyclo-hexyl)amino]pyrimido[5,4-d]pyrimidine, 4-[(3-chloro-4-fluorophenyl)amino]-6-[4-amino-1-piperidinyl]pyrimido[5,4-d]pyrimidine, 4-[(3-chloro-4-fluorophenyl)amino]-6-[3-amino-1-pyrrolidinyl]pyrimido[5,4 -d]pyrimidine, 4-[(3-chloro-4-fluorophenyl)amino]-6-[4-(2-aminoethyl)-1-piperazinyl]pyrimido[5,4-d]pyrimidine, 4-[(3-chloro-4-fluorophenyl)aminol]-6-[3-amino-1-piperidinyl]pyrimido[5,4-d]pyrimidine 4-[(3-chloro-4-fluorophenyl)amino]-6-[3-piperidinyl amino]pyrimido[5,4-d]pyrimidine, 4-[(3-chloro-4-fluorophenyl)amino]-6-[1-methyl-3-piperidinyl-amino]pyrimido[5,4-d]pyrimidine, 4-[(3-chloro-4-fluorophenyl)amino]-6-[4-(N-acetyl-N-methylamino)cyclohexylamino]pyrimido[5,4-d]pyrimidine, 4-[(3-chloro-4-fluorophenyl)amino]-6-[4-(1-pyrrolidinyl)cyclo-hexylamino]pyrimido[5,4-d]pyrimidine, 4-[(3-chloro-4-fluorophenyl)amino]-6-[4-(morpholino)cyclohexyl-amino]pyrimido[5,4-d]pyrimidine, 4-[(3-chloro-4-fluorophenyl)amino]-6-[trans-4-(2-(morpholinocarbonyl)ethyl)cyclohexylamino]pyrimido[5,4-d]pyrimidine, 4-[(4-amino-3-nitrophenyl)amino]-6-[(trans-4-hydroxycyclohexyl)amino]pyrimido[5,4-d]pyrimidine, 4-[(4-chloro-3-nitrophenyl)amino]-6-[(trans-4-hydroxycyclohexyl)amino]pyrimido[5,4-d]pyrimidine, 4-[(4-amino-3,5-dichlorophenyl)amino]-6-[(trans-4-hydroxycyclohexyl)amino]pyrimido[5,4-d]pyrimidine, 4-[(3-chloro-4-fluorophenyl)amino]-6-[1-(hydroxymethyl)cyclo-pentylamino]pyrimido[5,4-d]pyrimidine, 4-[(3-chloro-4-fluorophenyl)amino]-6-[N-methyl-N-(2-hydroxy-ethyl)amino]pyrimido[5,4-d]pyrimidine, 4-[(3-chloro-4-fluorophenyl)amino]-6-[3-(methoxycarbonylamino)-1-propylamino]pyrimido[5,4-d]pyrimidine, 4-[(3-chloro-4-fluorophenyl)amino]-6-(3-(morpholino)-1-propylamino)pyrimido[5,4-d]pyrimidine, 4-[(3-chloro-4-fluorophenyl)amino]-6-[2-(1-piperazinyl)-1-ethylamino]pyrimido[5,4-d]pyrimidine, 4-[(3-chloro-4-fluorophenyl)amino]-6-[2-(1-acetyl-4-piperazinyl)ethylamino]pyrimido[5,4-d]pyrimidine, 4-[(4-amino-3-nitrophenyl)amino]-6-(morpholino)pyrimido[5,4-d]pyrimidine, 4-[(3-chloro-4-fluorophenyl)amino]-6-(4-tetrahydropyranyloxy)pyrimido[5,4-d]pyrimidine, 4-[(3-chloro-4-fluorophenyl)amino]-6-(3-tetrahydrofuranyloxy)pyrimido[5,4-d]pyrimidine and the compounds in which the $R_aNR_b$ group represents a 3-chlorophenylamino, (3-chloro-4-fluorophenyl)amino, (3-nitrophenyl)amino or (3-ethynylphenyl)amino group when $R_c$ simultaneously represents a 4-tetrahydropyranylamino, tetrahydrofurfurylamino, 4-oxocyclohexylamino, morpholino, 4-piperidinylamino, isopropylamino, 1-methyl-4-piperidinylamino, tert-butylamino, N-(4-hydroxycyclohexyl)-N-methylamino, 4-hydroxycyclohexylamino, 4-aminocyclohexylamino, 4-dimethylaminocyclohexylamino, trans-4-carboxycyclohexylamino, trans-4-(1-pyrrolidinyl)carbonylcyclohexylamino or trans-4-morpholinocarbonylcyclohexylamino group, are excepted, their tautomers, their stereoisomers and their salts.

Very particularly preferred compounds of the general formula I are those in which $R_a$ denotes a hydrogen atom, $R_b$ denotes a 3-chlorophenyl, 3-chloro-4-fluorophenyl, 3-(1,1,2,2-tetrafluoroethoxy)phenyl, 4-amino-3,5-dibromophenyl, 4-amino-3,5-dichlorophenyl, 4-(benzyl)phenyl, 3-(benzyloxy)phenyl, 4-(benzyloxy)phenyl, 3-(hydroxymethyl)phenyl, 4-biphenylyl, 3-phenoxyphenyl, 4-phenoxyphenyl, 3-trifluoromethoxyphenyl, 3-cyanophenyl, 3-trifluoromethylphenyl, 3,4-difluorophenyl, 3-nitrophenyl, 3-ethynylphenyl, 4-amino-3-nitrophenyl, 4-chloro-3-nitrophenyl, 4-(benzyloxy)-3-chlorophenyl, 3-chloro-4-phenoxyphenyl, 3-chloro-4-cyanophenyl or 4-chloro-3-cyanophenyl group or $_{Ra}$ and $R_b$ denote, together with the nitrogen atom located between them, a 1-indolinyl or 1,2,3,4-tetrahydroquinolin-1-yl group, $R_c$ denotes a 1-pyrrolidinyl group which is substituted in position 4 by a 4-hydroxyphenyl group and additionally in positi6n 2 by a methyl group, a 1-piperidinyl group which is optionally substituted in position 4 by an amino, methylamino, hydroxyl, formylamino, methoxycarbonylamino, N-methyl-N-methylsulphonylamino, aminomethyl, morpholino, 1-pyrrolidinyl, 1-piperazinyl, 1-methyl-4-piperazinyl, (1-methyl-4-piperazinyl)methyl, 4-dimethylamino-1-piperidinyl, 4-piperidinyl or 1-methyl-4-piperidinyl group, a 4-amino-3-methyl-1-piperidinyl group, a 4-amino-4-methyl-1-piperidinyl group, a 1-piperidinyl group which is substituted in position 3 by an aminomethyl, aminocarbonyl or aminocarbonylmethyl group, a 1-azacycloheptyl or 4-amino-1-azacycloheptyl group, a morpholino group, a 1-piperazinyl group which is substituted in position 4 by a 2-methoxyphenyl, 3-methoxyphenyl or 4-methoxyphenyl group, a 1-homopiperazinyl or 4-methyl-1-homopiperazinyl group, an 8-azabicyclo[3.2.1]-8-octyl group which is substituted in position 3 by an amino or acetylamino group or an ($R_4NR_5$) group in which $R_4$ represents a hydrogen atom, a methyl or ethyl group, $R_5$ represents a hydrogen atom, a methyl group which is substituted by a 3-tetrahydrofuryl, 4-piperidinyl, 1-methyl-4-piperidinyl, 1-tert-butyloxycarbonyl-4-piperidinyl or 4-quinuclidinyl group, an ethyl group which is substituted in position 2 by hydroxyl, amino, 4-tert-butyloxycarbonyl-1-piperazinyl or 4-(morpholinocarbonyl)-1-piperazinyl group, a 2,2-dimethoxyethyl group, a 1-propyl group which is substituted in position 2 by an amino group and optionally additionally in position 2 by a methyl group, a 1-propyl group which is substituted in position 3 by an amino group, a 2-propyl group which is substituted in position 1 by a phenoxy, 4-aminophenyl, 1-piperidinyl or diethylamino group, a 2-propyl group which is substituted in position 1 by an amino group and additionally in position 2 by a methyl group, a 4-aminobutyl or a 5-aminopentyl group, a cyclohexyl group which is substituted in position 4 by a hydroxyl, dimethylamino, 1-methyl-4-piperazinyl, 1-piperazinylcarbonyl, 1-methyl-4-piperazinylcarbonyl, 4-dimethylamino-1-piperidinyl, carboxyl, morpholinocarbonyl, (1-pyrrolidinyl)carbonyl, methoxycarbonyl, aminomethyl, methylamino, methoxycarbonylamino, 2-(morpholinocarbonyl)ethyl or 2-(1-pyrrolidinylcarbonyl)ethyl group, a cyclohexylmethyl group which is substituted in the cyclohexyl moiety in position 4 by an amino, aminomethyl or benzyloxycarbonylamino group or in position 3 by an aminomethyl group, a 1-methyl-3-piperidinyl group, a 4-piperidinyl group which is substituted in position 1 by a cyano, methyl, tert-butyloxycarbonyl, (N,N-dimethylamino)carbonyl or methoxycarbonyl group, a 4-aminobenzyl group, a 3-quinuclidinyl, 1-benzyl-4-(azacycloheptyl), 1-tert-butyloxycarbonyl-4-(azacycloheptyl) or 4-(azacycloheptyl) group, with the proviso that the compounds 4-[(4-amino-3,5-dibromophenyl)amino]-6-[(trans-4-hydroxycyclohexyl)amino]pyrimido[5,4-d]pyrimidine, 4-[(4-amino-3,5-dichlorophenyl)amino]-6-[(trans-4-hydroxycyclohexyl)amino]pyrimido[5,4-d]pyrimidine, 4-[(4-amino-3-nitrophenyl)amino]-6-[(trans-4-hydroxycyclohexyl)amino]pyrimido[5,4-d]pyrimidine, 4-[(4-amino-3-nitrophenyl)amino]-6-(morpholino)pyrimido[5,4-d]pyrimidine, 4-[(4-chloro-3-nitrophenyl)amino]-6-[(trans-4-hydroxycyclohexyl)amino]pyrimido[5,4-d]pyrimidine, and the compounds in which the $R_aNR_b$ group represents a (3-chlorophenyl)amino, (3-nitrophenyl)amino or (3-ethynylphenyl)amino group when $R_c$ simultaneously represents a tetrahydrofurfurylamino, morpholino, 1-methyl-4-piperidinylamino, N-(4-hydroxycyclohexyl)-N-methylamino, 4-hydroxycyclohexylamino, 4-dimethylaminocyclohexylamino, trans-4-carboxycyclohexylamino, trans-4-(1-pyrrolidinyl)carbonylcyclohexylamino or trans-4-morpholinocarbonylcyclohexylamino group, and the compounds in which the $R_aNR_b$ group represents a (3-chloro-4-fluorophenyl)amino group when $R_c$ simultaneously represents a 1-methyl-3-piperidinylamino, tetrahydrofurfurylamino, 3-(methoxycarbonylamino)-1-propylamino, N-methyl-N-(2-hydroxyethyl)amino, 4-amino-1-piperidinyl, morpholino, 1-methyl-4-piperidinylamino, 4-hydroxycyclohexylamino, 4-dimethylaminocyclohexylamino, N-(4-hydroxycyclohexyl)-N-methylamino, trans-4-carboxycyclohexylamino, trans-4-(2-(morpholinocarbonyl)ethyl)cyclohexylamino, trans-4-(1-pyrrolidinyl)carbonylcyclohexylamino or trans-4-morpholinocarbonylcyclohexylamino group, are excepted, their tautomers, their stereoisomers and their salts.

The following particularly valuable compounds of the general formula I may be mentioned by way of example:

4-[(3-chloro-4-fluorophenyl)amino]-6-[4-methoxycarbonylamino-1-piperidinyl]pyrimido[5,4-d]pyrimidine, 4-[(3-chloro-4-fluorophenyl)amino]-6-[(3-quinuclidinyl)-amino]pyrimido[5,4-d]pyrimidine, 4-[(3-chloro-4-fluorophenyl)amino]-6-[4-formylamino-1-piperidinyl]pyrimido[5,4-d]pyrimidine, 4-[(3-chloro-4-fluorophenyl)amino]-6-[4-(aminomethyl)-1-piperidinyl]pyrimido[5,4-d]pyrimidine, 4-[(3-chloro-4-fluorophenyl)amino]-6-[1-methoxycarbonyl-4-piperidinylamino]pyrimido[5,4-d]pyrimidine, 4-[(3-chloro-4-fluorophenyl)amino]-6-[3-amino-propylamino]pyrimido[5,4-d]pyrimidine, 4-[(3-chloro-4-fluorophenyl)amino]-6-[4-aminobenzyl-amino]pyrimido[5,4-d]pyrimidine, 4-[(4-amino-3,5-dichlorophenyl)amino]-6-[trans-4-(morpholino-carbonyl)cyclohexylamino]pyrimido[5,4-d]pyrimidine, 4-[(4-amino-3,5-dichlorophenyl)amino]-6-[trans-4-(pyrrolidino-carbonyl)cyclohexylamino]pyrimido[5,4-d]pyrimidine, 4-[(3-chloro-4-fluorophenyl)amino]-6-[4-(4-piperidinyl)-1-piperidinyl]pyrimido[5,4-d]pyrimidine, 4-[(3-chloro-4-fluorophenyl)amino]-6-[4-(aminomethyl)-cyclohexylmethylamino]pyrimido[5,4-d]pyrimidine, 4-[(3-chloro-4-fluorophenyl)amino]-6-[4-quinuclidinyl-methylamino]pyrimido[5,4-d]pyrimidine, 4-[(3-chloro-4-fluorophenyl)amino]-6-[2-amino-2-methyl-1-propylamino]pyrimido[5,4-d]pyrimidine, 4-[(3-chloro-4-fluorophenyl)amino]-6-[N-methyl-N-(1-methyl-4-piperidinyl)amino]pyrimido[5,4-d]pyrimidine, 4-[(3-chloro-4-fluorophenyl)amino]-6-[4-piperidinyl-methylamino]pyrimido[5,4-d]pyrimidine, 4-[(3-chloro-4-fluorophenyl)amino]-6-[4-(morpholino)-1-piperidinyl]pyrimido[5,4-d]pyrimidine, 4-[(3-chloro-4-fluorophenyl)amino]-6-[4-(1-pyrrolidinyl)-1-piperidinyl]pyrimido[5,4-d]pyrimidine, 4-[(3-chloro-4-fluorophenyl)amino]-6-[3-(aminoniethyl)-cyclohexylmethylamino]pyrimido[5,4-d]pyrimidine, 4-[(3-chloro-4-fluorophenyl)amino]-6-[4-(1-methyl-4-piperidinyl)-1-piperidinyl]pyrimido[5,4-d]pyrimidine, 4-[(3-chloro-4-fluorophenyl)amino]-6-[4-(1-methyl-4-piperazinyl)cyclohexylamino]pyrimido[5,4-d]pyrimidine, 4-[(3-chloro-4-fluorophenyl)amino]-6-[4-hydroxy-1-piperidinyl]pyrimido[5,4-d]pyrimidine, 4-[(3-chloro-4-fluorophenyl)amino]-6-[(1-cyano-4-piperidinyl)amino]pyrimido[5,4-d]pyrimidine, 4-[(3-chloro-4-fluorophenyl)amino]-6-[(1-methyl-4-piperidinyl)methylamino]pyrimido[5,4-d]pyrimidine, 4-[(3-chloro-4-fluorophenyl)amino]-6-[2-(4-(morpholino-carbonyl)-1-piperazinyl)ethylamino]pyrimido[5,4-d]pyrimidine, 4-[(3-chloro-4-fluorophenyl)amino]-6-[4-amino-1-azacyclo-heptyl]pyrimido[5,4-d]pyrimidine, 4-[(3-chloro-4-fluorophenyl)amino]-6-[4-(azacycloheptyl)-amino]pyrimido[5,4-d]pyrimidine, 4-[(3-chloro-4-fluorophenyl)amino]-6-[trans-4-aminomethyl-cyclohexylamino]pyrimido[5,4-d]pyrimidine, 4-[(3-chloro-4-fluorophenyl)amino]-6-[3-aminomethyl-1-piperidinyl]pyrimido[5,4-d]pyrimidine, 4-[(3-chloro-4-fluorophenyl)amino]-6-[4-(1-methyl-4-piperidinyl)-1-piperidinyl]pyrimido[5,4-d]pyrimidine, 4-[(3-chloro-4-fluorophenyl)amino]-6-[4-amino-4-methyl-1-piperidinyl]pyrimido[5,4-d]pyrimidine, 4-[(3-chloro-4-fluorophenyl)amino]-6-[endo-3-acetylamino-8-azabicyclo[3.2.1]-8-octyl]pyrimido[5,4-d]pyrimidine, 4-[(3-chloro-4-fluorophenyl)amino]-6-[4-(4-amino-1-piperidinyl)methyl-1-piperidinyl]pyrimido[5,4-d]pyrimidine, 4-[(4-benzyloxyphenyl)amino]-6-[trans-4-dimethylamino-cyclohexylamino]pyrimido[5,4-d]pyrimidine, (3'S)-4-[3-chlorophenylamino]-6-[(3'-quinuclidinyl)amino]pyrimido[5,4-d]pyrimidine, 4-[(3-chloro-4-fluorophenyl)amino]-6-[1-dimethylaminocarbonyl-4-piperidinylamino]pyrimido[5,4-d]pyrimidine, (3'S)-4-[(3-chloro-4-fluorophenyl)amino]-6-[(3'-quinuclidinyl)-amino]pyrimido[5,4-d]pyrimidine, (3'R)-4-[(3-chloro-4-fluorophenyl)amino]-6-[(3'-quinuclidinyl)-amino]pyrimido[5,4-d]pyrimidine, 4-[(3-chloro-4-fluorophenyl)amino]-6-[1-methyl-4-piperidinylamino]pyrimido[5,4-d]pyrimidine and their salts.

The compounds of the general formula I can be prepared, for example, by bthe following processes:

a) Reaction of a compound of the general formula

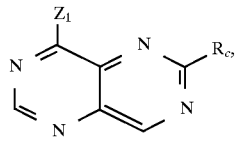
(II)

in which $R_c$ is as defined at the outset, and $Z_1$ represents a leaving group such as a halogen atom, for example a chlorine or bromine atom or a methylsulphonyl or a hydroxyl group, with an amine of the general formula

(III)

in which $R_a$ and $R_b$ are as defined at the outset.

The reaction is expediently carried out in a solvent such as isopropanol, butanol, tetrahydrofuran, dioxane, toluene, clorobenzene, dimethylformamide, dimethyl sulphoxide, ethylene glycol monomethyl ether, ethylene glycol diethyl ether or sulpholane, where appropriate in the presence of an inorganic base, for example sodium carbonate or potassium hydroxide, or of a tertiary organic base, for example triethylamine or pyridine, it also being possible for the latter simultaneously to act as solvent, and where appropriate in the presence of a reaction promoter such as a copper salt, an appropriate amine hydrohalide or alkali metal halide at temperatures between 0° and 200° C. but preferably at temperatures between 60° and 150° C. The reaction can, however, also be carried out without solvent or in an excess of the compound of the general formula III employed.

If $Z_1$ denotes a hydroxyl group, the reaction is expediently carried out in the presence of hexamethyldisilazane, preferably without other solvent and, where appropriate in the presence of a reaction promoter such as an organic acid such as, for example, toluenesulphonic acid at temperatures between 0° and 200° C., but preferably at temperatures between 60° and 180° C.

b) To prepare compounds of the general formula I in which $R_c$ represents one of the radicals mentioned for $R_c$ at the outset and linked via an oxygen or nitrogen atom to the pyrimido[5,4-d]pyrimidine:

Reaction of a compound of the general formula

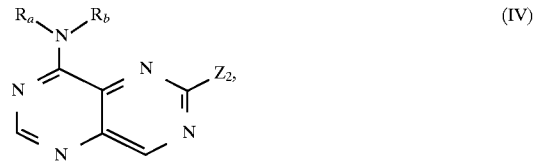
(IV)

in which $R_a$ and $R_b$ are as defined at the outset, and $Z_2$ represents a leaving group such as a halogen atom, a substituted hydroxyl, mercapto, sulphinyl or sulphonyl group such as a chlorine or bromine atom, a methoxy, ethoxy, phenoxy, methylsulphinyl, ethylsulphinyl, methylsulphonyl or ethylsulphonyl group, with a compound of the general formula

(V)

in which $R_c$ represents the radicals mentioned for $R_c$ at the outset and linked via an oxygen or nitrogen atom to the pyrimido[5,4-d]pyrimidine.

The reaction is expediently carried out in a solvent such as isopropanol, butanol, tetrahydrofuran, dioxane, toluene, chlorobenzene, dimethylformamide, dimethyl sulphoxide, ethylene glycol monomethyl ether, ethylene glycol diethyl ether or sulpholane, where appropriate in the presence of an inorganic base, for example sodium carbonate or potassium hydroxide, or of a tertiary organic base, for example triethylamine or pyridine, it also being possible for the latter simultaneously to act as solvent, and where appropriate in the presence of a reaction promoter such as a copper salt, an appropriate amine hydrohalide or alkali metal halide at temperatures between 0° and 150° C. but referably at temperatures between 20° and 120° C. The reaction can, however, also be carried out without solvent or in an excess of the compound of the general formula V employed.

With an alcohol of the general formula V the reaction is preferably carried out in an appropriate alcohol and, where appropriate, in the presence of an organic or inorganic base such as with the appropriate alkali metal alcoholate at temperatures between 0° and 100° C.

If the result according to the invention is a compound of the general formula I containing an amino, alkylamino or imino group, the latter can be converted by acylation or sulphonylation into a corresponding acyl or sulphonyl compound of the general formula I, or a compound of the general formula I containing an amino, alkylamino or imino group, the latter can be converted by alkylation or reductive alkylation into a corresponding alkyl compound of the general formula I, or a compound of the general formula I containing a carboxyl group, the latter can be converted by esterification into a corresponding ester of the general formula I, or a compound of the general formula I containing a carboxyl or ester group, the latter can be converted by amidation into a corresponding amide of the general formula I, or a compound of the general formula I containing a primary or secondary hydroxyl group, the latter can be converted by oxidation into a corresponding carbonyl compound of the general formula I.

Subsequent esterification is carried out where appropriate in a solvent or solvent mixture such as methylene chloride, dimethylformamide, benzene, toluene, chlorobenzene, tetrahydrofuran, benzene/tetrahydrofuran or dioxane or, particularly advantageously, in a corresponding alcohol, where appropriate in the presence of an acid such as hydrochloric acid or in the presence of a dehydrating agent, for example in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole and, where appropriate, additionally in the presence of 4-dimethylaminopyridine, N,N'-carbonyldiimidazole or triphenylphosphine/tetrachloromethane, expediently at temperatures between 0° and 150° C. preferably at temperatures between 0° and 80° C.

Subsequent acylation or sulphonylation is, where appropriate, carried out in a solvent or solvent mixture such as methylene chloride, dimethylformamide, benzene, toluene, chlorobenzene, tetrahydrofuran, benzene/tetrahydrofuran or dioxane with an appropriate acyl or sulphonyl derivative, where appropriate in the presence of a tertiary organic base or in the presence of an inorganic base or in the presence of a dehydrating agent, for example in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole and, where appropriate, additionally in the presence of 4-dimethylaminopyridine, N,N'-carbonyldiimidazole or triphenylphosphine/tetrachloromethane, expediently at temperatures between 0° and 150° C. preferably at temperatures between 0° and 80° C.

Subsequent alkylation is carried out, where appropriate, in a solvent or solvent mixture such as methylene chloride, dimethylformamide, benzene, toluene, chlorobenzene, tetrahydrofuran, benzene/tetrahydrofuran or dioxane with an alkylating agent such as an appropriate halide or sulphonic ester, for example with methyl iodide, ethyl bromide, dimethyl sulphate or benzyl chloride, where appropriate in the presence of a tertiary organic base or in the presence of an inorganic base, expediently at temperatures between 0° and 150° C. preferably at temperatures between 0° and 100° C.

Subsequent reductive alkylation is carried out with an appropriate carbonyl compound such as formaldehyde, acetaldehyde, propionaldehyde, acetone or butyraldehyde in the presence of a complex metal hydride such as sodium borohydride, lithium borchydride or sodium cyanoborohydride, expediently at a pH of 6–7 and at room temperature or in the presence of a hydrogenation catalyst, for example with hydrogen in the presence of palladium/carbon, under a pressure of 1 to 5 bar of hydrogen. The methylation is, however, preferably carried out in the presence of formic acid as reducing agent at elevated temperatures, for example at temperatures between 60° and 120° C.

Subsequent amidation is carried out by reacting an appropriate reactive carboxylic acid derivative with an appropriate amine, where appropriate in a solvent or solvent mixture such as methylene chloride, dimethylformamide, benzene, toluene, chlorobenzene, tetrahydrofuran, benzene/tetrahydrofuran or dioxane, it being possible for the amine employed simultaneously to act as solvent, where appropriate in the presence of a tertiary organic base or in the presence of an inorganic base or with an appropriate carboxylic acid in the presence of a dehydrating agent, for example in the presence of isobutyl chloroformate, thionyl chloride, trimethylchlorosilane, sulphuric acid, methanesulfonic acid, p-toluenesulphonic acid, phosphorus trichloride, phosphorus pentoxide, O-(benzotriazol-1-yl)-N,N,N',N'-tetramethyluronium tetrafluoroborate, N,N'-dicyclohexylcarbodiimide, N,N'-dicyclohexylcarbodiimide/N-hydroxysuccinimide or 1-hydroxybenzotriazole and, where appropriate, additionally in the presence of 4-dimethylaminopyridine, N,N'-carbonyldiimidazole or triphenylphosphine/tetrachloromethane, expediently at temperatures between 0° and 150° C., preferably at temperatures between 0° and 80° C.

Subsequent oxidation is carried out, where appropriate, in a solvent such as methylene chloride, water, dimethylformamide, benzene, chlorobenzene, tetrahydrofuran or dioxane with an oxidizing agent such as chromic acid, chromium trioxide and pyridine, pyridinium dichromate, pyridinium chlorochromate, oxalyl chloride/dimethyl sulphoxide/triethylamine, tetra-n-propyl perruthenate/N-methylmorpholine N-oxide, ruthenium trichloride/sodium metaperiodate or Dess-Martin reagent, expediently at temperatures at between –80° and 100° C. preferably at temperatures between –80° C. and room temperature.

During the reaction described above, reactive groups which are present where appropriate, such as hydroxyl, carboxyl, amino, alkylamino or imino groups, can be protected during the reaction by conventional protective groups which are eliminated again after the reaction.

For example, a suitable protective radical for a hydroxyl group is the trimethylsilyl, acetyl, benzoyl, methyl, ethyl, tert-butyl, trityl, benzyl or tetrahydropyranyl group, suitable protective radicals for a phosphono group are an alkyl group such as the methyl, ethyl, isopropyl or n-butyl group, the phenyl or benzyl group, suitable protective radicals for a carboxyl group are the trimethylsilyl, methyl, ethyl, tert-butyl, benzyl or tetrahydropyranyl group, suitable protective radicals for a phosphono group are an alkyl group such as the methyl, ethyl, isopropyl, or n-butyl group, the phenyl or benzyl group, suitable protective radicals for an amino, alkylamino or imino group are the formyl, acetyl, trifluoroacetyl, ethoxycarbonyl, tert-butoxycarbonyl, benzyloxycarbonyl, benzyl, methoxybenzyl or 2,4-dimethoxybenzyl group and for the amino group in addition the phthalyl group and suitable protective radicals for the nitrogen atom in a 1-azabicycloalkyl group such as the quinuclidinyl group are the benzyl group or borane.

The subsequent elimination where appropriate of a protective radical which has been used takes place, for example, by hydrolysis in an aqueous solvent, for example in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, for example, in the presence of iodotrimethylsilane, at temperatures between 0° and 120° C., preferably at temperatures between 10° and 100° C.

However, a benzyl, methoxybenzyl or benzyloxycarbonyl radical is eliminated, for example, by hydrogenolysis, for example with hydrogen in the presence of a catalyst such as palladium/carbon in a suitable solvent such as methanol, ethanol, ethyl acetate or glacial acetic acid, where appropriate with the addition of an acid such as hydrochloric acid at temperatures between 0° and 100° C., but preferably at temperatures between 20° and 60° C., and under a pressure of 1 to 7 bar, but preferably of 3 to 5 bar, of hydrogen. However, a 2,4-dimethoxybenzyl radical is preferably eliminated in trifluoroacetic acid in the presence of anisole.

A tert-butyl or tert-butyloxycarbonyl radical is preferably eliminated by treatment with an acid such as trifluoroacetic acid or hydrochloric acid or by treatment with iodotrimethylsilane, where appropriate using a solvent such as methylene chloride, dioxane, methanol or diethyl ether.

A trifluoroacetyl radical is preferably eliminated by treatment with an acid such as hydrochloric acid, where appropriate in the presence of a solvent such as acetic acid, at temperatures between 50° and 120° C. or by treatment with sodium hydroxide solution, where appropriate in the presence of a solvent such as tetrahydrofuran at temperatures between 0° and 50° C.

A phthalyl radical is preferably eliminated in the presence of hydrazine or of a primary amine such as methylamine, ethylamine or n-butylamine in a solvent such as methanol, ethanol, isopropanol, toluene/water or dioxane at temperatures between 20° and 50° C.

Cleavage of the complex of a 1-azabicycloalkyl group such as the quinuclidinyl group with borane preferably takes place by treatment with an acid such as hydrochloric acid and, where appropriate, in the presence of a solvent such as methanol, ethanol, acetic acid or dioxane at temperatures between 0° C. and the boiling point of the reaction mixture. It is possible in this reaction for an ester group which is present where appropriate simultaneously to be converted into the corresponding carboxyl group.

It is furthermore possible for the resulting compounds of the general formula I to be, as has already been mentioned at the outset, fractionated into their enantiomers and/or diastereomers. Thus for example, cis/trans mixtures can be fractioned into their cis and trans isomers, and compounds with at least one optically active carbon atom can be fractionated into their enantiomers.

Thus, for example, the resulting cis/trans mixtures can be fractionated by chromatography into their cis and trans isomers, the resulting compounds of the general formula I which occur in racemates can be fractionated by methods known per se (see Allinger N. L. and Eliel E. L. in "Topics in Stereochemistry", Vol. 6, Wiley Interscience, 1971) into their optical antipodes and compounds of the general formula I with at least 2 asymmetric carbon atoms can be fractionated on the basis of their physicochemical differences by methods known per se, foe example by chromatography and/or fractional cryctallization into their diastereomers which, if they result in racemic form, can subsequently be separated into the enantiomers as mentioned above.

Enantiomers are preferably separated by column separation on chiral phases or by recrystrallization from an optically active solvent or by reaction with an optically active substance which forms salts or derivatives such as, for example, esters or amides with the racemic compound, in particular acids and their activated derivatives or alcohols, and separation of the diastereomeric salt mixture or derivative obtained in this way, for example on the basis of different solubilities, it being possible to liberate the free antipodes from the pure diastereomeric salts or derivatives by the action of suitable agents. Examples of particularly useful optically active acids are the D and L forms of tartaric acid or dibenzoyltartaric acid, di-o-tolyltartaric acid, malic acid, mandelic acid, camphorsulphonic acid, glutamic acid, aspartic acid or quinic acid. An example of a suitable optically active alcohol is (+)- or (−)-menthol and of an optically active acyl radical in amides is (+)- or (−)-menthyloxycarbonyl.

It is furthermoxe possible for the resulting compounds of the formula I to be converted into their salts, in particular for pharmaceutical use into their physiologically tolerated salts with inorganic or organic acids. Examples of acids suitable for this purpose are hydrochloric acid, hydrobromic acid, sulphuric acid, phosphoric acid, fumaric acid, succinic acid, lactic acid, citric acid, tartaric or maleic acid.

In addition, the novel compounds of the formula I obtained in this way can, if they contain a carboxyl, phosphono, o-alkylphosphono, sulpho or 5-tetrazolyl group, subsequently be converted if required into their salts with inorganic or organic bases, in particular for pharmaceutical use into their physiologically tolerated salts. Examples of bases suitable in this connection are sodium hydroxide, potassium hydroxide, arginine, cyclohexylamine, ethanolamine, diethanolamine and triethanolamine.

Some of the compounds of the general formulae II to V used as starting materials are known from the literature, or they are obtained by processes known per se from the literature (see Examples I to XLVIII).

As already mentioned at the outset, the compounds of the general formula I according to the invention, and their physiologically tolerated salts, have valuable pharmacological properties, in particular a specific inhibitory effect on signal transduction mediated by epidermal growth factor receptor (EGF-R), this possibly being brought about, for example, by inhibition of ligand binding, of receptor dimerization or of tyrosine kinase itself. It is additionally possible that the signal transmission is blocked at components located further downstream.

The biological properties of the novel compounds were tested as follows:

The inhibition of signal transmission mediated by EGF-R can be demonstrated, for example, using cells which express human EGF-R and whose survival and proliferation depend on stimulation by EGF or TGF-alpha. In this case, an interleukin-3 (IL-3)-dependent cell line of murine origin was used and was genetically modified in such a way that it expresses functional human EGF-R. Proliferation of these cells, which are called F/L-HERc, can therefore be stimulated either by murine IL-3 or by EGF (see von Rüden, T. et al. in EMBO J. 7, 2749–2756 (1988) and Pierce, J. H. et al. in Science 239, 620631 (1988)).

The starting material for the F/L-HERc cells was the cell line $FDC-P_1$ whose preparation has been described by Dexter, T. M. et al. in J. Exp. Med. 152, 1036–1047 (1980). However, it is also possible as an alternative to use other growth factor-dependent cells (see, for example, Pierce, J. H. et al. in Science 239, 628–631 (1988), Shibuya, H. et al. in Cell 70, 57–67 (1992) and Alexander, W. S. et al. in EMBO J. 10, 3683–3691 (1991)). Recombinant retroviruses as described in von Rüden, T. et al., EMBO J. 7, 2749–2756 (1988) Were used for expression of the human EGF-R cDNA (see Ullrich, A. et al. in Nature 309, 418–425 (1984)), with the difference that the retroviral vector LXSN (see Miller, A. D. et al. in BioTechniques 7, 980–990 (1989)) was employed for expression of the EGF-R cDNA, and the line GP+E86 (see Markowitz, D. et al. in J. Virol. 62, 1120–1124 (1988)) was used as packaging cell.

The test was carried out as follows:

F/L-HERc cells were cultivated in RPMI/1640 medium (BioWhittaker), supplemented with 10% fetal calf serum (FCS, Boehringer Mannheim), 2 mM glutamine (BioWhittaker), standard antibiotics and 20 ng/ml human EGF (Promega), at 37° C. and 5% $CO_2$. To investigate the inhibitor activity of the compounds according to the invention, $1.5 \times 10^4$ cells were cultivated in the above medium (200 µl) per well in triplicates in 96-well plates, stimulating proliferation of the cells either with EGF (20 ng/ml) or with murine IL-3. The source used for IL-3 was culture supernatants from the cell line X63/0 mIL-3 (see Karasuyama, H. et al. in Eur. J. Immunol. 18, 97–104 (1988)). The compounds according to the invention were dissolved in 100% dimethyl sulphoxide (DMSO) and added in various dilutions to the cultures, with the maximum DMSO concentration being 1%. The cultures were incubated at 37° C. for 48 hours.

To determine the inhibitory activity of the compounds according to the invention, the relative cell count was measured in O.D. units using the Cell Titre 96™ AQueous Non-Radioactive Cell Proliferation Assay (Promega). The relative cell count was calculated as a percent of the control (F/L-HERc cells without inhibitor), and the concentration of active substance which inhibits the proliferation of the cells by 50% (IC50) was inferred. The following results were obtained in this:

| Compound (Example No.) | Inhibition of EGF-dependent proliferation $IC_{50}$ [nM] | Inhibition of IL-3-dependent proliferation $IC_{50}$ [µM] |
| --- | --- | --- |
| 1 | 200 | >10 |
| 1(1) | 34 | >10 |
| 1(2) | 44 | >10 |
| 1(3) | 67 | >1 |
| 1(4) | 15 | >10 |
| 1(5) | 21 | >10 |
| 1(6) | 123 | >10 |
| 1(7) | 8 | >1 |
| 1(8) | 3 | >10 |
| 1(9) | 18 | >10 |
| 1(10) | 17 | >10 |
| 1(11) | 75 | >10 |
| 1(12) | 375 | >10 |
| 1(13) | 150 | >10 |
| 1(14) | 28 | >10 |
| 1(15) | 15 | >10 |
| 1(16) | 20 | >1 |
| 1(17) | 1 | >1 |
| 1(18) | 3 | >1 |
| 1(19) | 83 | >1 |
| 1(20) | 225 | >1 |
| 1(21) | 300 | >1 |
| 1(22) | 43 | >1 |
| 1(23) | 63 | >1 |
| 1(24) | 9 | >1 |
| 1(25) | 28 | >20 |
| 1(26) | 200 | >20 |
| 1(27) | 40 | >10 |
| 1(28) | 14 | 10 |
| 1(29) | 13 | >20 |
| 1(30) | 125 | >20 |
| 1(31) | 103 | 10 |
| 1(32) | >1000 | >20 |
| 1(33) | >1000 | >20 |
| 1(35) | 240 | >1 |
| 1(36) | 140 | >1 |
| 1(38) | 51 | >1 |
| 1(41) | 200 | >1 |
| 1(42) | >100 | >1 |
| 1(46) | 2 | >1 |
| 1(47) | >100 | >1 |
| 1(48) | 36 | >1 |
| 1(49) | >1000 | >1 |
| 1(50) | 3 | >1 |
| 1(51) | 9 | >1 |
| 1(52) | 10 | >1 |
| 1(53) | >100 | >1 |
| 1(54) | 10 | >1 |
| 1(55) | 40 | >1 |
| 1(56) | 40 | >1 |
| 1(57) | 88 | >10 |
| 1(58) | 4 | >1 |
| 1(59) | 1 | >1 |
| 1(60) | 120 | >10 |
| 1(61) | 50 | >1 |
| 1(62) | 4 | >10 |
| 1(63) | >10000 | >10 |
| 1(64) | 150 | >10 |

The compounds according to the invention also inhibit EGF-stimulated proliferation of the human tumour cell line KB which originates from an oral epidermoid carcinoma and overexpresses the EGF receptor (for example Aboud-Pirak, E. et al, J. Natl. Cancer. Inst. 80, 1605–11 (1988)). KB cells (purchased from ATCC) were passaged in DMEM (BioWhittaker) in the presence of 10% FCS (Boehringer Mannheim), 50 µM beta-mercaptoethanol and standard antibiotics. The EGF-induced DNA synthesis was determined by measuring the incorporation of radioactively labelled thymidine as indicator of EGF/TGF-alpha-stimulated cell proliferation. To do this, the cells were washed twice and 1500 cells per well were plated out in a 96-well plate in 200 µl of IMDM (BioWhittaker) without serum in the presence of 50 µM beta-mercaptoethanol, standard antibiotics, TGF-alpha [10 ng/ml] or EGF [20 ng/ml] and of various concentrations of the substances according to the invention (triplicates, maximum DMSO concentration 1%, see proliferation t t with F/L-HERc cells). After 60 hours, [$^3$H]-thymidine (0.1 µCi in 10 µl) was added for about 16–18 h. Subsequent measurement of thymidine incorporation revealed IC$_{50}$ values of 0.1–1 μM for compounds 4, 7, 8, 16, 17, 18, 19, 20, 21 and 22 Example 1, for the inhibition of EGF/TGF-alpha-stimulated KB cell proliferation.

The compounds of the general formula I according to the invention thus inhibit signal transduction by tyrosine kinases, as has been shown by the example of the human EGF receptor, and can therefore be used to treat pathophysiological processes caused by hyperactivity of tyrosine kinases. Examples of these are benign or malignant tumours, in particular tumours of epithelial and neuroepithelial origin, metastasis and abnormal proliferation of vascular endothelial cells (neoangiogenesis).

In addition, the compounds of the general formula I and their physiologically tolerated salts can be used to treat other disorders caused by aberrant activity of tyrosine kinases, such as, for example, epidermal hyperproliferation (psoriasis), inflammatory processes, disorders of the immune system, hyperproliferation of haematopoietic cells etc.

Because of their biological properties, the compounds according to the invention can be used alone or in combination with other pharmacologically active compounds, for example in tumour therapy as monotherapy or in combination with other antitumour therapeutics, for example in combination with topoisomerase inhibitors (for example etoposides), mitosis inhibitors (for example vinblastine), compounds which interact with nucleic acids (for example cis-platin, cyclophosphamide, adriamycin), hormone antagonists (for example tamoxifen), inhibitors of metabolic processes, (for example 5-FU etc.), cytokines (for example interferons), antibodies etc. These combinations can be administered either simultaneously or sequentially.

For pharmaceutical use, the compounds according to the invention are, as a rule, used in dosages of 0.01–100 mg/kg of body weight, preferably 0.1–15 mg/kg, for warm-blooded vertebrates, in particular humans. For administration, they are incorporated with one or more conventional inert excipients and/or diluents, for example with maize starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carbQxymethylcellulose or fat-containing substances such as hard fat or suitable mixtures thereof in conventional pharmaceutical preparations such as tablets, coated tablets, capsules, powders, suspensions, solutions, sprays or suppositories.

The following examples are intended to illustrate the present invention in detail without restricting it:

EXAMPLE I

4-Hydroxy-6-methylsulphinyl-pyrimido[5,4-d]pyrimidine and 4-Hydroxy-6-methylsulphonyl-pyrimido[5,4-d]pyrimidine 2.0 g of 4-hydroxy-6-methylthiopyrimido[5,4-d]pyrimidine and 8 g of 3-chloroperoxybenzoic acid (content: 50%) are stirred vigorously in 50 ml of methylene chloride for 3 hours. The precipitate is filtered off with suction, washed with ethyl acetate and dried.

Yield: 2.2 g, R$_f$: 0.27 and 0.50 (silica gel; methylene chloride/ethyl acetate/methanol=10:4:3)

EXAMPLE II

4-Hydroxy-6-(morpholino)-pyrimido[5,4-d]pyrimidine 16 g of a mixture of 4-hydroxy-6-methylsulphinylpyrimido-[5,4-d]pyrimidine and 4-hydroxy-6-methylsulphonylpyrimido-[5,4-d]pyrimidine in 25 ml of morpholine are heated at 135° C. (bath temperature) for 4 hours. After cooling and concentration, the residue is triturated with water, and the solid is filtered off with suction, washed with water and dried.

Yield: 7.8 g,; Melting point: >240° C.; R$_f$: 0.60 (silica gel; methylene chloride/ethyl acetate/methanol=10:4:3)

EXAMPLE III

4-Chloro-6-(morpholino)pyrimido[5,4-d]pyrimidine 7.8 g of 4-hydroxy-6-(morpholino)pyrimido[5,4-d]pyrimidine are heated under reflux with 100 ml of thionyl chloride with the addition of 4 drops of dimethyl formamide for 1.5 hours. The reaction mixture is concentrated and, after addition of methylene chloride, concentrated once again. The residue is then partitioned between methylene chloride and an aqueous potassium carbonate solution. The aqueous phase is extracted twice more with methylene chloride, and the combined organic phases are dried over magnesium sulphate and concentrated. The residue is triturated with diethyl ether and filtered off with suction.

Yield: 8.0 g (90% of theory), Melting point: 238°–240° C. (decomposition); R$_F$: 0.60 (silica gel; petroleum ether/ethyl acetate=2:1); Calculated: C 63.49 H 4.76 N 27.28 Found: 63.39 4.80 27.00

The following compound is obtained in analogy to Example III:
(1) 4-Chloro-6-methylthiopyrimido[5,4-d]pyrimidine Melting point: 90°–92° C.; R$_F$: 0.63 (silica gel; petroleum ether/ethyl acectate=7:3

EXAMPLE IV

5-Amino-2-methylthiopyrimidine-4-carboxylic acid 131.4 g of 5-bromo-2-methylthiopyrimidine-4-carboxylic acid, 860 ml of concentrated aqueous ammonia and 2.42 g of copper(II) sulphate dissolved in 34 ml of water are shaken in a pressure vessel at 95° C. for 4 hours. After cooling, the precipitate is filtered off with suction. The precipitate is dissolved in 600 ml of hot water, and the solution is filtered through active carbon. The filtrate is cooled in an ice bath and adjusted to pH 3 with concentrated hydrochloric acid. The precipitate is filtered off with suction and purified by dissolving in dilute sodium hydroxide solution and precipitating with hydrochloric acid.

Yield: 54.6 g (56% of theory),; Melting point: 187° C.; R$_f$: 0.35 (silica gel; ethyl acetate/methanol=2:1

EXAMPLE V

4-Hydroxy-6-methylthiopyrimido[5,4-d]pyrimidine 25 g of 5-amino-2-methylthiopyrimidine-4-carboxylic acid and 150 ml of formamide are stirred in an oil bath, with the temperature of the oil bath being increased to 180° C. over the course of half an hour. Stirring is continued at this temperature for 1.5 hours. The reaction mixture is then added hot to 750 ml of an ice/water mixture. After 2 hours, the product is filtered off with suction, washed with water and dried.

Melting point: >240° C.; R$_f$: 0.63 (silica gel; methylene chloride/ethyl acetate/methanol=10:4:3)

EXAMPLE VI

4-Hydroxy-6-methylthiopyrimido[5,4-d]pyrimidine

A mixture of 69 g of 5-amino-2-methylthiopyrimidine-4-carboxylic acid, 155 g of formamidine acetate and 300 ml of ethoxy ethanol is heated to boiling for 2 hours. The reaction mixture is then cooled to 10° C., 250 ml of water are added, and the mixture is left to stand at 10° C. for one hour. It is then filtered with suction, washed with water and dried.

Yield: 59 g (82% of theory),; Melting point: >240° C.; $R_f$: 0.63 (silica gel; methylene chloride/ethyl acetate/methanol=10:4:3)

EXAMPLE VII 3-(Aminocarbonylmethyl)piperidine 16.8 g of ethyl-3-pyridylacetate and 1 l of methanolic ammonia solution are shaken in a pressure vessel at 100° C. for 40 hours. After cooling and concentration, the precipitate is triturated with ether and filtered off with suction. 12.7 g of the 3-(aminocarbonylmethyl)pyridine obtained in this way are hydrogenated with 250 ml of ethanol and 3 g of rhodium/platinum catalyst at 50° C. under a pressure of 3 bar of hydrogen for 2 hours. After cooling, filtration and concentration, the precipitate is triturated with ether and filtered off with suction.

Yield 13.3 g (96% of theory),; $R_f$: 0.15 (silica gel; methylene chloride/methanol/concentrated ammonia=16:4:1)

EXAMPLE VIII 3-(4-Aminophenyl)propionic acid 15 g of palladium on carbon (10% and 30 ml of water are added to a mixture of 155 g of 4-nitrocinnamic acid in 1 l of methanol, and hydrogenation is carried out at room temperature under 3 bar until no further hydrogen is taken up, after about 2 hours. After filtration and evaporation of the solvent in a rotary evaporator, residual water is removed by twice adding 300 ml portions of toluene and distilling off the solvent in a rotary evaporator.

Yield: 132 g (100% of theory),; Melting point: 124°–128° C.

EXAMPLE IX 3-(trans-4-Acetylaminocyclohexyl)propionic acid

A mixture of 397 g of 3-(4-aminophenyl)propionic acid, 125 g of sodium hydroxide and 160 g of Raney nickel in 5.7 l of water is hydrogenated at 170° C. under 100 bar until no further hydrogen is taken up, after about 30 hours. Filtration and washing of the residue with water result in a filtrate in the form of 6.3 l of a colourless solution, to which a solution of 192 g of sodium hydroxide in 400 ml of water is added and then, dropwise, 454 ml of acetic anhydride over the course of 35 minutes. After five hours, the precipitate is filtered off, and the filtrate is adjusted to pH 4 by adding concentrated hydrochloric acid and is stirred at 0° C. for three hours. The product is then filtered off with suction, washed with 250 ml of ice-water and dried at 70° C.

Yield: 216 g (42% of theory),; Melting point: 193°–196° C.

EXAMPLE X

Methyl 3-(trans-4-aminocyclohexyl)propionate hydrochloride

A mixture of 185 g of 3-(trans-4-acetylaminocyclohexyl)-propionic acid, 500 ml of water and 500 ml of concentrated hydrochloric acid is heated to boiling for 68 hours. It is then evaporated to dryness in a rotary evaporator, and 300 ml portions of a methanol/toluene (2:1) mixture are added five times, again evaporating each time. The residue is stirred with 450 ml of an qcetone/tert-butyl methyl ether (1:2) mixure, filtered off with suction and dried over sodium hydroxide in vacuo. To complete the esterification, the solid is dissolved in 1 l of methanol and, while cooling in ice, 50 ml of thionyl chloride are added dropwise. After 30 minutes, the solvent is distilled off in a rotary evaporator, and the residue is with 300 ml of methanol and again evaporated. The residue is stirred with 450 ml of an acetone/tert-butyl/methyl etther (1:2) mixture, filtered off with suction and dried.

Yield: 178 g (92% of theory),; Melting point 196°–198° C.

EXAMPLE XI

4-Amino-2,6-dibromoaniline 20 g of 2,6-Dibromo-4-nitroaniline are taken up in 250 ml of ethanol, 250 ml of ethyl acetate, 100 ml of dimethylformamide and 90 ml of methylene chloride and, after addition of 3.3 g of 5% moist platinum/active carbon catalyst, hydrogenated at room temperature under 50 psi for one hour. The solvent is then distilled off in a rotary evaporator, and the residue is triturated with diethyl ether, filtered off with suction and washed several times with petroleum ether.

Yield: 8 g (45% of theory),; Melting point: 127°–132° C.; $R_f$: 0.59 (silica gel; petroleum ether/ethyl acetate=10:5)

EXAMPLE XIII

4-Amino-1-tert-butyloxycarbonylpiperidine 22 g of di-tert-butyl dicarbonate and 14 ml of triethylamine are added to 10 g of 4-aminopiperidine in 120 ml of a dioxane/water (1:1) mixture at 0° C., and the mixture is stirred at room temperature for 12 hours. The dioxane is then distilled off in a rotary evaporator, and the aqueous phase is extracted six times with ethyl acetate. The combined organic phases are dried over magnesium sulphate, and the solvent is distilled off in a rotary evaporator. The residue slowly crystallizes.

Yield: 16 g (80% of theory),; Melting point: 47°–52° C.; $R_F$: 0.69 (alumina; mrthylene chlorid/methanol=9:1)

The following compounds are obtained in analogy to Example XII:

(1) 1-tert-Butyloxycarbonylamino-2-methyl-2-propylamine Prepared from 1,2-diamino-2-methylpropane.

Yellow oil; $R_f$: 0.45 (alumina; methylene chloride/methanol=20:1)

(2) 3-Aminocarbonyl-1-tert-butyloxycarbonylpiperidine Melting point: 171°–177° C.; $R_f$: 0.50 (alumina; methylene choloide/methanol=10:0.8)

EXAMPLE XIII

4-Aminomethyl-1-tert-butyloxycarbonylpiperidine 19 g of di-tert-butyl dicarbonate and 12 ml of triethylamine are added to 10 g of 4-aminomethylpiperidine in 120 ml of a dioxane/water (1:1) mixture at 0° C. and the mixture is stirred at room temperature for 12 hours. The dioxane is then distilled off in a rotary evaporator, and the aqueous phase is extracted six times with ethyl acetate. The combined organic phases are dried over magnesium sulphate, and the solvent is distilled off in a rotary evaporator. The residue is purified by chromatography on an alumina column with methylene chloride/methanol=50:1.

Yield: 7.4 g (39% of theory),; $R_f$: 0.48 (alumina; methylene chlorid/methanol=10:1)

The following compound is obtained in analogy to Example XIII:

(1) 4-Amino-1-tert-butyloxycarbonylazacycloheptane colourless oil; $R_F$: 0.36 (alumina; methylene chloride/methanol=9:1)

EXAMPLE XIV

3-Aminomethylpiperidine 7 g of piperidine-3-carboxamide in 30 ml of tetrahydrofuran are added dropwise in portions to 8 g of lithium aluminium hydride in 250 ml of tetrahydrofuran while stirring at room temperature. The mixture is then heated to boiling for 10 hours. It is cooled to 0° C., and 10% strength potassium hydroxide solution is cautiously added dropwise until a white precipitate has formed. After decantation, the precipitate is washed four times by addition of 50 ml of tetrahydrofuran and decantation each time. The organic phases are combined, the solvent is distilled off in a rotary evaporator, and the residue is puritied by column chromatography on alumina with a methylene chloride/methanol (16:1) mixture.

Yield: 4.8 g (77% of theory) as colourless oil.

The following compound is obtained in analogy to Example XIV:
(1) 4-Aminomethylquinuclidine Colourless oil; $R_f$: 0.3 (trace of tailing; alumina; methylene chloride/methanol=7:3); Mass spectrum: M+=140; Prepared from 4-cyanoquinuclidine (see Example 3 of EP-A-0,213,337).

EXAMPLE XV

Trans-4-tert-butyloxycarbonylaminomethylcyclohexane carboxylic acid 4.6 g of trans-4-aminomethylcyclohexane carboxylic acid are dissolved in 65 ml of 1N sodium hydroxide solution, and 6.6 g of di-tert-butyl dicarbonate in 50 ml of tetrahydrofuran are added. After 12 hours, the mixture is extracted six times with ethyl acetate. The combined organic phases are washed successively with 2N citric acid solution and saturated sodium chloride solution and dried over magnesium sulphate, and the solvent is distilled off in a rotary evaporator. The residue is dried under 0.1 torr.

Yield: 6.5 g (87% of theory),; Melting point: 137°–140° C.

EXAMPLE XVI trans-4-(tert-Butyloxycarbonylaminomethyl) benzyloxycarbonyl-amino cyclohexane 5.5 g of trans-4-tert-butyloxycarbonylaminomethylcyclohexane carboxylic acid are dissolved in 250 ml of dioxane and, after addition of 6.5 ml of triethylamine and 5.6 ml of diphenylphosphoryl azide, heated at 130° C. for 1.5 hours. Then 8.7 ml of benzyl alcohol are added and heating to boiling is continued for 14 hours. After cooling, the dioxane is distilled off in a rotary evaporator, the residue is taken up in ethyl acetate, washed with saturated sodium chloride solution and dried over magnesium sulphate, and the solvent is distilled off in a rotary evaporator. The residue is triturated with petroleum etber/ether (5:1), filtered off with suction and dried.

Yield: 6.6 g (86% of theory); Melting point: 117°–122° C.

EXAMPLE XVII trans-4-(Aminomethyl) benzyloxycarbonylaminocyclohexane 1.3 g of trans-4-(tert-butyloxycarbonylaminomethyl)-benzyloxycarbonylaminocyclohexane are dissolved in 50 ml of methylene chloride, and 5 ml of trifluoroacetic acid are added. After 1 hour, 33 ml of 2N sodium hydroxide solution are added dropwise. After phase separation, the aqueous phase is extracted three times more with methylene chloride, the combined organic phases are dried over magnesium sulphate, and the solvent is distilled off in a rotary evaporator. The residue is employed without further purification.

Yield: 870 mg (93% of theory) of a colourless wax,; $R_f$: 70.15 (alumina; methylene chloride/methanol=20:1)

EXAMPLE XVIII trans-4-Amino-(tert-butyloxycarbonylaminomethyl) cyclohexane 1.4 g of trans-4-(tert-butyloxycarbonylaminomethyl)-benzyloxycarbonylaminocyclohexane are dissolved in 30 ml of methanol and, after addition of 0.3 g of palladium/active carbon catalyst, hydrogenated at room temperature under 50 psi for one hour. After filtration, the solvent is distilled off in a rotary evaporator. The residue is employed without purification. P Yield: 1.02 g (100% of theory) of a colourless wax,; $R_f$: 0.28 (alumina; -methylene chloride/methanol= 10:1)

EXAMPLE XIX

1-Benzylazacycloheptan-4-one oxime 7.2 g of 1-benzylazacycloheptan-4-one are added to a solution of 3.1 g of hydroxylamine hydrochloride and 2.9 g of sodium acetate in 30 ml of water at 60° C. After 2 hours, the mixture is cooled and made alkaline with 2N sodium hydroxide solution. The mixture is extracted four times with diethyl ether, the organic phases are washed with saturated sodium chloride solution and dried over magnesium sulphate, and the solvent is distilled off in a rotary evaporator. The residue is triturated with petroleum ether, filtered off with suction and employed without further purification.

Yield: 5.9 g (90% of theory),; Melting point: 73°–76° C.; $R_f$: 0.16 (alumina; petroleum ether/ethyl acetate=1:1)

EXAMPLE XX

4-Amino-1-benzylazacycloheptane 2.18 g of 1-benzylazacycloheptan-4-one oxime are dissolved in 30 ml of tetrahydrofuran and 2 ml of concentrated ammonia solution and, after addition of 0.9 g of Raney nickel, hydrogenated at room temperature under 50 psi for 12 hours. After filtration, the solvent is distilled off in a rotary evaporator. Water is added to the residue, the mixture is extracted three times with methylene chloride, the organic phase is dried over magnesium sulphate, and the solvent is distilled off in a rotary evaporator. The residue is purified by column chromatography on alumina with a methylene chloride/methanol (30:1) mixture.

Yield: 1.55 g (76% of theory) as colourless oil,; $R_f$: 0.43 (alumina; methylene chloride/methanol=9:1)

EXAMPLE XXI

4-Aminoazacycloheptane 13.4 g of 4-amino-1-benzylazacycloheptane are dissolved in 200 ml of methanol and, after addition of 10 g of palladium dihydroxide, hydrogenated at room temperature under 50 psi for one hour. After filtration, the solvent is distilled off in a rotary evaporator. The residue is distilled under 0.7 torr.

Yield: 7.6 g (100% of theory) as colourless oil,; Boiling point: 43° C. under 0.7 torr.

EXAMPLE XXII 4-(N-Methyl-N-acetylamino)aminocyclohexane 2.5 g of 4-(N-methyl-N-acetylamino)aniline are dissolved in 50 ml of methanol and 15 ml of 1N hydrochloric acid and, after addition of 2 g of rhodium/active carbon, hydrogenated at 70° C. under 50 psi for eight hours. After filtration, the solvent is distilled off in a rotary evaporator. The residue is made alkaline with 50% strength sodium hydroxide solution, the mixture is extracted three times with methylene chloride, the organic phase is dried over magnesium sulphate, and the solvent is distilled off in a rotary evaporator. The residue is purified by column chromatography on silica gel with a methylene chloride/ethyl acetate/methanol (10:4:3) mixture.

Yield: 0.7 g (28% of theory) as colourless oiL,; $R_f$: 0.40 (alumina; methylene chloride/ethyl acetate/methanol= 10:4:3)

EXAMPLE XXIII

4-Tetrahydropyranone oxime 5.0 g of 4-tetrahydropyranone are added dropwise to a stirred mixture of 5.2 g of hydroxylamine hydrochloride and 4.8 g of sodium acetate in 50 ml of water at 60° C. After a further hour at 60° C., the solution is allowed to cool and is extracted three times with 50 ml of ether each time. The combined organic phases are then dried over sodium sulphate, the solvent is distilled off in a rotary evaporator, and the residue is employed without further purification in the next reaction.

Yield: 4.2 g (74% of theory),; Melting point: 50°–52° C.; $R_f$: 0.30 (silica gel; petroleum ether/ethyl acetate=1:1)

EXAMPLE XXIV

4-Aminotetrahydropyran 4.2 g of 4-tetrahydropyranone oxime are dissolved in 100 ml of ethanol and, after addition of 0.5 g of palladium on carbon (10%), hydrogenated in a Parr apparatus at 90° C. under a pressure of 5 bar of hydrogen for 2.5 hours. After cooling, the solvent is distilled off in a rotary evaporator, and the residue is used further without further purification.

Yield: 0.7 g (19% of theory) of a colourless oil,; $R_f$: 0.45 (silica gel; methylene chloride/ethyl acetate/methanol= 10:4:2)

EXAMPLE XXV 1-(2-Benzylideneaminoethyl)piperazine 12.9 g of 1-(2-aminoethyl)piperazine and 10.6 g of benzaldehyde in 125 ml of toluene are heated to boiling with a water trap until no more water separates out, after about 4 hours. After cooling, the solvent is distilled off in a rotary evaporator, and the residue is used further without further purification.

Yield: 21.7 g (100% of theory) of a pale brownish oil,; $R_f$: 0.70 (silica gel; methylene chloride/methanol=10.1)

EXAMPLE XXVI

Ethyl N-benzyl-3-methyl-4-piperidone-3-carboxylate 4.2 g of potassium tert-butoxide and 2.1 g of methyl iodide are added to 8.88 g of ethyl N-benzyl-4-piperidone-3-carboxylate in 30 ml of tetrahydrofuran while cooling in ice. After 12 hours at room temperature, the mixture is filtered, the residue is washed with tetrahydrofuran, and the combined filtrates are freed of solvent in a rotary evaporator. The remaining oil is purified by column chromatography on silica gel with methylene chloride.

Yield: 3.41 g (36% of theory) of a yellow oil,; $R_f$: 0.80 (silica gel, methylene chloride/methanol=50:1)

EXAMPLE XXVII

N-Benzyl-3-methyl-4-piperidone 3.29 g of ethyl N-benzyl-3-methyl-4-piperidone-3-carboxylate are heated to boiling in 20 ml of 6N hydrochloric acid for eight hours. After cooling, 200 ml of methylene chloride are added and, while cooling in ice, the mixture is made alkaline with 15% strength sodium hydroxide solution. The solution is extracted three times with 50 ml of methylene chloride each time. The combined organic phases are then dried over sodium sulphate, the solvent is distilled off in a rotary evaporator, and the residue is used further without further purification.

Yield: 2.26 g (93% of theory) of a pale brown oil,; $R_f$: 0.70 (silica gel; methylene chloride/methanol=20:1)

EXAMPLE XXVIII cis- and trans-1-Benzyl-4-benzylamino-3-methylpiperidine 9.94 g of N-benzyl-3-methyl-4-piperidone, 5.4 ml of benzylamine, 90 ml of toluene and 10 g of molecular sieves (4A) are stirred at room temperature for 12 hours and then filtered, and the solvent is distilled off in a rotary evaporator. The residue is dissolved in 50 ml of methanol and, while cooling in ice, 0.55 g of sodium boranate is added. After 5 hours at room temperature, the solvent is distilled off in a rotary evaporator, methylene chloride and ice-water are added to the residue, and the mixture is adjusted to pH 5 with citric acid. The phases are shaken thoroughly and then separated, and the aqueous phase is made alkaline with sodium hydroxide solution and extracted three times with methylene chloride. The combined organic phases are then dried over sodium sulphate, the solvent is distilled off in a rotary evaporator, and the residue is purified by column chromatography on silica gel with a methylene chloride/methanol/concentrated ammonia (firstly 98:2:0.8, then 95:5:0.8) mixture. This separates the isomers. Besides 3 g of a mixture of the two isomers, the following are obtained:

Yield: 4.0 g (27% of theory) of a yellow oil of the cis isomer,; $R_f$: 0.90 (silica gel; methylene chloride/methanol/concentrated ammonia=98:2:2)

Yield: 1.5 g (10% of theory) of a yellow oil of the trans isomer,; $R_f$: 0.45 (silica gel; methylene chloride /methanol/concentrated ammonia=98:2:2)

EXAMPLE XXIX cis-4-Amino-3-methylpiperidine 3.8 g of cis-1-benzyl-4-benzylamino-3-methylpiperidine are dissolved in 30 ml of methanol and 25 ml of 1N hydrochloric acid and, after addition of 1.5 g of palladium dihydroxide, hydrogenated at 50° C. under 3 bar for 10 hours. After filtration, the solvent is distilled off in a rotary evaporator. 15% strength sodium hydroxide solution is added to the residue, which is extracted three times with diethyl ether. The combined organic phases are then dried over sodium sulphate, and the solvent is distilled off in a rotary evaporator. The residue is used further without further purification.

Yield: 1.1 g (72% of theory) as colourless oil.

The following compound is obtained in analogy to Example XXIX:

(1) trans-4-Amino-3-methylpiperidine

Prepared from trans-1-benzyl-4-benzylamino-3-methylpiperidine

EXAMPLE XXX

4-[(3-Chloro-4-fluorophenyl)amino]-6-methylthiopyrimido[5,4-d]pyrimidine 3.0 g of 4-chloro-6-methylthiopyrimido[5,4-d]pyrimidine, 3.8 g of 3-chloro-4-fluoroaniline and 10 ml of dioxane are heated at 80° C. for 2 hours. After cooling, the reaction mixture is concentrated and portions are triturated first with water and then with diethyl ether, filtered off with suction and dried.

Yield: 4.0 g (91% of theory),; Melting point: 144°–148° C.; $R_f$: 0.50 (silica gel; petroleum ether/ethyl acetate=1:1)

EXAMPLE XXXI

4-[(3-Chloro-4-fluorophenyl)amino]-6-methylthiopyrimido[5,4-d]pyrimidine 148 g of 4-hydroxy-6-methylthiopyrimido[5,4-d]pyrimidine, 286 ml of hexamethyldisilazane, 333 g of 3-chloro-4-fluoroaniline and 15 g of p-toluenesulphonic acid are heated at 140° C. for 23 hours. The reaction mixture is cooled and, after addition of 4 l of methanol, heated at 100° C. for one hour. The methanol is distilled off and the residue is triturated three times with diethyl ether and filtered off with suction.

Yield: 202 g (82% of theory), Melting point: 144°–148° C.; $R_f$: 0.50 (silica gel; petroleum ether/ethyl acetate=1:1)

The following compounds are obtained in analogy to Examples XXX and XXXI:

(1) 4-[(3-Methylphenyl)amino]-6-methylthiopyrimido[5,4-d]-pyrimidine Melting point: 118°–120° C.; $R_f$: 0.55 (silica gel; petroleum ether/ethyl acetate=2:1)

(2) 4-[(4-Amino-3,5-dichlorophenyl)amino]-6-methylthiopyrimido[5,4-d]pyrimidine

Melting point: 195°–197° C.; $R_f$: 0.50 (silica gel; petroleum ether/ethyl acetate=1:1)

(3) 4-[(4-Amino-3-bromo-5-chlorophenyl)amino]-6-methylthiopyrimido[5,4-d]pyrimidine Melting point: 210°–212° C.; $R_f$: 0.31 (silica gel; petroleum ether/ethyl acetate=1:1)

(4) 4-[(4-Amino-3,5-dibromophenyl)amino]-6-methylthiopyrimido[5,4-d]pyrieidine

Melting point: 245°–247° C.; $R_f$: 0.35 (silica gel; petroleum ether/ethyl acetate=1:1)

(5) 4-[(3-(1,1,2,2-Tetrafluoroethoxy)phenyl)amino]-6-methylthiopyrimido[5,4-d]pyrimidine Melting point: 129°–130° C.; $R_f$: 0.55 (silica gel; petroleum ether/ethyl acetate=2:1)

(6) 4-[(4-Benzylphenyl)amino]-6-methylthiopyrimido[5,4-d]pyrimidine

Melting point: 197°–199° C.; $R_f$: 0.65 (silica gel; petroleum ether/ethyl acetate=2:1)

(7) 4-[(3-Benzyloxyphenyl)amino]-6-methylthiopyrimido[5,4-d]pyrimidine $R_f$: 0.80 (silica gel; petroleum ether)

(8) 4-[(3-HydroxyTnethylphenyl)amino]-6-methylthiopyrimido[5,4-d]pyrimidine

Melting point: 164°–166° C.; $R_f$: 0.55 (silica gel; petroleum ether/ethyl acetate=2:1)

(9) 4-[4-Biphenylylamino]-6-methylthiopyrimido[5,4-d]pyrimidine

Melting point: 200°–202° C.; $R_f$: 0.45 (silica gel; petroleum ether/ethyl acetate=1:1)

(10) 4-[3-Phenoxyphenylamino]-6-methylthiopyrimido[5,4-d]pyrimidine

Melting point: 140°–142° C.; $R_f$: 0.40 (silica gel; petroleum ether/ethyl acetate=2:1)

(11) 4-[3-Ethynylphenylamino]-6-methylthiopyrimido[5,4-d]pyrimidine

Melting point: 160°–163° C.; $R_f$: 0.39 (silica gel; petroleum ether/ethyl acetate=2:1)

(12) 4-[3,4-Difluorophenylamino]-6-methylthiopyrimido[5,4-d]pyrimidine

Melting point: 175°–178° C.; $R_f$: 0.45 (silica gel; petroleum ether/ethyl acetate=10:6)

(13) 4-[3-Cyanophenylamino]-6-methylthiopyrimido[5,4-d]pyrimidine

Melting point: 240°–244° C.; $R_f$: 0.52 (silica gel; petroleum ether/ethyl acetate=10:6)

(14) 4-[3-Trifluoromethoxyphenylamino]-6-methylthiopyrimido[5,4-d]pyrimidine

Melting point: 114°–116° C.; $R_f$: 0.56 (silica gel; petroleum ether/ethyl acetate=10:5)

(15) 4-[3-Nitrophenylamino]-6-methylthiopyrimido[5,4-d]pyrimidine

Melting point: 194°–197° C.; $R_f$: 0.30 (silica gel; petroleum ether/ethyl acetate=10:5)

(16) 4-[4-Phenoxyphenylamino]-6-methylthiopyrimido[5,4-d]pyrimidine

Melting point: 191°–192° C.; $R_f$: 0.50 (silica gel; petroleum ether/ethyl acetate=10:5)

(17) 4-[4-Benzyloxyphenylamino]-6-methylthiopyrimido[5,4-d]pyrimidine

Melting point: 163° C.; $R_f$: 0.44 (silica gel; petroleum ether/ethyl acetate=10:5)

(18) 4-[3-Chloro-4-phenoxyphenylamino]-6-methylthiopyrimido[5,4-d]pyrimidine

Melting point: 169°–170° C.; $R_f$: 0.39 (silica gel; petroleum ether/ethyl acetate=10:5)

(19) 4-[4-Benzyloxy-3-chlorophenylamino]-6-methylthiopyrimido[5,4-d]pyrimidine

Melting point: 144°–146° C.; $R_f$: 0.55 (silica gel; petroleum ether/ethyl acetate=20:1)

EXAMPLE XXXII

4-[(3-Chloro-4-fluorophenyl)amino]-6-methylsulphinylpyrimido[5,4-d]pyrimidine and 4-[(3-chloro-4-fluorophenyl)amino]-6-methylsulphonylpyrimido[5,4-d]pyrimidine 4.0 g of 4-[(3-chloro-4-fluorophenyl)amino]-6-methylthiopyrimido[5,4-d]pyrimidine are dissolved in 100 ml of methylene chloride and 5 ml of methanol and, at room temperature, 8.0 g of 3-chloroperoxybenzoic acid (50% pure) are added in portions. After two hours, the mixture is washed twice with sodium bicarbonate solution, dried over magnesium sulphate and concentrated. The title compounds are obtained as a 1:1 mixture and employed further without further separation.

Yield: 4.2 g, Melting point of the mixture: 170° C. (decomposition); $R_f$: 0.10 and 0.28 (silica gel; petroleum ether/ethyl acetate=1:1)

EXAMPLE XXXIII

4-[(3-Chloro-4-fluorophenyl)amino]-6-methylsulphinylpyrimido[5,4-d]pyrimidine and 4-[(3-chloro-4-fluorophenyl)amino]-6-methylsulphonylpyrimido[5,4-d]pyrimidine 39.2 g of 4-[(3-chloro-4-fluorophenyl)amino]-6-methylthiopyrimido[5,4-d]pyrimidine are dissolved in 350 ml of glacial acetic acid and, at room temperature, 37 g of sodium perborate are added in portions over the course of four hours. After 24 hours, the mixture is poured into 1 l of water, and the precipitate is filtered off with suction and washed twice with water, once with sodium bicarbonate solution and twice again with water and dried. The product is a 10:1 mixture of sulphoxide and sulphonyl compounds and is employed further without further purification.

Yield: 38 g, $R_f$: 0.10 and 0.28 (silica gel; petroleum ether/ethyl acetate=1:1)

Melting point of the mixture: 140°–145° C. (decomposition)

The following compounds are obtained in analogy to Examples XXXII and XXXIII:

(1) 4-[(3-Methylphenyl)amino]-6-methylsulphinyl-pyrimido[5,4-d]pyrimidine and 4-[(3-methylphenyl)amino]-6-methylsulphonylpyrimido[5,4-d]pyrimidine $R_f$: 0.38 and 0.54 (silica gel; petroleum ether/ethyl acetate/methanol=10:10:1)

(2) 4-[(4-Amino-3,5-dichlorophenyl)amino]-6-methylsulpinylpyrimido[5,4-d]pyrimidine and 4-[(4-amino-3,5-dichlorophenyl)-amino]-6-methylsulphonylpyrimido[5,4-d]pyrimidine $R_f$: 0.40 and 0.51 (silica gel; petroleum ether/ethyl acetate/methanol=10:10:2)

(3) 4-[(4-Amino-3-bromo-5-chlorophenyl)amina]-6-methyisulphinylpyrimido[5,4-d]pyrimidine and 4-[(4-amino-3-bromo-5-chlorophenyl)amino]-6-methylsulphonylpyrimido[5,4-d]pyrimidine $R_f$: 0.28 and 0.40 (silica gel; petroleum ether/ethyl acetate/methanol=10:10:1)

(4) 4-[(4-Amino-3,5-dibromophenyl)amino]-6-methylsulphinylpyrimido[5,4-d]pyrimidine and 4-[(4-amino-4,5-dibromophenyl)amino]-6-methylsulphonylpyrimido[5,4-d]pyrimidine $R_f$: 0.51 and 0.68 (silica gel; petroleum ether/ethyl acetate/methanol=10:10:2)

(5) 4-[(3-(1,1,2,2-Tetrafluoroethoxy)phenyl)amino]-6-methylsulphinylpyrimido[5,4-d]pyrimidine and 4-[(3-(1,1,2,2-tetrafluoroethoxy)phenyl)amino]-6-methylsulphonylpyrimido[5,4-d]pyrimidine $R_f$: 0.32 and 0.80 (silica gel; petroleum ether/ethyl acetate/methanol=10:10:1)

(6) 4-[(4-Benzylphenyl)amino]-6-methylsulphinylpyrimido[5,4-d]pyrimidine and 4-[(4-benzylphenyl)amino]-6-methylsulphonylpyrimido[5,4-d]pyrimidine $R_f$: 0.20 and 0.58 (silica gel; petroleum ether/ethyl acetate/methanol=10:10:1)

(7) 4-[(3-Benzyloxyphenyl)amino]-6-methylsulphinylpyrimido[5,4-d]pyrimidine and 4-[(3-benzyloxyphenyl)amino]-6-methylsulphonylpyrimido[5,4-d]pyrimidine $R_f$: 0.40 (silica gel; petroleum ether/ethyl acetate=2:1)

(8) 4-[(3-Hydroxymethylphenyl)amino]-6-methylsulphinylpyrimido[5,4-d]pyrimidine and 4-[(3-hydroxymethylphenyl)amino]-6-methylsulphonylpyrimido[5,4-d]pyrimidine $R_f$: 0.15 and 0.40 (silica gel; petroleum ether/ethyl acetate methanol=10:10:1)

(9) 4-[4-Biphenylylamino]-6-methylsulphinylpyrimido[5,4-d]pyrimidine and 4-[4-biphenylylamino]-6-methylsulphonylpyrimido[5,4-d]pyrimidine $R_f$: 0.38 (silica gel; petroleum ether/ethyl acetate/methanol=10:10:1)

(10) 4-[3-Phenoxyphenylamino]-6-methyisulphinylpyrimido[5,4-d]pyrimidine and 4-[3-phenoxyphenylamino]-6-methylsulphonylpyrimido[5,4-d]pyrimidine $R_f$: 0.31 and 0.48 (silica gel; petroleum ether/ethyl acetate/methanol=10:10:1)

(11) 4-[3-Ethynylphenylamino]-6-methylsulphinylpyrimido[5,4-d]pyrimidine and 4-[3-ethynyl-phenylamino]-6-methylsulphonylpyrimido[5,4-d]pyrimidine Melting point: 160°–163° C.; $R_f$: 0.31 and 0.38 (silica gel; petroleum ether/ethyl acetate/methanol=10:10:1)

(12) 4-[3,4-Difluorophenylamino]-6-methylsulphinylpyrimido[5,4-d]pyrimidine and 4-[3,4-difluorophenylamino]-6-methylsulphonylpyrimido[5,4-d]pyrimidine Melting point: 169°–173° C.; $R_f$: 0.46 (silica gel; petroleum ether/ethyl acetate/methanol=10:10:2)

(13) 4-[3-Cyanophenylamino]-6-methylsulphinylpyrimido[5,4-d]pyrimidine and 4-[3-cyanophenylamino]-6-methylsulphonylpyrimido[5,4-d]pyrimidine Melting point: 222°–225° C.; $R_f$: 0.38 and 0.47 (silica gel; petroleum ether/ethyl acetate/methanol=10:8:2)

(14) 4-[3-Trifluoromethoxyphenylamino]-6-methylsulphinylpyrimido[5,4-d]pyrimidine and 4-[3-trifluoromethoxyphenylamino]-6-methylsulphonylpyrimido[5,4-d]pyrimidine Melting point: 95°–100° C.; $R_f$: 0.28 and 0.48 (alumina; petroleum ether/ethyl acetate/methanol=10:10:1)

(15) 4-[3-Nitrophenylamino]-6-methylsulphinylpyrimido[5,4-d]pyrimidine and 4-[3-nitrophenylamino]-6-methylsulphonylpyrimido[5,4-d]pyrimidine Melting point: 71° C. (decomposition); $R_f$: 0.44 and 0.53 (silica gel; petroleum ether/ethyl acetate/methanol=10:10:2)

(16) 4-[4-Phenoxyphenylamino]-6-methylsulphinylpyrimido[5,4-d]pyrimidine and 4-[4-phenoxyphenylamino]-6-methylsulphonylpyrimido[5,4-d]pyrimidine $R_f$: 0.28 and 0.41 (silica gel; petroleum ether/ethyl acetate/methanol=10:10:1)

(17) 4-[4-Benzyloxyphenylamino]-6-methylsulphinylpyrimido[5,4-d]pyrimidine and 4-[4-benzyloxyphenylamino]-6-methylsulphonylpyrimido[5,4-d]pyrimidine Melting point: 122°–130° C.; $R_f$: 0.35 and 0.48 (silica gel; petroleum ether/ethyl acetate/methanol=10:8:2)

(18) 4-[3-Chloro-4-phenoxyphenylamino]-6-methylsulphinylpyrimido[5,4-d]pyrimidine and 4-[3-chloro-4-phenoxyphenylamino]-6-methylsulphonylpyrimido[5,4-d]pyrimidine Melting point: 189°–190° C.; $R_f$: 0.55 and 0.70 (silica gel; petroleum ether/ethyl acetate/methanol=10:10:2)

(19) 4-[4-Benzyloxy-3-chlorophenylamino]-6-methylsulphinylpyrimido[5,4-d]pyrimidine and 4-[4-benzyloxy-3-chlorophenylamino]-6-methylsulphonylpyrimido[5,4-d]pyrimidine Melting point: 148°–150° C.; $R_f$: 0.28 and 0.50 (silica gel; petroleum ether/ethyl acetate/methanol=10:10:2)

EXAMPLE XXXIV

4-Hydroxymethylpiperidine

A solution of 3.1 g of ethyl piperidine-4-carboxylate in 50 ml of tetrahydrofuran is added dropwise to 1.5 g of lithium aluminium hydride in 50 ml of tetrahydrofuran at room temperature. The mixture is then heated to boiling for one hour. After cooling to 0° C., 10 ml of a 10% strength potassium hydroxide solution are added. The precipitate is filtered off and then washed twice with 20 ml of tetrahydrofuran each time.

The combined organic phases are evaporated, and the residue is purified by column chromatography on alumina with an ethyl acetate/methanol/concentrated ammonia mixture (10:5:0.05).

Yield: 2.2 g (100% of theory) as yellow oil; $R_f$: 0.50 (alumina; ethyl acetate/methanol/concentrated ammonia=10:5:0.05).

EXAMPLE XXXV endo-8-Benzyl-3-benzylamino-8-aza-bicyclo[3.2.1] octane 23 g of sodium triacetoxyborohydride are added in portions to a mixture of 17.8 g of N-benzyltropinone, 8.9 g of benzylamine, 4.8 ml of glacial acetic acid and 300 ml of absolute tetrahydrofuran at room temperature, and the mixture is stirred for 12 hours. The solvent is then distilled off in a rotary evaporator, sodium bicarbonate solution is added to the residue, and the mixture is extracted three times with ethyl acetate. The combined organic phases are then dried over sodium sulphate, and the solvent is distilled off in a rotary evaporator. A 7 g portion of the total residue of 25 g is purified by column chromatography on silica gel with methylene chloride/methanol/concentrated ammonia (30:1:0.1).

Yield: 3.1 g (43% of theory), $R_f$: 0.31 (silica gel; methylene chloride/methanol/concentrated ammonia=9:1:0.1); Melting point: 49°–51° C.

The following compound is obtained in analogy to Example XXXV:
(1) 8-Dimethylamino-1,4-dioxaspiro[4.5]decane Prepared from 1,4-dioxaspiro[4.5]decan-8-one and dimethylamine. Pale brown oil, $R_f$: 0.28 (silica gel; methylene chloroide/methanol/concentrated ammonia=9:1:0.1)

EXAMPLE XXXVI endo-3-Amino-8-azabicyclo[3.2.1]octane 3.1 g of endo-B-benzyl-3-benzylamino-8-aza-bicyclo [3.2.1]octane are dissolved in 100 ml of methanol and, after addition of 3 g of palladium hydroxide on carbon, hydrogenated at room temperature under 3 bar until no further hydrogen is taken off. The catalyst is then filtered off, the solvent is distilled off in a rotary evaporator, and the remaining oil is dried in vacuo. The product is used without further purification.

Yield: 1.28 g (100% of theory), $R_f$: 0.5 (alumina; methylene chloride/methanol/concentrated ammonia=6:1:0.1)

The following compounds are obtained in analogy to Example XXXVI:
(1) exo-3-Amino-8-azabicyclo[3.2.1]octane Prepared from the compound of Example XXXVIII. $R_f$: 0.17 (alumina; methylene chloride/methanol/concentrated ammonia=15:1:0.1)
(2) 4-amino-4-methylpiperidine Prepared from the compound of Example XL. $R_f$: 0.50 (alumina; methylene chloride/methanol/concentrated ammonia=9:1:0.1)

EXAMPLE XXXVII

N-Benzyltropinone oxime 10 g of N-benzyltropinone are added to a mixture of 4.9 g of hydroxylamine hydrochloride and 4.24 g of sodium acetate in 80 ml water it 60° C., and the mixture is stirred at 60° C. for 2 hours. The mixture is then made alkaline with anhydrous potassium carbonate and is extracted three times with methylene chloride. The combined organic phases are then dried over sodium sulphate, and the solvent is distilled off in a rotary evaporator. A few ml of ether are added to the remaining oil for crystallization; the solid is triturated with petrol ether and filtered off with suction.

Yield: 8.7 g (80% of theory), Melting point: 117°–119° C.; $R_f$: 0.19 (alumina; petroleum ether/ethyl acetate=1:1)

EXAMPLE XXXVIII exo-3-Amino-8-azabicyclo[3.2.1]octane

A solution of 5.35 g of N-benzyltropinone oxime in 100 ml of amyl alcohol is heated to boiling 3.2 g of sodium are added in portions over the course of 30 minutes, and the mixture is then boiled for a further two hours. After cooling it is acidified with 50% concentrated hydrochloric acid while cooling in ice, and is extracted twice with ethyl acetate. The aqueous phase is then made alkaline with 20% strength sodium hydroxide solution and extracted three times with ethyl acetate. The combined organic phases are then dried over potassium carbonate, and the solvent is distilled off in a rotary evaporator. The residue is purified by column chromatography on alumina with a petroleum ether/ethyl acetate/methanol (10:5:1) mixture.

Yield: 2.72 g (55% of theory) as pale yellow oil, $R_f$: 0.31 (silica gel; methylene chloride/methanol/concentrated ammonia=4:1:0.1)

EXAMPLE XXXIX

4-Acetylamino-1-benzyl-4-methyl-piperidine 190 ml of concentrated sulphuric acid are added dropwise over the course of 2 hours to a stirred solution of 38.8 g of 1-benzyl-4-hydroxy-4-methylpiperidine in 218 ml of acetonitrile, keeping the internal temperature below 30° C. by cooling in an ice bath. The mixture is then stirred at room temperature for 12 hours. It is subsequently poured onto ice and, while cooling, adjusted to pH 10 with 50% strength potassium hydroxide solution. The mixture is extracted three times with methylene chloride. The combined organic phases are then dried over sodium sulphate, and the solvent is distilled off in a rotary evaporator. The residue is triturated with petroleum ether, filtered off with suction and dried and employed without further purification in the next reaction.

Yield: 39.4 g (80% of theory) of gelatinous material, $R_f$: 0.40 (silica gel; methylene chloride/methanol=9:1)

EXAMPLE XL

4-Amino-1-benzyl-4-methylpiperidine 39.4 g of 4-acetylamino-1-benzyl-4-methylpiperidine are heated to boiling in 400 ml of concentrated hydrochloric acid for 3 days. After evaporation to half the volume in a rotary evaporator, the pH is adjusted to 12 with 50% strength sodium hydroxide solution while cooling. The mixture is extracted three times with methylene chloride. The combined organic phases are then dried over sodium sulphate, and the solvent is distilled off in a rotary evaporator. The residue is employed without further purification in the next reaction.

Yield: 25g (76% of theory) of brown oil, $R_f$: 0.45 (silica gel; methylene chloride/methanol/concentrated amonia= 9:2:0.1)

EXAMPLE XLI

3-Chloro-4-phenoxynitrobenzene 10 g of 3-chloro-4-fluoronitrobenzene, 7.8 g of anhydrous potassium carbonate, 6.5 g of phenol and 50 ml of dimethylformamide are heated at 135° C. for 5 hours. Solid constituents are then filtered off with suction, and the solution is evaporated in a rotary evaporator. The residue is dissolved in methylene chloride and extracted with 2N sodium hydroxide solution. The organic phase is then dried over sodium sulphate, and the solvent is distilled off in a rotary evaporator. The residue is employed without further purification in the next reaction.

Yield: 14.7g (100% of theory) of pale brown oil, $R_f$: 0.50 (silica gel; petroleum ether/ethyl acetate=5:1)

The following compound is obtained in analogy to Example XLI:

(1) 4-Benzyloxy-3-chloronitrobenzene $R_f$: 0.63 (silica gel; petroleum ether/ethyl acetate=5:2) Melting point: 120°–122° C.

EXAMPLE XLII

3-Chloro-4-phenoxyaniline 4.0 g of 3-chloro-4-phenoxynitrobenzene are dissolved in 40 ml of ethyl acetate and, after addition of 0.4 g of platinum oxide, hydrogenated at 18° C. under 1 bar until the precursor is consumed. The catalyst is then filtered off, the solvent is distilled off in a rotary evaporator, and the remaining oil is dried in vacuo. The product is used without further purification.

Yield: 3.6 g (100% of theory), $R_f$: 0.6 (alumina; petroleum ether/ethyl acetate=2:1)

The following compound is obtained in analogy to Example XLII:

(1) 4-Benzyloxy-3-chloroaniline $R_f$: 0.70 (alumina; petroleum ether/ethyl acetate=2:1)

EXAMPLE XLIII

4-Dimethylaminocyclohexanone 45.3 g of 8-dimethylamino-1,4-dioxaspiro[4.5]decane (Compound 1 in Example XXXV) are stirred in 400 ml of 2N hydrochloric acid at room temperature for 3 days. The solution is then extracted three times with diethyl ether, and the aqueous phase is saturated with potassium carbonate and extracted five times with ethyl acetate. The combined organic phases are then dried over sodium sulphate, and the solvent is distilled off in a rotary evaporator. The residue is employed without further purification in the next reaction.

Yield: 30.6 g (88% of theory) of pale brown oil, $R_f$: 0.53 (silica gel; methylene chloride/methanol/concentrated ammonia=10:2:0.1)

EXAMPLE XLIV cis/trans-N-Benzyl-N-(4-dimethylamino-cyclohexyl) amine

A mixture of 67.8 g of 4-dimethylaminocyclohexanone, 53 ml of benzylamine, 79 g of 4A molecular sieves and 500 ml of absolute toluene is stirred at room temperature for 12 hours. The molecular sieves are then filtered off, and the filtrate is evaporated in a rotary evaporator. The residue is dissolved in 400 ml of methanol and then, at room temperature, 5.5 g of sodium borohydride are added in portions and the mixture is stirred for 5 hours. The solvent is then distilled off in a rotary evaporator, 300 ml of methylene chloride and 200 ml of ice-water are added to the residue, and the mixture is adjusted to pH 5 with citric acid and then to pH 10 with sodium hydroxide solution. After phase separation, the mixture is extracted three times with methylene chloride, then the combined organic phases are washed with saturated sodium chloride solution and dried over sodium sulphate, and the solvent is distilled off in a rotary evaporator.

Yield: 107 g (95% of theory) of a brown oil which, according to the NMR spectra, is approximately a 60:40 cis/trans mixture. $R_f$: 0.27 (trans) and 0.37 (cis) (silica gel; mthylene chloride/methanol/concentrated ammonia= 10:2:0.1)

EXAMPLE XLV trans-N-Benzyl-N-(4-dimethylamino-cyclohexyl)amine fumarate

A solution of 25.5 g of fumaric acid in 720 ml of absolute tetrahydrofuran is rapidly added to a solution of 93.7 g of the compound of Example XLIV in 200 ml of absolute tetrahydrofuran at 50° C., and the mixture is stirred for a further 3 hours. The precipitated solid is filtered off with suction and washed with tetrahydrofuran and then suspended in 1.5 l of isopropanol and heated to boiling. The mixture is filtered hot, and the residue is triturated with ether and again filtered off with suction.

Yield: 66.9 g (70% of theory) of a grey solid which, according to the NMR spectra, consists of at least 95% of the trans compound. Melting point: 209°–215° C.

EXAMPLE XLVI trans-4-Dimethylaminocyclohexylamine 12 g of the fumarate obtained in Example XLV are taken up in 2n sodium hydroxide solution, and the solution is extracted three times with methylene chloride, and the combined organic phases are washed with saturated sodium chloride solution and dried over sodium sulphate, and the solvent is distilled off in a rotary evaporator. The residue is dissolved in 150 ml of methanol and, after addition of 4.5 g of palladium hydroxide on carbon hydrogenated at room temperature under 3 bar until no further hydrogen is taken up. The catalyst is then filtered off, the solvent is distilled off in a rotary evaporator, and the remaining oil is dried in vacco. The product is used without further purification.

Yield: 4.26 g (80% of theory) of a brown oil.

EXAMPLE XLVII

3-Amino-1-tert-butyloxycarbonylpiperidine 1.0 g of 3-aminocarbonyl-1-tert-butyloxycarbonylpiperidine (Compound 2 of Example XII) are added in portions to 9 ml of freshly prepared sodium hypobromite solution while cooling in ice. After 3 hours at room temperature, saturated sodium sulphite solution is added to the solution until it becomes cloudy. After saturation with potassium carbonate and extraction three times with ethyl acetate, the combined organic phases are dried over sodium sulphate, and the solvent is distilled off in a rotary evaporator. Yield: 693 mg (79% of theory) of a colourless oil, $R_f$: 0.44 (alumina; methylene chloride/methanol=10:0.6)

EXAMPLE 1

4-[(3-Chloro-4-fluorophenyl)amino]-6-[(trans-4-methoxycarbonylcyclohexyl)amino]pyrimido[5,4-d] pyrimidine 1.9 g of methyl trans-4-aminocyclohexanecarboxylate and 1.8 ml of N-ethyldiisopropylamine are added to 0.7 g of a mixture of 4-[(3-chloro-4-fluorophenyl)amino]-6-methylsulphinylpyrimido[5,4-d]pyrimidine and 4-[(3-chloro-4-fluorophenyl)amino]-6-methylsulphonylpyrimido [5,4-d]pyrimidine in 15 ml of dimethylformamide, and the mixture is heated at 80° C. for two hours. The reaction mixture is evaporated and, after addition of water, the solid is filtered off with suction. The crude product is purified by chromatography on a silica gel column with petroleum ether/ethyl acetate (6:10).

Yield: 0.69 g (80% of theory), Melting point: 204°–206° C.; $R_f$: 0.44 (silica gel; petroleum ether/ethyl acetate=6:10)

The following compounds are obtained in analogy to Example 1:

(1) 4-[(3-Chloro-4-fluorophenyl)amino]-6-[4-methoxycarbonylamino-1-piperidinyl]pyrimido[5,4-d]pyrimidine Prepared from the compounds of Example XXXII by reaction with 4-aminopiperidine and subsequent reaction with methyl chloroformate. Melting point: 195°–197° C.; $R_f$: 0.50 (silica gel; petroleum ether/ethyl acetate/methanol=10:10:1)

(2) 4-[(3-Chloro-4-fluorophenyl)amino]-6-[1-tert-butyloxycarbonyl-4-piperidinylamino]pyrimido[5,4-d]pyrimidine Prepared from the compounds of Examples XXXII and XII. Melting point: 196°–200° C. (decomposition); $R_f$: 0.50 (silica gel; petroleum ether/ethyl acetate/methanol=10:8:1)

(3) 4-[(4-Amino-3,5-dibromophenyl)amino]-6-[4-amino-1-piperidinyl]pyrimido[5,4-d]pyrimidine Melting point: 204°–206° C.; $R_f$: 0.71 (alumina; methylene chloride/methanol=10:1)

(4) (3'RS)-4-[(3-Chloro-4-fluorophenyl)amino]-6-[(3'-quinuclidinyl)amino]pyrimido[5,4-d]pyrimidine Melting point: 201°–203° C.; $R_f$: 0.23 (alumina; petroleum ether/ethyl acetate/methanol=10:5:2)

(5) 4-[(3-Chloro-4-fluorophenyl)amino]-6-[4-formylamino-1-piperidinyl]pyrimido[5,4-d]pyrimidine Prepared from the compounds of Example XXXII by reaction with 4-aminopiperidine and subsequent reaction with methyl formate. Melting point: 201°–203° C.; $R_f$: 0.24 (silica gel; petroleum ether/ethyl acetate/methanol=10:5:2)

(6) 4-[(3-Chloro-4-fluorophenyl)amino]-6-[2-aminoethylamino]-pyrimido[5,4-d]pyrimidine Melting point: 173°–175° C.; $R_f$: 0.41 (alumina; methylene chloride/methanol=70:1)

(7) 4-[(3-Chloro-4-fluorophenyl)amino]-6-[4-(aminomethyl)-1-piperidinyl]pyrimido[5,4-d]pyrimidine Melting point: 165° C.; $R_f$: 0.48 (alumina; methylene chloride/methanol=15:1)

(8) 4-[(3-Chloro-4-fluorophenyl)amino]-6-[1-methoxycarbonyl-4-piperidinylamino]pyrimido[5,4-d]pyrimidine Prepared from 4-[(3-chloro-4-fluorophenyl)amino]-6-[1-tert-butyloxycarbonyl-4-piperidinylamino]pyrimido[5,4-d]pyrimidine by reaction with trifluoroacetic acid and subsequent reaction with methyl chloroformate. Melting point: 213°–215° C.; $R_f$: 0.24 (silica gel; petroleum ether/ethyl acetate/methanol=20:10:1)

(9) 4-[(3-Chloro-4-fluorophenyl)amino]-6-[3-aminopropylamino]pyrimido[5,4-d]pyrimidine Melting point: 177°–179° C.; $R_f$: 0.50 (alumina; methylene chloride/methanol=7:1)

(10) 4-[(3-Chloro-4-fluorophenyl)amino]-6-[4-aminobutylamino]pyrimido[5,4-d]pyrimidine Melting point: 160°–162° C.; $R_f$: 0.60 (alumina; methylene chloride/methanol=7:1)

(11) 4-[(3-Chloro-4-fluorophenyl)amino]-6-[2-amino-1-propylamino]pyrimido[5,4-d]pyrimidine Melting point: 168°–170° C.; $R_f$: 0.20 (silica gel; petroleum ether/ethyl acetate/methanol=10:10:3:0.05)

(12) 4-[(3-Chloro-4-fluorophenyl)amino]-6-[4-methyl-1-homopiperazinyl]pyrimido[5,4-d]pyrimidine Melting point: 122°–124° C.; $R_f$: 0.60 (alumina; petroleum ether/ethyl acetate/methanol=40:40:1) Calculated: C 55.74 H 4.93 N 25.27; Found: 55.99 5.12 25.13

(13) 4-[(3-Chloro-4-fluorophenyl)amino]-6-[1-homopiperazinyl]-pyrimido[5,4-d]pyrimidine Melting point: >300° C.; $R_f$: 0.40 (silica gel; petroleum ether/ethyl acetate/methanol=10:10:3)

(14) 4-[(3-Chloro-4-fluorophenyl)amino]-6-[4-aminobenzylamino]pyrimido[5,4-d]pyrimidine Melting point: 218°–220° C.; $R_f$: 0.58 (alumina; petroleum ether/ethyl acetate/methanol=10:10:2)

(15) 4-[(4-Amino-3,5-dichlorophenyl)amino]-6-[(trans-4-methoxycarbonylcyclohexyl)amino]pyrimido[5,4-d]pyrimidine Melting point: 219°–224° C.; $R_f$: 0.39 (silica gel; petroleum ether/ethyl acetate/methanol=8:10)

(16) 4-[(4-Amino-3,5-dichlorophenyl)amino]-6-[(trans-4-carboxycyclohexyl)amino]pyrimido[5,4-d]pyrimidine Prepared from 4-[(4-amino-3,5-dichlorophenyl)amino]-6-[(trans-4-methoxycarbonylcyclohexyl)amino]pyrimido[5,4-d]-pyrimidine by hydrolysis with sodium hydroxide solution. Melting point: 339° C.; $R_f$: 0.37 (silica gel; petroleum ether/ethyl acetate/methanol=10:10:3)

(17) 4-[(4-Amino-3,5-dichlorophenyl)amino]-6-[trans-4-(morpholinocarbonyl)cyclohexylamino]pyrimido[5,4-d]pyrimidine Prepared from 4-[(4-amino-3,5-dichlorophenyl)amino]-6-[(trans-4-carboxycyclohexyl)amino]pyrimido[5,4-d]pyrimidine by reaction with O-(benzotriazol-1-yl)-N,N,N',N',-tetramethyluronium tetrafluoroborate, triethylamine and morpholine. Melting point: 204°–207° C.; $R_f$: 0.53 (silica gel; petroleum ether/ethyl acetate/methanol=10:10:4)

(18) 4-[(4-Amino-3,5-dichlorophenyl)amino]-6-[trans-4-(pyrrolidinocarbonyl)cyclohexylamino]pyrimido[5,4-d]pyrimidine Prepared from 4-[(4-amino-3,5-dichlorophenyl)amino]-6-[(trans-4-carboxycyclohexyl)amino]pyrimido[5,4-d]pyrimidine by reaction with O-(benzotriazol-1-yl)-N,N,N',N'-tetramethyluronium tetrafluoroborate, triethylamine and pyrrolidine. Melting point: 228°–230° C,; $R_f$: 0.43 (silica gel; petroleum ether/ethyl acetate/methanol=10:10:4) Calculated: C 55.09 H 5.23 N 22.35; Found: 55.07 5.19 22.33 14.22

(19) 4-[(3-Chloro-4-fluorophenyl)amino]-6-[4-(4-piperidinyl)-1-piperidinyl]pyrimido[5,4-d]pyrimidine Melting point: 170° C. (decomposition); $R_f$: 0.45 (alumina; methylene chloride/ethyl acetate/methanol/concentrated ammonia=10:4:1:0.05)

(20) 4-[(3-Chloro-4-fluorophenyl)amino]-6-[1-(1-piperidinyl)-2-propylamino]pyrimido[5,4-d]pyrimidine Melting point: 188°–190° C.; $R_f$: 0.38 (alumina; petroleum ether/ethyl acetate=1:1)

(21) 4-[(3-Chloro-4-fluorophenyl)amino]-6-[1-(N,N-diethylamino)-2-propylamino]pyrimido[5,4-d]pyrimidine Melting point: 193°–195° C.; $R_f$: 0.55 (alumina; petroleum ether/ethyl acetate=1:1)

(22) 4-[(3-Chloro-4-fluorophenyl)amino]-6-[4-(aminomethyl)cyclohexylmethylamino]pyrimido[5,4-d]pyrimidine Melting point: 155°–160° C.; $R_f$: 0.60 (alumina; methylene chloride/ethyl acetate/methanol/concentrated ammonia=10:5:2:0.05)

(23) 4-[(3-Chloro-4-fluorophenyl)amino]-6-[N-ethyl-N-(2-hydroxyethyl)amino]pyrimido[5,4-d]pyrimidine Melting point: 194°–196° C.; $R_f$: 0.45 (silica gel; petroleum ether/ethyl acetate/methanol=10:10:1)

(24) 4-[(3-Chloro-4-fluorophenyl)amino]-6-[4-quinuclidinylmethylamino]pyrimido[5,4-d]pyrimidine Prepared from the compounds of Examples XXXII and XIV(1). Melting point: 221°–223° C.; $R_f$: 0.53 (alumina, methylene chloride/methanol=20:1)

(25) 4-[(3-Chloro-4-fluorophenyl)amino]-6-[2,2-dimethoxyethylamino]pyrimido[5,4-d]pyrimidine Melting point: 169°–171° C.; $R_f$: 0.47 (silica gel; petroleum ether/ethyl acetate/methanol=10:8:1)

(26) 4-[(3-Chloro-4-fluorophenyl)amino]-6-[(1-tert-butyloxycarbonyl-4-piperidinyl)methylamino]pyrimido[5,4-d]pyrimidine Prepared from the compounds of Examples XXXII and XIII. Melting point: 210°–213° C.; $R_f$: 0.38 (silica gel; petroleum ethyl/ethyl acetate/methanol=10:5:1) Calculated: C 56.61 H 5.58 N 20.09 Cl 7.26; Found: 56.68 5.52 19.80 7.33

(27) 4-[(3-Chloro-4-fluorophenyl)amino]-6-[2-amino-2-methyl-1-propylamino]pyrimido[5,4-d]pyrimidine Melting point: 205°–207° C.; $R_f$: 0.47 (alumina; methylene chloride/methanol=10:1)

(28) 4-[(3-Chloro-4-fluorophenyl)amino]-6-[N-methyl-N-(1-methyl-4-piperidinyl)amino]pyrimido[5,4-d]pyrimidine Melting point: 197°–199° C.; $R_f$: 0.56 (alumina; petroleum ether/ethyl acetate/methanol=3:10:0.2)

(29) 4-[(3-Chloro-4-fluorophenyl)amino]-6-[4-piperidinylmethylamino]pyrimido[5,4-d]pyrimidine Prepared from 4-[(3-chloro-4-fluorophenyl)amino]-6-[(1-tert-butyloxycarbonyl-4-piperidinyl)methylamino]pyrimido[5,4-d]pyrimidine by reaction with trifluoroacetic acid. Melting point: 204°–206° C.; $R_f$: 0.42 (alumina; methanol chloride/methanol=10:1)

(30) 4-[(3-Chloro-4-fluorophenyl)amino]-6-[4-(morpholino)-1-Piperidinyl]pyrimido[5,4-d]pyrimidine Prepared from the compounds of Example XXXII by reaction with 4-hydroxypiperidine, oxidation with Dess-Martin reagent and subsequent reductive amination with morpholine and sodium cyanoborohydride. Melting point: 222°–224° C.; $R_f$: 0.40 (silica gel; petroleum ether/ethyl acetate/methanol=10:10:2)

(31) 4-[(3-Chloro-4-fluorophenyl)amino]-6-[4-(1-pyrrolidinyl)-1-piperidinyl]pyrimido[5,4-d]pyrimidine Prepared from 4-[(3-chloro-4-fluorophenyl)amino]-6-[4-hydroxy-1-piperidinyl]pyrimido[5,4-d]pyrimidine by oxidation with Dess-Martin reagent and subsequent reductive amination with pyrrolidine and sodium cyanoborohydride. Melting point: 202°–204° C.; $R_f$: 0.58 (alumina; petroleum ether/ethyl acetate/methanol=10:10:1)

(32) 4-[(3-Chloro-4-fluorophenyl)amino]-6-[4-(3-methoxyphenyl)-1-piperazinyl]pyrimido[5,4-d]pyrimidine Melting point: 185°–188° C.; $R_f$: 0.63 (silica gel; petroleum ether/ethyl acetate/methanol=10:10:0.5)

(33) 4-[(3-Chloro-4-fluorophenyl)amino]-6-[4-(2-methoxyphenyl)-1-piperazinyl]pyrimido[5,4-d]pyrimidine Melting point: 150°–152° C.; $R_f$: 0.48 (silica gel; petroleum ether/ethyl acetate=1:2)

(34) 4-[(3-Chloro-4-fluorophenyl)amino]-6-[3-aminocarbonyl-1-piperidinyl]pyrimido[5,4-d]pyrimidine Melting point: 264°–267° C.; $R_f$: 0.50 (silica gel; petroleum ether/ethyl acetate/methanol=10:8:3)

(35) 4-[(3-Chloro-4-fluorophenyl)amino]-6-[2-(4-tert-butyloxycarbonyl-1-piperazinyl)ethylamino]pyrimido[5,4-d]pyrimidine Prepared from the compounds of Example XXXII by reaction with 1-(2-aminoethyl)piperazine and subsequent reaction with di-tert-butyl dicarbonate and triethylamine. Melting point: sinters at 100°–106° C.; $R_f$: 0.42 (silica gel; petroleum ether/ethyl acetate/methanol=10:10:2)

(36) 4-[(3-Chloro-4-fluorophenyl)amino]-6-[4-(4-hydroxyphenyl)-2-methyl-1-pyrrolidinyl]pyrimido[5,4-d]pyrimidine Melting point: 223°–228° C.; $R_f$: 0.56 (silica gel; petroleum ether/ethyl acetate/methanol=10:5:1) Calculated: C 61.27 H 4.47 N 18.64 Cl 7.86; Found: 61.14 4.42 18.36 7.81

(37) 4-[(3-Chloro-4-fluorophenyl)amino]-6-[1-phenoxy-2-propyl-amino]pyrimido[5,4-d]pyrimidine Melting point: 163°–167° C.; $R_f$: 0.53 (silica gel; petroleum ether/ethyl acetate/methanol=10:5:1) Calculated: C 59.37 H 4.27 N 19.78 Cl 8.34; Found: 59.07 4.37 19.29 8.24

(38) 4-[(3-Chloro-4-fluorophenyl)amino]-6-[3-(aminomethyl)cyclohexylmethylamino]pyrimido[5,4-d]pyrimidine Melting point: 145°–148° C.; $R_f$: 0.48 (alumina; methylene chloride/methanol=10:1)

(39) 4-[(3-Chloro-4-fluorophenyl)amino]-6-[1-(4-aminophenyl)-2-propylamino]pyrimido[5,4-d]pyrimidine Melting point: 172°–176° C.; $R_f$: 0.59 (silica gel; petroleum ether/ethyl acetate/methanol=10:10:3)

(40) 4-[(3-Chloro-4-fluorophenyl)amino]-6-[4-(4-methoxyphenyl)-1-piperazinyl]pyrimido[5,4-d]pyrimidine Melting point: 176°–178° C.; $R_f$: 0.50 (silica gel; petroleum ether/ethyl acetate=1:1)

(41) 4-[(3-Chloro-4-fluorophenyl)amino]-6-[4-(1-methyl-4-piperidinyl)-1-piperazinyl]pyrimido[5,4-d]pyrimidine Prepared from 4-[(3-chloro-4-fluorophenyl)amino]-6-[4-(4-piperidinyl)-1-piperazinyl]pyrimido[5,4-d]pyrimidine by reductive amination with formaldehyde and sodium cyanoborohydride. Melting point: 159°–162° C.; $R_f$: 0.58 (alumina; petroleum ether/ethyl acetate/methanol=10:10:1)

(42) 4-[(3-Chloro-4-fluorophenyl)amino]-6-[1-benzyl-4-(1-azacycloheptyl)amino]pyrimido[5,4-d]pyrimidine Prepared from the compounds of Examples XXXII and XX. Melting point: 147°–149° C.; $R_f$: 0.43 (silica gel; petroleum ether/ethyl acetate/methanol=10:10:3) Calculated: C 62.82 H 5.27 N 20.51 Cl 7.42; Found: 63.04 5.29 20.24 7.42

(43) 4-[(3-Tetrafluoroethoxyphenyl)amino]-6-[trans-4-hydroxycyclohexylamino]pyrimido[5,4-d]pyrimidine Melting point: 218°–220° C.; $R_f$: 0.37 (silica gel; petroleum ether/ethyl acetate/methanol=10:10:1)

(44) 4-[(4-Benzylphenyl)amino]-6-[trans-4-hydroxycyclohexylamino]pyrimido[5,4-d]pyrimidine Melting point: 232°–234° C.; $R_f$: 0.45 (silica gel; petroleum ether/ethyl acetate/methanol=10:10:1)

(45) 4-[(3-Benzyloxyphenyl)amino]-6-[trans-4-hydroxycyclohexylamino]pyrimido[5,4-d]pyrimidine Melting point: 227°–230° C.; $R_f$: 0.30 (silica gel; petroleum ether/ethyl acetate/methanol=10:10:1) Calculated: C 67.85 H 5.92 N 18.99; Found: 67.22 5.98 18.35

(46) 4-[(3-Chloro-4-fluorophenyl)amino]-6-[4-(1-methyl-4-piperazinyl)cyclohexylamino]pyrimido[5,4-d]pyrimidine Prepared from the compounds of Example XXXII by reaction with 4-aminocyclohexanol, oxidation with Dess-Martin reagent and subsequent reductive amination with 1-methylpiperazine and sodium cyanoborohydride. Melting point: 194°–196° C.; $R_f$: 0.58 (alumina; methylene chloride/ethyl acetate/methanol=10:5:1)

(47) 4-[(3-Hydroxymethylphenyl)amino]-6-[trans-4-hydroxycyclohexylamino]pyrimido[5,4-d]pyrimidine Melting point: 255°–257° C.; $R_f$: 0.30 (silica gel; petroleum ether/ethyl acetate/methanol=10:10:3)

(48) 4-[(3-Chloro-4-fluorophenyl)amino]-6-[4-hydroxy-1-piperidinyl]pyrimido[5,4-d]pyrimidine Melting point: 243°–246° C.; $R_f$: 0.45 (alumina; methylene chloride/ethyl acetate/methanol=10:4:1)

(49) 4-[(3-Chloro-4-fluoro henyl)amino]-6-[1-piperidinyl]pyrimido[5,4-d]pyrimidine Melting point: 196°–198° C.; $R_f$: 0.52 (silica gel; petroleum ether/ethyl acetate=10:5)

(50) 4-[(3-Chloro-4-fluorophenyl)amino]-6-[(1-cyano-4-piperidinyl)amino]pyrimido[5,4-d]pyrimidine Prepared from 4-[(3-chloro-4-fluorophenyl)amino]-6-[1-tert-butyloxycarbonyl-4-piperidinylamino]pyrimido[5,4-d]

pyrimidine by reaction with trifluoroacetic acid and subsequent reaction with cyanogen bromide. Melting point: 245°–247° C.; $R_f$: 0.59 (silica gel; petroleum ether/ethyl acetate/methanol=10:10:3)

(51) 4-[(3-Chloro-4-fluorophenyl)amino]-6-[(1-methyl-4-piperidinyl)methylamino]pyrimido[5,4-d]pyrimidine Prepared from 4-[(3-chloro-4-fluorophenyl)amino]-6-[4-piperidinylmethylamino]pyrimido[5,4-d]pyrimidine by reaction with trifluoroacetic acid and subsequent reductive amination with formaldehyde and sodium cyanoborohydride. Melting point: 198°–201° C.; $R_f$: 0.65 (alumina; methylene chloride/methanol=20:1)

(52) 4-[(3-Chloro-4-fluorophenyl)amino]-6-[2-(4-(morpholinocarbonyl)-1-piperazinyl)ethylamino]pyrimido[5,4-d]pyrimidine Prepared from the compounds of Example XXXII by reaction with 1-(2-aminoethyl)piperazine and subsequent reaction with 4-morpholinecarbonyl chloride and triethylamine. Melting point: 163°–168° C.; $R_f$: 0.58 (alumina; methylene chloride/methanol=10:0.4)

(53) 4-[(3-Chloro-4-fluorophenyl)amino]-6-aminopyrimido-[5,4-d]pyrimidine

Melting point: 300°–301° C.; $R_f$: 0.41 (alumina; methylene chloride/methanol=20:1)

(54) 4-[(3-Chloro-4-fluorophenyl)amino]-6-[5-aminopentylamino]pyrimido[5,4-d]pyrimidine Melting point: 153°–155° C.; $R_f$: 0.52 (alumina; methylene chloride/methanol=5:1)

(55) 4-[(3-Chloro-4-fluorophenyl)amino]-6-[1-azacycloheptyl]pyrimido[5,4-d]pyrimidine Melting point: 87°–90° C.; $R_f$: 0.60 (silica gel; methylene chloride/methanol=25:1)

(56) 4-[(3-Chloro-4-fluorophenyl)amino]-6-[4-amino-1-azacycloheptyl]pyrimido[5,4-d]pyrimidine Prepared from the compounds of Examples XXXII and XXI. Melting point: 122°–124° C.; $R_f$: 0.59 (silica gel; methylene chloride/methanol/concentrated ammonia=80:20:2)

(57) 4-[(3-chloro-4-fluorophenyl)amino]-6-[1-tert-butyloxy-carbonyl-4-(azacycloheptyl)amino]pyrimido[5,4-d]pyrimidine Prepared from the compounds of Examples XXXII and XIII. Melting point: 175°–177° C.; $R_f$: 0.33 (silica gel; petroleum ether/ethyl acetate/methanol=10:5:1) Calculated: C 56.61 H 5.58 N 20.09 Cl 7.27; Found: 56.89 5.58 19.81 7.37

(58) 4-[(3-Chloro-4-fluorophenyl)amino]-6-[4-(azacycloheptyl)amino]pyrimido[5,4-d]pyrimidine Prepared from 4-[(3-chloro-4-fluorophenyl)amino]-6-[1-tert-butyloxycarbonyl-4-(azacycloheptyl)amino]pyrimido[5,4-d]pyrimidine by reaction with trifluoroacetic acid. Melting point: 266°–268° C.; $R_f$: 0.23 (silica gel; methylene chloride/methanol/concentrated ammonia=70:30:2)

(59) 4-(3-Chloro-4-fluorophenyl)amino]-6-[trans-4-aminomethylcyclohexylamino]pyrimido[5,4-d]pyrimidine Prepared from the compounds of Examples XXXII and XVIII and subsequent reaction with trifluoroacetic acid. Melting point: 170°–173° C.; $R_f$: 0.37 (alumina; methylene chloride/methanol=10:1)

(60) 4-[(3-Chloro-4-fluorophenyl)amino]-6-[trans-4-(benzyloxycarbonylamino)cyclohexylmethylamino]pyrimido[5,4-d]pyrimidine Prepared from the compounds of Examples XXXII and XVII. Melting point: 176°–179° C.; $R_f$: 0.47 (silica gel; petroleum ether/ethyl acetate/methanol=10:8:2); Calculated: C 60.50 H 5.08 N 18.29 Cl 6.61; Found: 60.59 5.13 18.13 6.75

(61) 4-[(3-Chloro-4-fluorophenyl)amino]-6-[3-aminomethyl-1-piperidinyl]pyrimido[5,4-d]pyrimidine Prepared from the compounds of Examples XXXII and XIV. Melting point: 132°–137° C.; $R_f$: 0.67 (silica gel; methylene chloride/methanol/concentrated ammonia=10:2:0.05)

(62) 4-[(4-Amino-2,5-dichlorophenyl)amino]-6-[trans-4-hydroxycyclohexylamino]pyrimido[5,4-d]pyrimidine Melting point: 268°–270° C.; $R_f$: 0.43 (silica gel; petroleum ether/ethyl acetate/methanol=10:10:2)

(63) 4-[4-Biphenylylamino]-6-[trans-4-hydroxycyclohexylamino]pyrimido[5,4-d]pyrimidine Melting point: 246°–248° C.; $R_f$: 0.37 (silica gel; petroleum ether/ethyl acetate/methanol=10:10:3)

(64) 4-[3-Phenoxyphenylamino]-6-[trans-4-hydroxycyclohexylamino[pyrimido[5,4-d]pyrimidine Melting point: 204°–206° C.; $R_f$: 0.35 (silica gel; petroleum ether/ethyl acetate/methanol=10:10:2)

(65) 4-[(3-Chloro-4-fluorophenyl)amino]-6-[(trans-4-aminocyclohexyl)methylamino]pyrimido[5,4-d]pyrimidine Prepared from 4-[(3-chloro-4-fluorophenyl)amino]-6-(trans-4-(benzyloxycarbonylamino)cyclohexylmethylamino]pyrimido-[5,4-d]pyrimidine by catalytic hydrogenation. Melting point: 166°–169° C.; $R_f$: 0.53 (silica gel; methylene chloride/methanol/concentrated ammonia=10:1:0.05); Mass spectrum: M$^+$=401/403 (Cl)

(66) 4-[(3-Chloro-4-fluorophenyl)amino]-6-(3-(aminocarbonylmethyl)-1-piperidinyl]pyrimido[5,4-d]pyrimidine Prepared from the compounds of Examples XXXII and VII. Melting point: 247°–248° C.; $R_f$: 0.38 (silica gel; petroleum ether/ethyl acetate/methanol=10:8:2); Mass spectrum: M$^+$=415/417 (Cl)

(67) 4-[(3-Chloro-4-fluorophenyl)amino]-6-[trans-4-(2-(1-pyrrolidinylcarbonyl)ethyl)cyclohexylamino]pyrimido[5,4-d]pyrimidine Prepared from the compounds of Example XXXII and X, hydrolysis with sodium hydroxide solution and methanol and subsequent reaction with O-(benzotriazol-1-yl)-N,N,N', N'-tetramethyluronium tetrafluoroborate, triethylamine and pyrrolidine. Melting point: 187°–192° C.; $R_f$: 0.49 (silica gel; petroleum ether/ethyl acetate/methanol=10:8:3); Calculated: C 60.30 H 5.87 N 19.69 Cl 7.12; Found: 60.39 5.89 19.50 7.39

(68) 4-[(3-Chloro-4-cyanophenyl)amino]-6-[trans-4-hydroxycyclohexylamino]pyrimido[5,4-d]pyrimidine Melting point: 244°–247° C.; $R_f$: 0.30 (alumina; petroleum ether/ethyl acetate/methanol=10:10:2); Mass spectrum: M$^+$=395/397 (Cl)

(69) 4-[(4-Chloro-3-cyanophenyl)amino]-6-[trans-4-hydroxycyclohexylamino]pyrimido[5,4-d]pyrimidine Melting point: 250°–252° C.; $R_f$: 0.57 (silica gel; petroleum ether/ethyl acetate/methanol=10:10:2); Mass spectrum: M$^+$=395/397 (Cl)

(70) 4-[(3-Chloro-4-fluorophenyl)amino]-6-[4-methylaminocyclohexylamino]pyrimido[5,4-d]pyrimidine 1:1 cis/trans mixture Prepared from the compounds of Example XXXII by reaction with 4-aminocyclohexanol, oxidation with Dess-Martin reagent and subsequent reductive amination with methylamine and sodium cyanoborohydride. Melting point: 125°–165° C.; $R_f$: 0.40 (alumina; petroleum ether/ethyl acetate/methanol/concentrated ammonia=10:10:2:0.05); Mass spectrum: M$^+$=401/403 (Cl)

(71) 4-[(3-Chloro-4-fluorophenyl)amino]-6-(cis-4-amino-3-methyl-1-piperidinyl)pyrimido[5,4-d]pyrimidine Prepared from the compounds of Examples XXXII and XXIX. Melting point: 161°–164° C.; $R_f$: 0.25 (alumina; methylene chloride/methanol/concentrated ammonia=50:1:1)

(72) 4-[(3-Chloro-4-fluorophenyl)amino]-6-(trans-4-amino-3-methyl-1-piperidinyl)pyrimido[5,4-d]pyrimidine Prepared from the compounds of Examples XXXII and XXIX(1).

Melting point: 158° C.; $R_f$: 0.20 (silica gel; methylene chloride/methanol/concentrated ammonia=50:1:0.5)

(73) 4-[(3-Chloro-4-fluorophenyl)amino]-6-[2-(4-acetyl-1-piperazinyl)ethylamino]pyrimido[5,4-d]pyrimidine Prepared from 4-[(3-chloro-4-fluorophenyl)amino]-6-[2-(1-piperazinyl)ethylamino]pyrimido[5,4-d]pyrimidine by reaction with acetic anhydride. Melting point: 196°–198° C.; $R_f$: 0.59 (alumina; methylene chloride/methanol=10:0.4)

(74) 4-[(3-Chloro-4-fluorophenyl)amino]-6-(4-tetrahydropyranyloxy)pyrimido[5,4-d]pyrimidine Prepared from the compounds of Example XXXII using 4-hydroxytetrahydropyran and metallic sodium. Melting point: 220°–222° C.; $R_f$: 0.50 (silica gel; petroleum ether/ethyl acetate/methanol=10:10:1)

(75) 4-[(3-Chloro-4-fluorophenyl)amino]-6-(3-tetrahydrofuranyloxy)pyrimido[5,4-d]pyrimidine Prepared from the compounds of Example XXXII using 3-hydroxytetrahydrofuran and metallic sodium. Melting point: 163°–165° C.; $R_f$: 0.40 (alumina; petroleum ether/ethyl acetate/methanol=10:10:1)

(76) 4-[(3-Chloro-4-fluorophenyl)amino]-6-[1-(hydroxymethyl)cyclopentylamino]pyrimido[5,4-d]pyrimidine Melting point: 201°–203° C.; $R_f$: 0.39 (silica gel; petroleum ether/ethyl acetate/methanol=10:10:1)

(77) 4-[(3-Chloro-4-fluorophenyl)amino]-6-[(4-aminocyclohexyl)-amino]pyrimido[5,4-d]pyrimidine Melting point: 170°–172° C.; $R_f$: 0.35 (alumina; petroleum ether/ethyl acetate/methanol=10:10:2)

(78) 4-[(3-Chloro-4-fluorophenyl)amino]-6-isopropylaminopyrimido[5,4-d]pyrimidine Melting point: 230°–234° C.; $R_f$: 0.54 (silica gel; petroleum ether/ethyl acetate/methanol=10:5:1) Calculated: C 54.14 H 4.24 N 25.25; Found: 54.32 4.29 25.14

(79) 4-[(3-Methylphenyl)amino]-6-[(1-(N,N-dimethylaminocarbonyl)-4-piperidinyl)amino]pyrimido[5,4-d]pyrimidine Prepared from the compounds of Examples XXXII and XII, subsequent reaction with trifluoroacetic acid and subsequent reaction with N,N-dimethylcarbamoyl chloride. Melting point: 185°–187° C.; $R_f$: 0.42 (silica gel; petroleum ether/ethyl acetate/methanol=10:8:2)

(80) 4-[(3-Methylphenyl)amino]-6-[(1-formyl-4-piperidinyl)-amino]pyrimido[5,4-d]pyrimidine Prepared from the compounds of Examples XXXII and XII, subsequent reaction with trifluoroacetic acid and subsequent reaction with methyl formate. Melting point: 198°–193° C.; $R_f$: 0.53 (silica gel; methylene chloride/methanol=10:1); Calculated: C 62.79 H 5.82 N 26.98; Found: 62.65 6.04 26.21

(81) 4-[(3-Chloro-4-fluorophenyl)amino]-6-(4-piperidinylamino)pyrimido[5,4-d]pyrimidine Prepared from the compounds of Examples XXXII and XII and subsequent reaction with trifluoroacetic acid. Melting point: 239°–243° C.; $R_f$: 0.66 (alumina; methylene chloride/methanol=10:1)

(82) 4-[(3-Chloro-4-fluorophenyl)amino]-6-[trans-4-carboxycyclohexylamino]pyrimido[5,4-d]pyrimidine Prepared from the compounds of Example XXXII and methyl trans-4-aminocyclohexanecarboxylate and subsequent hydrolysis with sodium hydroxide solution. Melting point: >290° C.; Calulated: C 54.75 H 4.35 N 20.16 Cl 8.51; Found: 54.49 4.69 19.56 8.48

(83) 4-[(3-Chloro-4-fluorophenyl)amino]-6-[trans-4-(morpholinocarbonyl)cyclohexylamino]pyrimido[5,4-d]pyrimidine Prepared from 4-[(3-chloro-4-fluorophenyl)amino]-6-[trans-4-carboxycyclohexylamino]pyrimido[5,4-d]pyrimidine by reaction with O-(benzotriazol-1-yl)-N,N,N',N'-tetramethyluronium tetrafluoroborate, triethylamine and morpholine. Melting point: 221°–225° C.; $R_f$: 0.47 (silica gel; petroleum ether/ethyl acetate/methanol=10:8:3)

(84) 4-[(3-Chloro-4-fluorophenyl)amino]-6-[trans-4-(pyrrolidinocarbonyl)cyclohexylamino]pyrimido[5,4-d]pyrimidine Prepared from 4-[(3-chloro-4-fluorophenyl)amino]-6-[trans-4-carboxycyclohexylamino]pyrimido[5,4-d]pyrimidine by reaction with O-(benzotriazol-1-yl)-N,N,N',N'-tetramethyluronium tetrafluoroborate, triethylamine and pyrrolidine. Melting point: 206°–209° C.; $R_f$: 0.52 (silica gel; petroleum ether/ethyl acetate/methanol=10:8:3)

(85) 4-[(3-Chloro-4-fluorophenyl)amino]-6-[3-(morpholino)-1-propylamino]pyrimido[5,4-d]pyrimidine Melting point: 157°–159° C.; $R_f$: 0.48 (silica gel; petroleum ether/ethyl acetate/methanol=10:10:3); Calculated: C 54.61 H 5.07 N 23.46; Found: 54.40 5.25 23.30

(86) 4-[(3-Chloro-4-fluorophenyl)amino]-6-[3-amino-1-pyrrolidinyl]pyrimido[5,4-d]pyrimidine Melting point: 174°–176° C.; $R_f$: 0.54 (alumina; methylene chloride/methanol=15:1)

(87) 4-[(3-Chloro-4-fluorophenyl)amino]-6-[4-(N-acetyl-N-methylamino)cyclohexylamino]pyrimido[5,4-d]pyrimidine Prepared from the compounds of Examples XXXII and XXII. Melting point: 195°–197° C.; $R_f$: 0.35 (silica gel; petroleum ether/ethyl acetate/methanol=10:10:2)

(88) 4-[(3-Chloro-4-fluorophenyl)amino]-6-[4-tetrahydropyranylamino]pyrimido[5,4-d]pyrimidine Prepared from the compounds of Examples XXXII and XXIV. Melting point: 245°–248° C.; $R_f$: 0.47 (silica gel; petroleum ether/ethyl acetate=3:10)

(89) 4-[(3-Methylphenyl)amino]-6-[(1-cyano-4-piperidinyl)amino]pyrimido[5,4-d]pyrimidine Prepared from the compounds of Examples XXXII and XII, subsequent reaction with trifluoroacetic acid and subsequent reaction with cyanogen bromide. Melting point: 178°–181° C.; $R_f$: 0.61 (silica gel; petroleum ether/ethyl acetate/methanol=10:10:3)

(90) 4-[(3-Chloro-4-fluorophenyl)amino]-6-(1-methyl-4-piperdinylamino)pyrimido[5,4-d]pyrimidine Melting point: 175°–177° C.; $R_f$: 0.65 (silica gel; petroleum ether/ethyl acetate/methanol=10:10:2)

(91) 4-[(3-Chloro-4-fluorophenyl)amino]-6-[(4-dimethylaminocyclohexyl)amino]pyrimido[5,4-d]pyrimidine Prepared from the compounds of Example XXXII and 1,4-diaminocyclohexane and subsequent reductive amination with formaldehyde and sodium cyanoborohydride. Melting point: 178°–180° C.; $R_f$: 0.20 (alumina; petroleum ether/ethyl acetate/methanol=10:10:0.5)

(92) 4-[(3-Chloro-4-fluorophenyl)amino]-6-(tert-butylamino)pyrimido[5,4-d]pyrimidine Melting point: 265°–267° C.; $R_f$: 0.73 (silica gel; petroleum ether/ethyl acetate/methanol=10:10:1)

(93) 4-[(3-Chloro-4-fluorophenyl)amino]-6-[3-amino-1-piperidinyl]pyrimido[5,4-d]pyrimidine Melting point: 172°–175° C.; $R_f$: 0.33 (silica gel; methylene chloride/methanol=10:2)

(94) 4-[(3-Chloro-4-fluorophenyl)amino]-6-[2-(1-piperazinyl)ethylamino]pyrimido[5,4-d]pyrimidine Prepared from the compounds of Example XXXII and 1-(2-aminoethyl)piperazine. Melting point: 173°–175° C.; $R_f$: 0.53 (silica gel; methylene chloride/methanol=10:1)

(95) 4-[(4-Amino-5-bromo-3-chlorophenyl)amino]-6-[(trans-4-hydroxycyclohexyl)amino]pyrimido[5,4-d]pyrimidine Melting point: 238°–240° C.; $R_f$: 0.50 (alumina; petroleum ether/ethyl acetate/methanol=10:10:2)

(96) 4-[(3-Chloro-4-fluorophenyl)amino]-6-[(4-oxocyclohexyl)amino]pyrimido[5,4-d]pyrimidine Prepared from the compounds of Example XXXII by reaction with 4-aminocyclohexanol and subsequent oxidation with Dess-Martin reagent. Melting point: 232°–234° C.; $R_f$: 0.48 (silica gel; petroleum ether/ethyl acetate/methanol=10:10:2)

(97) 4-[(3-Chloro-4-fluorophenyl)amino]-6-[(cis-4-hydroxycyclohexyl)amino]pyrimido[5,4-d]pyrimidine Melting point: 270°–275° C.; $R_f$: 0.47 (alumina; methylene chloride/ethyl acetate/methanol=10:4:3)

(98) 4-[(3-Chloro-4-fluorophenyl)amino]-6-[4-morpholinocyclohexylamino]pyrimido[5,4-d]pyrimidine Prepared from the compounds of Example XXXII by reaction with 4-aminocyclohexanol, oxidation with Dess-Martin reagent and subsequent.reductive amination with morpholine and sodium cyanoborohydride. Melting point: 233°–235° C.; $R_f$: 0.24 (silica gel; petroleum ether/ethyl acetate/methanol=10:10:2)

(99) 4-[(3-Chloro-4-fluorophenyl)amino]-6-[4-(2-aminoethyl)-1-piperazinyl]pyrimido[5,4-d]pyrimidine Prepared from the compounds of Examples XXXII and XXV and subsequent reaction with 1N potassium bisulphate solution. Melting point: 175°–180° C.; $R_f$: 0.35 (alumina; methylene chloride/methanol=10:1.5)

(100) 4-[(3-Chloro-4-fluorophenyl)amino]-6-[4-(1-pyrrolidinyl)cyclohexylamino]pyrimido[5,4-d]pyrimidine Prepared from the compounds of Example XXXII by reaction with 4-aminocyclohexanol, oxidation with Dess-Martin reagent and subsequent reductive amination with pyrrolidine and sodium cyanoboroh ydride. Melting point: 192°–195° C.; $R_f$: 0.38 (alumina; petroleum ether/ethyl acetate/methanol=10:10:1)

(101) 4-[(3-Methylphenyl)amino]-6-[2,6-dimethylmorpholinolpyrimido[5,4-d]pyrimidine 1:1 cis-trans isomer mixture Melting point: 123°–129° C.; $R_f$: 0.55 (silica gel; petroleum ether/ethyl acetate/methanol=10:8:2); Calculated: C 65.12 H 6.33 N 23.98; Found: 64.96 6.20 23.95

(102) 4-[(3-Chloro-4-fluorophenyl)amino]-6-[trans-4-(2-(morpholinocarbonyl)ethyl)cyclohexylamino]pyrimido[5,4-d]pyrimidine Prepared from the compounds of Example XXXII and X, hydrolysis with sodium hydroxide solution and methanol and subsequent reaction with O-(benzotriazol-1-yl)-N,N,N', N'-tetramethyluronium tetrafluoroborate, triethylamine and morpholine. Melting point: 186°–191° C.; $R_f$: 0.48 (silica gel; petroleum ether/ethyl acetate/methanol=10:8:3); Calculated: C 58.42 H 5.69 N 19.08 Cl 6.90; Found: 58.47 5.68 18.77 7.09

(103) 4-[(3-Chloro-4-fluorophenyl)amino]-6-[3-piperidinylamino]pyrimido[5,4-d]pyrimidine Melting point: 194°–199° C.; $R_f$: 0.62 (alumina; methylene chloride/methanol=10:1)

(104) 4-[(3-Chloro-4-fluorophenyl)amino]-6-[4-acetylamino-1-piperidinyl]pyrimido[5,4-d]pyrimidine Prepared from the compounds of Example XXXII by reaction with 4-aminopiperidine and subsequent reaction with acetic anhydride. Melting point: 263°–265° C.; $R_f$: 0.63 (alumina; methylene chloride/methanol=20:1)

(105) 4-[(3-Chloro-4-fluorophenyl)amino]-6-(4-(dimethylaminocarbonyl)phenylamino[pyrimido[5,4-d]pyrimidine (106) 4-[(3-Chloro-4-fluorophenyl)amino]-6-[4-(acetylaminophenylamino]pyrimido[5,4-d]pyrimidine (107) 4-[(3-Chloro-4-fluorophenyl)amino]-6-[4-(dimethylaminocarbonylamino)phenylamino]pyrimido[5,4-d]pyrimidine (108) 4-[(3-Chloro-4-fluorophenyl)amino]-6-[4-(ethylamino-carbonylamino)phenylamino]pyrimido[5,4-d]pyrimidine (109) 4-[(3-Chloro-4-fluorophenyl)amino]-6-[4-(N-dimethylaminocarbonyl)-N-methylamino)phenylamino]pyrimido[5,4-d]pyrimidine (110) 4-((3-Chloro-4-fluorophenyl)amino]-6-[4-(3-oxo-1-piperazinyl)cyclohexylamino]pyrimido[5,4-d]pyrimidine (111) 4-[(3-Chloro-4-fluorophenyl)amino]-6-[4-(4-methyl-3-oxo-1-piperazinyl)cyclohexylamino]pyrimido[5,4-d]pyrimidine (112) 4-[(3-Chloro-4-fluorophenyl)amino]-6-[4-(methoxycarbonylamino)cyclohexylamino]pyrimido[5,4-d]pyrimidine (cis/trans mixture)

Prepared from the compounds of Example XXXII by reaction with cis/trans-1,4-diaminocyclohexane and subsequent reaction with methyl chloroformate. Melting point: 230°–235° C.; $R_f$: 0.53 (alumina; petroleum ether/ethyl acetate/methanol=10:10:2)

(113) 4-((3-Chloro-4-fluorophenyl)amino[-6-[4-(1-piperidinyl)cyclohexylamino]pyrimido[5,4-d]pyrimidine (114) 4-[(3-Chloro-4-fluorophenyl)amino]-6-[4-(1-piperazinyl)cyclohexylamino]pyrimido[5,4-d]pyrimidine (115) 4-(3-Chloro-4-fluorophenyl)amino]-6-[4-(4-dimethylamino-1-piperidinyl)cyclohexylamino]pyrimido[5,4-d]pyrimidine Prepared from the compounds of Example XXXII by reaction with 4-aminocyclohexanol, oxidation with Dess-Martin reagent and subsequent reductive amination with 4-dimethylaminopyridine and sodium cyanoborohydride. Melting point: 175° C. (decomposition); $R_f$: 0.44 (alumina; methylene chloride/ethyl acetate/methanol=10:5:1)

(116) 4-[(3-Chloro-4-fluorophenyl)amino]-6-[4-ethylaminocyclo-hexylamino]pyrimido[5,4-d]pyrimidine (117) 4-[(3-Chloro-4-fluorophenyl)amino]-6-[4-(4-amino-1-Piperidinyl)cyclohexylamino]pyrimido[5,4-d]pyrimidine (118) 4-[(3-Chloro-4-fluorophenyl)amino]-6-[4-cyanocyclohexylamino]pyrimido[5,4-d]pyrimidine (119) 4-[(3-Chloro-4-fluorophenyl)amino]-6-[4-(4-acetyl-1-piperazinyl)cyclohexylamino]pyrimido[5,4-d]pyrimidine (120) 4-[(3-Chloro-4-fluorophenyl)amino]-6-[4-(dimethylaminocarbonylamino)cyclohexylamino]pyrimido[5,4-d]pyrimidine (121) 4-[(3-Chloro-4-fluorophenyl)amino]-6-[4-(ethylamino-carbonylamino)cyclohexylamino]pyrimido[5,4-d]pyrimidine (122) 4-[(3-Chloro-4-fluorophenyl)amino]-6-[4-(benzoylamino)cyclohexylamino]pyrimido[5,4-d]pyrimidine (123) 4-[(3-Chloro-4-fluorophenyl)amino]-6-[4-(phenylsulphonylamino)cyclohexylamino]pyrimido[5,4-d]pyrimidine (124) 4-[(3-Chloro-4-fluorophenyl)amino]-6-[4-(phenylacetylamino)cyclohexylamino]pyrimido[5,4-d]pyrimidine (125) 4-[(3-Chloro-4-fluorophenyl)amino[-6-[4-(2-phenylpropionylamino)cyclohexylamino]pyrimido[5,4-d]pyrimidine (126) 4-[(3-Chloro-4-fluorophenyl)amino]-6-[4-(4-methyl-1-piperazinyl)carbonylcyclohexylamino]pyrimido[5,4-d]pyrimidine Prepared from 4-[(3-chloro-4-fluorop henyl)amino]-6-[trans-4-carboxycyclohexylamino]pyrimido[5,4-d]

pyrimidine by reaction with O-(benzotriazol-1-yl)-N,N,N', N'-tetramethyluronium tetrafluoroborate, triethylamine and 1-methylpiperazine. Melting point: 194°–197° C.; $R_f$: 0.45 (alumina; methylene chloride/methanol=10:0.3)

(127) 4-[(3-Chloro-4-fluorophenyl)amino]-6-[4-(1-piperazinyl)carbonylcyclohexylamino]pyrimido[5,4-d]pyrimidine Prepared from 4-[(3-chloro-4-fluorophenyl)amino]-6-[trans-4-carboxycyclohexylamino]pyrimido[5,4-d]pyrimidine by reaction with O-(benzotriazol-1-yl)-N,N,N', N'-tetramethyluronium tetrafluoroborate, triethylamine and piperazine. Melting point: 178°–182° C.; $R_f$: 0.47 (alumina; methylene chloride/methanol=10:0.3)

(128) 4-[(3-Chloro-4-fluorophenyl)amino]-6-[trans-4-(cis/trans-2,6-dimethylmorpholino)carbonylcyclohexylamino]pyrimido-[5,4-d]pyrimidine Prepared from 4-[(3-chloro-4-fluorophenyl)amino]-6-[trans-4-carboxycyclohexylamino]pyrimido[5,4-d]pyrimidine by reaction with O-(benzotriazol-1-yl)-N,N,N', N'-tetramethyluronium tetrafluoroborate, triethylamine and cis/trans-2,6-dimethylmorpholine. Melting point: 198°–201° C.; $R_f$: 0.40 and 0.33 (silica gel; petroleum ether/ethyl acetate/methanol=10:10:2) Calculated: C 58.42 H 5.69 N 19.08 Cl 6.90; Found: 58.47 5.68 18.77 7.09

(129) 4-[(3-Chloro-4-fluorophenyl)amino]-6-[4-(thiomorpholinocarbonyl)cyciohexylamino]pyrimido[5,4-d]pyrimidine (130) 4-[(3-Chloro-4-fluorophenyl)amino]-6-[4-(thiomorpholinocarbonyl S-oxide)cyclohexylamino]pyrimido[5,4-d]pyrimidine (131) 4-[(3-Chloro-4-fluorophenyl)amino]-6-[4-(thiomorpholinocarbonyl S,S-dioxide)cyclohexylamino]pyrimido[5,4-d]pyrimidine (132) 4-[(3-Chloro-4-fluorophenyl)amino]-6-[4-(4-acetyl-1-piperazinyl)carbonylcyclohexylamino]pyrimido[5,4-d]pyrimidine (133) 4-[(3-Chloro-4-fluorophenyl)amino]-6-[4-(1-piperidinylmethyl)cyclohexylamino]pyrimido[5,4-d]pyrimidine (134) 4-[(3-Chloro-4-fluorophenyl)amino]-6-[4-(1-pyrrolidinylmethyl)cyclohexylamino]pyrimido[5,4-d]pyrimidine (135) 4-[(3-Chloro-4-fluorophenyl)amino]-6-[4-(morpholinomethyl)cyclohexylamino]pyrimido[5,4-d]pyrimidine (136) 4-[(3-Chloro-4-fluorophenyl)amino]-6-[4-(1-piperazinylmethyl)cyclohexylamino]pyrimido[5,4-d]pyrimidine (137) 4-[(3-Chloro-4-fluorophenyl)amino]-6-[4-(4-methyl-1-piperazinylmethyl)cyclohexylamino]pyrimido[5,4-d]pyrimidine (138) 4-[(3-Chloro-4-fluorophenyl)amino]-6-[4-(methylaminomethyl)cyclohexylamino]pyrimido[5,4-d]pyrimidine (139) 4-[(3-Chloro-4-fluorophenyl)amino]-6-[4-(ethylamino-methyl)cyclohexylamino]pyrimido[5,4-d]pyrimidine (140) 4-[(3-Chloro-4-fluorophenyl)amino]-6-[4-(dimethylaminomethyl)cyclohexylamino]pyrimido[5,4-d]pyrimidine (141) 4-[(3-Chloro-4-fluorophenyl)amino]-6-[1-(2-aminoethyl)-4-piperidinylamino]pyrimido[5,4-d]pyrimidine (142) 4-[(3-Chloro-4-fluorophenyl)amino]-6-[1-(morpholinocarbonyl)-4-piperidinylamino]pyrimido[5,4-d]pyrimidine (143) 4-[(3-Chloro-4-fluorophenyl)amino]-6-[1-ethyl-3-piperidinylamino]pyrimido[5,4-d]pyrimidine (144) 4-[(3-Chloro-4-fluorophenyl)amino]-6-[3-aminocyclohexylamino]pyrimido[5,4-d]pyrimidine (145) 4-[(3-Chloro-4-fluorophenyl)amino]-6-[3-dimethylaminocyclohexylamino]pyrimido[5,4-d]pyrimidine (146) 4-[(3-Chloro-4-fluorophenyl)amino]-6-[4-(2-aminoethyl)cyclohexylamino]pyrimido[5,4-d]pyrimidine (147) 4-[(3-Chloro-4-fluorophenyl)amino]-6-[4-(tetrahydrothiopyranyl S-oxide)amino]pyrimido[5,4-d]pyrimidine (148) 4-[(3-Chloro-4-fluorophenyl)amino]-6-[4-(tetrahydrothiopyranyl S,S-dioxide)amino]pyrimido[5,4-d]pyrimidine (149) 4-[(3-Chloro-4-fluorophenyl)amino]-6-[4-(1-piperidinyl)-1-piperidinyl]pyrimido[5,4-d]pyrimidine (150) 4-[(3-Chloro-4-fluorophenyl)amino]-6-[4-(1-piperazinyl)-1-piperidinyl]pyrimido[5,4-d]pyrimidine Prepared from the compounds of Example XXXII by reaction with 4-hydroxypiperidine, oxidation with Dess-Martin reagent, subsequent reductive amination with 1-tert-butoxycarbonylpiperazin and sodium cyanoborohydride and subsequent reaction with trifluoroacetic acid. Melting point: 178°–180° C.; $R_f$: 0.35 (alumina; petroleum ether/ethyl acetate/methanol=10:5:3)

(151) 4-[(3-Chloro-4-fluorophenyl)amino]-6-[4-(4-methyl-1-piperazinyl)-1-piperidinyl]pyrimido[5,4-d]pyrimidine Prepared from the compounds of Example XXXII by reaction with 4-hydroxypiperidine, oxidation with Dess-Martin reagent and subsequent reductive amination with 1-methylpiperazine and sodium cyanoborohydride. Melting point: 163°–165° C.; $R_f$: 0.52 (alumina; petroleum ether/ethyl acetate/methanol=10:10:1)

(152) 4-[(3-Chloro-4-fluorophenyl)amino]-6-[4-(4-dimethylamino-1-piperidinyl)-1-piperidinyl]pyrimido[5,4-d]pyrimidine Prepared from the compounds of Example XXXII by reaction with 4-hydroxypiperidine, oxidation with Dess-Martin reagent and subsequent reductive amination with 4-dimethylaminopiperidine and sodium cyanoborohydride. Melting point: 160°–165° C.; $R_f$: 0.30 (alumina; petroleum ether/ethyl acetate/methanol=10:10:2)

(153) 4-[(3-Chloro-4-fluorophenyl)amino]-6-[4-methylamino-1-piperidinyl]pyrimido[5,4-d]pyrimidine Prepared from the compounds of Example XXXII by reaction with 4-hydroxypiperidine, oxidation with Dess-Martin reagent and subsequent reductive amination with methylamine and sodium cyanoborohydride. Melting point: 174°–176° C.; $R_f$: 0.40 (alumina; petroleum ether/ethyl acetate/methanol=10:10:4)

(154) 4-[(3-Chloro-4-fluorophenyl)amino]-6-[4-ethylamino-1-piperidinyl]pyrimido[5,4-d]pyrimidine (155) 4-[(3-Chloro-4-fluorophenyl)amino]-6-[4-(morpholinocarbonylamino)-1-piperidinyl]pyrimido[5,4-d]pyrimidine (156) 4-[(3-Chloro-4-fluorophenyl)amino]-6-[4-(4-amino-1-piperidinyl)-1-piperidinyl]pyrimido[5,4-d]pyrimidine (157) 4-[(3-Chloro-4-fluorophenyl)amino]-6-[4-methoxy-1-piperidinyl]pyrimido[5,4-d]pyrimidine (158) 4-[(3-Chloro-4-fluorophenyl)amino]-6-[4-(2-oxo-1-pyrrolidinyl)-1-piperidinyl]pyrimido[5,4-d]pyrimidine (159) 4-[(3-Chloro-4-fluorophenyl)amino]-6-[4-(4-hydroxy-1-piperidinyl)-1-piperidinyl]pyrimido[5,4-d]pyrimidine (160) 4-[(3-Chloro-4-fluorophenyl)amino]-6-(4-(4-methylamino-1-piperidinyl)-1-piperidinyl]pyrimido[5,4-d]pyrimidine (161) 4-[(3-Chloro-4-fluorophenyl)amino]-6-[4-(3-oxo-1-piperazinyl)-1-piperidinyl]pyrimido[5,4-d]pyrimidine (162) 4-[(3-Chloro-4-fluorophenyl)amino]-6-[4-(4-methyl-3-oxo-1-piperazinyl)-1-piperidinyl]pyrimido[5,4-d]pyrimidine (163) 4-[(3-Chloro-4-fluorophenyl)amino]-6-[4-(N-acetyl-N-methylamino)-1-piperidinyl]pyrimido[5,4-d]pyrimidine (164) 4-[(3-Chloro-4-fluorophenyl)amino]-6-[4-(N-methyl-N-methylsulphonylamino)-1-piperidinyl]pyrimido[5,4-d]pyrimidine Prepared from Compound 153 in Example 1 by reaction with methanesulphonyl chloride and triethylamine. Melting point: 225°–227° C.; $R_f$: 0.53 (alumina; petroleum ether/ethyl acetate/methanol=10:10:1); Calculated: C 48.97 H 4.54 N 21.04; Found: 49.07 4.59 20.75

(165) 4-[(3-Chloro-4-fluorophenyl)amino]-6-(4-(2-methoxycarbonylethyl)-1-piperidinyl]pyrimido[5,4-d]pyrimidine (166) 4-[(3-Chloro-4-fluorophenyl)amino]-6-[4-(2-carboxyethyl)-1-piperidinyl]pyrimido[5,4-d]pyrimidine (167) 4-[(3-Chloro-4-fluorophenyl)amino]-6-[4-(2-(morpholinocarbonyl)ethyl)-1-piperidinyl]pyrimido[5,4-d]pyrimidine (168) 4-[(3-Chloro-4-fluorophenyl)amino]-6-[4-(2-aminoethyl)-1-piperidinyl]pyrimido[5,4-d]pyrimidine (169) 4-[(3-Chloro-4-fluorophenyl)amino]-6-[4-(2-aminocarbonylethyl)-1-piperidinyl]pyrimido[5,4-d]pyrimidine (170) 4-[(3-Chloro-4-fluorophenyl)amino]-6-[4-(2-methylaminocarbonylethyl)-1-piperidinyl]pyrimido[5,4-d]pyrimidine (171) 4-[(3-Chloro-4-fluorophenyl)amino]-6-[4-(2-dimethylaminocarbonylethyl)-1-piperidinyl]pyrimido[5,4-d]pyrimidine (172) 4-[(3-Chloro-4-fluorophenyl)amino]-6-[4-(2-(pyrrolidinocarbonyl)ethyl)-1-piperidinyl]pyrimido[5,4-d]pyrimidine (173) 4-[(3-Chloro-4-fluorophenyl)amino]-6-[4-(carboxymethyloxy)-1-piperidinyl]pyrimido[5,4-d]pyrimidine (174) 4-[(3-Chloro-4-fluorophenyl)amino]-6-[4-(methoxycarbonylmethyloxy)-1-piperidinyl]pyrimido[5,4-d]pyrimidine (175) 4-[(3-Chloro-4-fluorophenyl)amino]-6-[4-(aminocarbonylmethyloxy)-1-piperidinyl]pyrimido[5,4-d]pyrimidine (176) 4-[(3-Chloro-4-fluorophenyl)amino]-6-[4-(methylaminocarbonylmethyloxy)-1-piperidinyl]pyrimido[5,4-d]pyrimidine (177) 4-[(3-Chloro-4-fluorophenyl)amino]-6-[4-(dimethylamino-carbonylmethyloxy)-1-piperidinyl]pyrimido[5,4-d]pyrimidine (178) 4-[(3-Chloro-4-fluorophenyl)amino]-6-[4-(morpholino-carbonylmethyloxy)-1-piperidinyl]pyrimido[5,4-d]pyrimidine (179) 4-[(3-Chloro-4-fluorophenyl)amino]-6-[4-((1-pyrrolidinyl)carbonylmethyloxy)-1-piperidinyl]pyrimido[5,4-d]pyrimidine (180) 4-[(3-Chloro-4-fluorophenyl)amino]-6-[2-aminomethyl-1-piperidinyl]pyrimido[5,4-d]pyrimidine (181) 4-[(3-Chloro-4-fluorophenyl)amino]-6-[2-(1-pyrrolidinyl)-methyl-1-piperidinyl]pyrimido[5,4-d]pyrimidine (182) 4-[(3-Chloro-4-fluorophenyl)amino]-6-[2-dimethylaminomethyl-1-piperidinyl]pyrimido[5,4-d]pyrimidine (183) 4-[(3-Chloro-4-fluorophenyl)amino]-6-[4-amino-4-methyl-1-piperidinyl]pyrimido[5,4-d]pyrimidine Prepared from the compounds of Examples XXXII and Compound 2 of Example XXXVI. Melting point: 188°–190° C.; $R_f$: 0.50 (silica gel; methylene chloride/methanol/concentrated ammonia=9:1:0.1)

(184) 4-[(3-Chloro-4-fluorophenyl)amino]-6-[endo-3-amino-8-azabicyclo[3.2.1]-8-octyl]pyrimido[5,4-d]pyrimidine Prepared from the compounds of Examples XXXII and XXXVI. Melting point: 238°–240° C.; $R_f$: 0.34 (silica gel; methylene chloride/methanol/concentrated ammonia=9:1:0.1)

(185) 4-[(3-Chloro-4-fluorophenyl)amino]-6-[3-methylamino-8-azabicyclo[3.2.1]-8-octyl]pyrimido[5,4-d]pyrimidine (186) 4-[(3-Chloro-4-fluorophenyl)amino]-6-[3-dimethylamino-8-azabicyclo[3.2.1]-8-octyl]pyrimido[5,4-d]pyrimidine (187) 4-[(3-Chloro-4-fluorophenyl)amino]-6-[endo-3-acetylamino-8-azabicyclo[3.2.1]-8-octyl]pyrimido[5,4-d]pyrimidine Prepared from Compound 184 of Example 1 by reaction with acetic anhydride and triethylamine. Melting point: 214°–216° C.; $R_f$: 0.53 (silica gel; methylene chloride/methanol/concentrated ammonia=9:1:0.1)

(188) 4-[(3-Chloro-4-fluorophenyl)amino]-6-[3-acetylaminomethyl-1-piperidinyl]pyrimido[5,4-d]pyrimidine (189) 4-[(3-Chloro-4-fluorophenyl)amino]-6-[3-methylsulphonyl-aminomethyl-1-piperidinyl]pyrimido[5,4-d]pyrimidine (190) 4-[(3-Chloro-4-fluorophenyl)amino]-6-[4-ethylaminomethyl-1-piperidinyl]pyrimido[5,4-d]pyrimidine (191) 4-[(3-Chloro-4-fluorophenyl)amino]-6-[4-methylaminomethyl-1-piperidinyl]pyrimido[5,4-d]pyrimidine (192) 4-[(3-Chloro-4-fluorophenyl)amino]-6-[4-(1-piperidinyl)-methyl-1-piperidinyl]pyrimido[5,4-d]pyrimidine (193) 4-[(3-Chloro-4-fluorophenyl)amino]-6-[4-(1-piperazinyl)-methyl-1-piperidinyl]pyrimido[5,4-d]pyrimidine (194) 4-[(3-Chloro-4-fluorophenyl)amino]-6-[4-(4-methyl-1-piperazinyl)methyl-1-piperidinyl]pyrimido[5,4-d]pyrimidine Prepared from the compounds of Examples XXXII and XXXIV, subsequent oxidation with Dess-Martin reagent and subsequent reductive amination with 1-methylpiperazine and sodium cyanoborohydride. Melting point: 138°–140° C.; $R_f$: 0.55 (alumina; petroleum ether/ethyl acetate/methanol=10:10:1)

(195) 4-[(3-Chloro-4-fluorophenyl)amino]-6-[4-(morpholinomethyl)-1-piperidinyl]pyrimido[5,4-d]pyrimidine (196) 4-[(3-Chloro-4-fluorophenyl)amino]-6-[4-(1-pyrrolidinyl)-methyl-1-piperidinyl]pyrimido[5,4-d]pyrimidine (197) 4-[(3-Chloro-4-fluorophenyl)amino]-6-[4-dimethylaminomethyl-1-piperidinyl]pyrimido[5,4-d]pyrimidine (198) 4-[(3-Chloro-4-fluorophenyl)amino]-6-[4-acetylaminomethyl-1-piperidinyl]pyrimido[5,4-d]pyrimidine (199) 4-[(3-Chloro-4-fluorophenyl)amino]-6-[4-methylsulphonyl-aminomethyl-1-piperidinyl]pyrimido[5,4-d]pyrimidine (200) 4-[(3-Chloro-4-fluorophenyl)amino]-6-[4-cyanomethyl-1-piperidinyl]pyrimido[5,4-d]pyrimidine (201) 4-[(3-Chloro-4-fluorophenyl)amino]-6-[4-(1-piperazinyl)-carbonyl-1-piperidinyl]pyrimido[5,4-d]pyrimidine (202) 4-[(3-Chloro-4-fluorophenyl)amino]-6-[4-(4-methyl-1-piperazinyl)carbonyl-1-piperidinyl]pyrimido[5,4-d]pyrimidine
(203) 4-[(3-Chloro-4-fluorophenyl)amino]-6-[4-(2-oxo-1-imidazolidinyl)-1-piperidinyl]pyrimido[5,4-d]pyrimidine
(204) 4-[(3-Chloro-4-fluorophenyl)amino]-6-(4-(3-methyl-2-oxo-1-imidazolidinyl)-1-piperidinyl]pyrimido[5,4-d]pyrimidine
(205) 4-[(3-Chloro-4-fluorophenyl)amino]-6-[2-(3-oxo-1-piperazinyl)ethylamino]pyrimido[5,4-d]pyrimidine
(206) 4-[(3-Chloro-4-fluorophenyl)amino]-6-[2-(4-methyl-3-oxo-1-piperazinyl)ethylamino]pyrimido[5,4-d]pyrimidine
(207) 4-[(3-Chloro-4-fluorophenyl)amino]-6-[2-cyanoethylamino]-pyrimido[5,4-d]pyrimidine
(208) 4-[(3-Chloro-4-fluorophenyl)amino]-6-[2-(1-methyl-2-piperidinyl)ethylamino]pyrimido[5,4-d]pyrimidine
(209) 4-[(3-Chloro-4-fluorophenyl)amino]-6-[N-methyl-N-(2-(1-methyl-2-piperidinyl)ethyl)amino]pyrimido[5,4-d]pyrimidine
(210) 4-[(3-Chloro-4-fluorophenyl)amino]-6-[2-(4-piperidinyl)-ethylamino]pyrimido[5,4-d]pyrimidine
(211) 4-[(3-Chloro-4-fluorophenyl)amino]-6-[2-(2-oxo-1-imidazolidinyl)ethylamino]pyrimido[5,4-d]pyrimidine
(212) 4-[(3-Chloro-4-fluorophenyl)amino]-6-[2-(3-methyl-2-oxo-1-imidazolidinyl)ethylamino]pyrimido[5,4-d]pyrimidine
(213) 4-[(3-Chloro-4fluorophenyl)amino]-6-[2-(1-acetyl-4-piperidinyl)ethylamino]pyrimido[5,4-d]pyrimidine
(214) 4-[(3-Chloro-4-fluorophenyl)amino]-6-[2-(1-methoxycarbon-yl-4-piperidinyl)ethylamino]pyrimido[5,4-d]pyrimidine
(215) 4-[(3-Chloro-4-fluorophenyl)amino]-6-[2-(4-aminocyclohexyl)ethylamino]pyrimido[5,4-d]pyrimidine
(216) 4-[(3-Chloro-4-fluorophenyl)amino]-6-[3-acetylamino-propylamino]pyrimido[5,4-d]pyrimidine
(217) 4-[(3-Chloro-4-fluorophenyl)amino]-6-[3-methylsulphonyl-aminopropylamino]pyrimido[5,4-d]pyrimidine
(218) 4-[(3-Chloro-4-fluorophenyl)amino]-6-[3-methoxycarbonylaminopropylamino]pyrimido[5,4-d]pyrimidine
(219) 4-[(3-Chloro-4-fluorophenyl)amino]-6-[3-(morpholinocarbonylamino)propylamino]pyrimido[5,4-d]pyrimidine
(220) 4-[(3-Chloro-4-fluorophenyl)amino]-6-[1-piperazinylcarbonylmethylamino]pyrimido[5,4-d]pyrimidine
(221) 4-[(3-Chloro-4-fluorophenyl)amino]-6-[4-methyl-1-piperazinylcarbonylmethylamino]pyrimido[5,4-d]pyrimidine
(222) 4-[(3-Chloro-4-fluorophenyl)amino]-6-[4-acetyl-1-piperazinylcarbonylmethylamino]pyrimido[5,4-d]pyrimidine
(223) 4-[(3-Chloro-4-fluorophenyl)amino]-6-[1-carboxyethylamino]pyrimido[5,4-d]pyrimidine
(224) 4-[(3-Chloro-4-fluorophenyl)amino]-6-[1-methoxycarbonylethylamino]pyrimido[5,4-d]pyrimidine
(225) 4-[(3-Chloro-4-fluorophenyl)amino]-6-[1-aminocarbonylethylamino]pyrimido[5,4-d]pyrimidine
(226) 4-[(3-Chloro-4-fluorophenyl)amino]-6-[1-methylaminocarbonylethylamino]pyrimido[5,4-d]pyrimidine
(227) 4-[(3-Chloro-4-fluorophenyl)amino[-6-[1-dimethylaminocarbonylethylamino]pyrimido[5,4-d]pyrimidine
(228) 4-[(3-Chloro-4-fluorophenyl)amino]-6-[1-(1-pyrrolidinylcarbonyl)ethylamino]pyrimido[5,4-d]pyrimidine
(229) 4-[(3-Chloro-4-fluorophenyl)amino]-6-[1-(morpholinocarbonyl)ethylamino]pyrimido[5,4-d]pyrimidine
(230) 4-[(3-Chloro-4-fluorophenyl)amino]-6-[1-(1-piperazinylcarbonyl)ethylamino]pyrimido[5,4-d]pyrimidine
(231) 4-[(3-Chloro-4-fluorophenyl)amino]-6-[1-(4-methyl-1-piperazinylcarbonyl)ethylamino]pyrimido[5,4-d]pyrimidine
(232) 4-[(3-Chloro-4-fluorophenyl)amino]-6-[1-(4-acetyl-1-piperazinylcarbonyl)ethylamino]pyrimido[5,4-d]pyrimidine
(233) 4-[(3-Chloro-4-fluorophenyl)amino]-6-[2-(1-piperazinylcarbonyl)-2-propylamino]pyrimido[5,4-d]pyrimidine
(234) 4-[(3-Chloro-4-fluorophenyl)amino]-6-[2-(4-methyl-1-piperazinylcarbonyl)-2-propylamino]pyrimido[5,4-d]pyrimidine
(235) 4-[(3-Chloro-4-fluorophenyl)amino]-6-[2-(4-acetyl-1-piperazinylcarbonyl)-2-propylamino]pyrimido[5,4-d]pyrimidine
(236) 4-[(3-Chloro-4-fluorophenyl)amino]-6-[1-(morpholinocarbonyl)-3-pyrrolidinylamino]pyrimido[5,4-d]pyrimidine
(237) 4-[(3-Chloro-4-fluorophenyl)amino]-6-[3-aminocyclopentylamino]pyrimido[5,4-d]pyrimidine
(238) 4-[(3-Chloro-4-fluorophenyl)amino]-6-(3-methoxycarbonylcyclopentylamino)pyrimido[5,4-d]pyrimidine
(239) 4-[(3-Chloro-4-fluorophenyl)amino]-6-[3-carboxycyclopentylamino]pyrimido[5,4-d]pyrimidine
(240) 4-[(3-Chloro-4-fluorophenyl)amino]-6-[3-(morpholinocarbonyl)cyclopentylamino]pyrimido[5,4-d]pyrimidine
(241) 4-[(3-Chloro-4-fluorophenyl)amino]-6-[1-ethyl-2-pyrrolidinylmethylamino]pyrimido[5,4-d]pyrimidine
(242) 4-[(3-Chloro-4-fluorophenyl)amino]-6-[1-ethyl-3-pyrrolidinylmethylamino]pyrimido[5,4-d]pyrimidine
(243) 4-[(3-Chloro-4-fluorophenyl)amino]-6-[(3-aminomethylcyclopentyl)methylamino]pyrimido[5,4-d]pyrimidine
(244) 4-[(3-Chloro-4-fluorophenyl)amino]-6-[3-tetrahydrofurylmethylamino]pyrimido[5,4-d]pyrimidine
(245) 4-[(3-Chloro-4-fluorophenyl)amino]-6-[3-methylamino-1-pyrrolidinyl]pyrimido[5,4-d]pyrimidine
(246) 4-[(3-chloro-4-fluorophenyl)amino]-6-(3-ethylamino-1-pyrrolidinyl]pyrimido[5,4-d]pyrimidine
(247) 4-[(3-Chloro-4-fluorophenyl)amino]-6-[1-(morpholinocarbonyl)-4-piperidinylmethylamino]pyrimido[5,4-d]pyrimidine
(248) 4-[(3-Chloro-4-fluorophenyl)amino]-6-[1-acetyl-4-piperidinylmethylamino]pyrimido[5,4-d]pyrimidine
(249) 4-[(3-Chloro-4-fluorophenyl)amino]-6-[1-methyl-4-piperidinylmethylamino]pyrimido[5,4-d]pyrimidine
(250) 4-[(3-Chloro-4-fluorophenyl)amino]-6-[3-piperidinylmethylamino]pyrimido[5,4-d]pyrimidine
(251) 4-[(3-Chloro-4-fluorophenyl)amino]-6-[2-piperidinylmethylamino]pyrimido[5,4-d]pyrimidine
(252) 4-[(3-Chloro-4-fluorophenyl)amino]-6-[1-amino-2-propylamino]pyrimido[5,4-d]pyrimidine
(253) 4-[(3-Chloro-4-fluarophenyl)amino]-6-[4-(morpholinocarbonyl)-1-piperazinyl]pyrimido[5,4-d]pyrimidine
(254) 4-[(3-Chloro-4-fluorophenyl)amino]-6-[N-methyl-N-(4-piperidinyl)amino]pyrimido[5,4-d]pyrimidine
(255) 4-[(3-Cyanophenyl)amino]-6-[N-methyl-N-(1-methyl-4-piperidinyl)amino]pyrimido[5,4-d]pyrimidine Melting point: 199°–204° C.; $R_f$: 0.49 (alumina; ethyl acetate/petroleum ether/methanol=10:3:0.4)

(256) 4-[(3-Trifluoromethoxyphenyl)amino]-6-[N-methyl-N-(1-methyl-4-piperidinyl)amino]pyrimido[5,4-d]pyrimidine Melting point: 199°–204° C.; $R_f$: 0.49 (alumina; ethyl acetate/petroleum ether/methanol=10:10:2)

(257) 4-[(3-Trifluoromethylphenyl)amino]-6-[N-methyl-N-(1-methyl-4-piperidinyl)amino]pyrimido[5,4-d]pyrimidine Melting point: 129°–132° C.; $R_f$: 0.50 (alumina; ethyl acetate/petroleum ether=10:3)

(258) 4-[(3,4-Difluorophenyl)amino]-6-[N-methyl-N-(1-methyl-4-piperidinyl)amino]pyrimido[5,4-d]pyrimidine Melting point: 196°–198° C.; $R_f$: 0.59 (alumina; ethyl acetate/petroleum ether/methanol=10:5:0.4)

(259) 4-[(3-Nitrophenyl)amino]-6-[N-methyl-N-(1-methyl-4-piperidinyl)amino]pyrimido[5,4-d]pyrimidine Melting point: 199°–203° C.; $R_f$: 0.36 (silica gel; methylene chloride/methanol=10:1)

(260) 4-[(3-Ethynylphenyl)amino]-6-[N-methyl-N-(1-methyl-4-piperidinyl)amino]pyrimido[5,4-d]pyrimidine Melting point: 162°–165° C.; $R_f$: 0.64 (silica gel; petroleum ether/ethyl acetate/methanol=10:5:1)

(261) 4-[(4-Amino-3-nitrophenyl)amino]-6-[N-methyl-N-(1-methyl-4-piperidinyl)amino]pyrimido[5,4-d]pyrimidine Melting point: 242°–246° C.; $R_f$: 0.63 (silica gel; methylene chloride/methanol/concentrated ammonia=10:2:0.05)

(262) 4-[(4-Chloro-3-nitrophenyl)amino]-6-[N-methyl-N-(1-methyl-4-piperidinyl)amino]pyrimido[5,4-d]pyrimidine Melting point: 210°–215° C.; $R_f$: 0.36 (silica gel; methylene chloride/methanol=10:1)

(263) 4-[(3-Chloro-4-fluorophenyl)amino]-6-[exo-3-amino-8-azabicyclo[3.2.1]-8-octyl]pyrimido[5,4-d]pyrimidine Prepared from the compounds of Examples XXXII and XXXVI. Melting point: 178°–180° C.; $R_f$: 0.41 (silica gel; methylene chloride/methanol/concentrated ammonia= 9:1:0.1)

(264) 4-[(3-Trifluoromethoxyphenyl)amino]-6-[trans-4-hydroxycyclohexylamino]pyrimido[5,4-d]pyrimidine Melting point: 224°–226° C.; $R_f$: 0.41 (silica gel; petroleum ether/ethyl acetate/methanol=10:10:2)

(265) 4-[(3-Chloro-4-fluorophenyl)amino]-6-[1-amino-2-methyl-2-propylamino]pyrimido[5,4-d]pyrimidine Prepared from the compounds of Examples XXXII and Compound 1 of Example XII and subsequent reaction with trifluoroacetic acid. Melting point: 196°–201° C.; $R_f$: 0.43 (alumina; methylene chloride/methanol=10:1)

(266) 4-[(4-Phenoxyphenyl)amino]-6-[1-piperidinyl]pyrimido-[5,4-d]pyrimidine

Melting point: 175° C.; $R_f$: 0.84 (silica gel; petroleum ether/ethyl acetate/methanol=10:8:2) (267) 4-[(4-Phenoxyphenyl)amino]-6-morpholinopyrimido-[5,4-d]pyrimidine Melting point: 212° C.; $R_f$: 0.69 (silica gel; petroleum ether/ethyl acetate/methanol=10:8:2)

(268) 4-[(4-Phenoxyphenyl)amino]-6-[trans-4-hydroxycyclohexylamino]pyrimido[5,4-d]pyrimidine Melting point: 206° C.; $R_f$: 0.36 (silica gel; petroleum ether/ethyl acetate/methanol=10:8:2)

(269) 4-[(4-Benzyloxyphenyl)amino]-6-[trans-4-hydroxycyclohexylamino]pyrimido[5,4-d]pyrimidine Melting point: 217° C.; $R_f$: 0.37 (silica gel; petroleum ether/ethyl acetate/methanol=10:8:2)

(270) 4-[(4-Phenoxyphenyl)amino]-6-[1-methyl-4-piperidinylamino]pyrimido[5,4-d]pyrimidine Melting point: 157° C.; $R_f$: 0.58 (alumina; methylene chloride/ethyl acetate/methanol=10:3:1)

(271) 4-[(4-Benzyloxyphenyl)amino]-6-[1-piperidinyl]pyrimido[5,4-d]pyrimidine

Melting point: 165° C.; $R_f$: 0.60 (silica gel; petroleum ether/ethyl acetate/methanol=10:5:1)

(272) 4-[(4-Benzyloxyphenyl)amino]-6-morpholinopyrimido[5,4-d]pyrimidine

Melting point: 152° C.; $R_f$: 0.51 (silica gel; petroleum ether/ethyl acetate/methanol=10:8:2)

(273) 4-[(4-Benzyloxyphenyl)amino]-6-[2-hydroxyethylamino]pyrimido[5,4-d]pyrimidine Melting point: 216° C.

(274) 4-[(4-Benzyloxyphenyl)amino]-6-[tetrahydrofurfurylamino]pyrimido[5,4-d]pyrimidine Melting point: 178° C.

(275) 4-[(4-Benzyloxyphenyl)amino]-6-[trans-4-dimethylamino-cyclohexylamino]pyrimido[5,4-d]pyrimidine Prepared from the compounds of Examples XXXII and XLVI. Melting point: 155° C.; $R_f$: 0.56 (alumina; methylene chloride/ethyl acetate/methanol=10:3:1)

(276) 4-[(4-Benzyloxyphenyl)amino]-6-[4-amino-1-piperidinyl]pyrimido[5,4-d]pyrimidine Melting point: 150° C.; $R_f$: 0.26 (alumina; methylene chloride/ethyl acetate/methanol=10:3:1)

(277) (3'S)-4-[3-Chlorophenylamino]-6-[(3'-quinuclidinyl)amino]pyrimido[5,4-d]pyrimidine Melting point: 129°–132° C.; $R_f$: 0.26 (alumina; methylene chloride/ethyl acetate/methanol=10:3:1)

(278) 4-[(3-Chloro-4-fluorophenyl)amino]-6-[1-dimethylaminocarbonyl-4-piperidinylamino]pyrimido[5,4-d]pyrimidine Prepared from 4-[(3-chloro-4-fluorophenyl)amino]-6-[1-tertbutyloxycarbonyl-4-piperidinylamino]pyrimido[5,4-d]pyrimidine by reaction with trifluoroacetic acid and subsequent reaction with dimethylcarbamoyl chloride and triethylamine. Melting point: 187°–188° C.; $R_f$: 0.59 (alumina; petroleum ether/ethyl acetate/methanol=10:10:2)

(279) rac-4-[(3-Chloro-4-fluorophenyl)amino]-6-[1-methyl-3-piperidinylamino]pyrimido[5,4-d]pyrimidine Prepared from the compounds of Examples XXXII and XLVII, subsequent reaction with trifluoroacetic acid and subsequent reaction with sodium cyanoborohydride and formaldehyde. Melting point: 142°–146° C.; $R_f$: 0.27 (silica gel; petroleum ether/ethyl acetate/methanol=10:10:4)

(280) 4-[(4-Benzyloxy-3-chlorophenyl)amino]-6-[trans-4-di-methylaminocyclohexylamino]pyrimido[5,4-d]pyrimidine Prepared from the compounds of Examples XXXII and XLII. Melting point: 154°–156° C.; $R_f$: 0.40 (alumina; petroleum ether/ethyl acetate/methanol=10:10:2)

(281) 4-[(4-Phenoxy-3-chlorophenyl)amino]-6-[trans-4-di-methylaminocyclohexylamino]pyrimido[5,4-d]pyrimidine Prepared from the compounds of Examples XXXII and XLII. Melting point: 126°–128° C.; $R_f$: 0.48 (alumina; petroleum ether/ethyl acetate/methanol=10:10:0.5)

(282) (3'S)-4-[(3-Chloro-4-fluorophenyl)amino]-6-[(3'-quinuclidinyl)amino]pyrimido[5,4-d]pyrimidine Melting point: 171°–173° C.; $R_f$: 0.38 (alumina; petroleum ether/ethyl acetate/methanol=10:10:2); $[\alpha]_D^{20}$=−38.2 (c=1.0 in methylene chloride/methanol=2:1)

(283) (3'R)-4-[(3-Chloro-4-fluorophenyl)amino]-6-[(3'-quinuclidinyl)amino]pyrimido[5,4-d]pyrimidine Melting point: 162°–164° C.; $R_f$: 0.39 (alumina; petroleum ether/ethyl acetate/methanol=10:10:2); $[\alpha]_D^{20}$=+36.6(c=1.0 in methylene chloride/methanol=2:1)

EXAMPLE 2

4-(1-Indolinyl)-6-morpholino-pyrimido[5,4-d]pyrimidine 0.30 g of 4-chloro-6-(morpholino)pyrimido[5,4-d]pyrimidine, 0.28 g of indoline and 5 ml of butanol are heated at 110° C. for 3 hours. The solvent is distilled off in a rotary evaporator, and the residue is triturated with water, filtered off with suction and purified by chromatography on a silica gel column with petroleum ether/ethyl acetate (5:8).

Yield: 0.23 g (57% of theory), Melting point: 150°–152° C.; $R_f$: 0.48 (silica gel; petroleum ether/ethyl acetate=5:10); Calculated: C 64.65 H 5.42 N 25.13; Found: 64.69 5.47 25.08

The following compound is obtained in analogy to Example 2:

(1) 4-(1,2,3,4-Tetrahydroquinolin-1-yl)-6-morpholinopyrimido[5,4-d]pyrimidineo

Melting point: 105°–107° C.; $R_f$: 0.27 (silica gel; petroleum ether/ethyl acetate=1:1); Prepared from the compound of Example III and 1,2,3,4-tetrahydroquinoline.

EXAMPLE 3

Coated tablets with 75 mg of active substance

| 1 Tablet core contains: | |
| --- | --- |
| Active substance | 75.0 mg |
| Calcium phosphate | 93.0 mg |
| Maize starch | 35.5 mg |
| Polyvinylpyrrolidone | 10.0 mg |
| Hydroxypropylmethylcellulose | 15.0 mg |
| Magnesium stearate | 1.5 mg |
| | 230.0 mg |

Production:

The active substance is mixed with calcium phosphate, maize starch, polyvinylpyrrolidone, hydroxypropylmethylcellulose an half of the stated amount of magnesium stearate. Slugs with a diameter of about 13 mm are produced in a tabletting machine and are rubbed through a screen with a mesh width of 1.5 mm in a suitable machine and are mixed with the remaining amount of magnesium stearate. These granules are compressed to tablets the required shaped in a tabletting machine.

Core weight: 230 mg

Punch: 9 mm, convex

The tablet cores produced in this way are coated with a film essentially consisting of hydroxypropylmethylcellulose. The finished film-coated tablets are polished with beeswax.

Coated tablet weight: 245 mg

EXAMPLE 4

Tablets with 100 mg of active substance

| Composition: | |
| --- | --- |
| 1 Tablet contains: | |
| Active substance | 100.0 mg |
| Lactose | 80.0 mg |
| Maize starch | 34.0 mg |
| Polyvinylpyrrolidone | 4.0 mg |
| Magnesium stearate | 2.0 mg |
| | 220.0 mg |

Production process:

Active substance, lactose and starch are mixed and moistened uniformly with an aqueous solution of polyvinylpyrrolidone. After the moist composition has been screened (mesh width 2.0 mm) and dried on trays in an oven at 50° C., it is screened again (mesh width 1.5 mm) and the lubricant is mixed in. The mixture ready for compression is converted into tablets.

Tablet weight: 220 mg

Diameter: 10 mm, biplanar with bevel on both sides and score on one side.

EXAMPLE 5

Tablets with 150 mg of active substance

| Composition: | |
| --- | --- |
| 1 Tablet contains: | |
| Active substance | 150.0 mg |
| Lactose powder | 89.0 mg |
| Maize starch | 40.0 mg |
| Colloidal silica | 10.0 mg |
| Polyvinylpyrrolidone | 10.0 mg |
| Magnesium stearate | 1.0 mg |
| | 300.0 mg |

Production:

The active substance is mixed with lactose, maize starch and silica, moistened with a 20% aqueous polyvinylpyrrolidone solution and forced through a screen with a mesh width of 1.5 mm.

The granules are dried at 45° C. and again rubbed through the same screen and mixed with the stated amount of magnesium stearate. Tablets are compressed from the mixture.

Tablet weight: 300 mg

Punch: 10 mm, planar

EXAMPLE 6

Hard gelatin capsules with 150 mg of active substance

| 1 Capsule contains: | | |
| --- | --- | --- |
| Active substance | | 150.0 mg |
| Maize starch, dry | ca. | 180.0 mg |
| Lactose powder | ca. | 87.0 mg |
| Magnesium stearate | | 3.0 mg |
| | ca. | 420.0 mg |

Production:

The active substance is mixed with the ancillary substances, passed through a screen with a mesh width of 0.75 mm and mixed homogeneously in a suitable apparatus. The finaial mixture is packed into hard gelatin capsules of size 1.

Capsule contents: about 320 mg

Capsule shell: hard gelatin capsule size 1.

EXAMPLE 7

Suppositories with 150 mg of active substance

| 1 Suppository contains: | |
| --- | --- |
| Active substance | 150.0 mg |
| Polyethylene glycol 1500 | 550.0 mg |
| Polyethylene glycol 6000 | 460.0 mg |

-continued

| 1 Suppository contains: | |
|---|---|
| Polyoxyethylene sorbitan monostearate | 840.0 mg |
| | 2,000.0 mg |

Production:

After the suppository base has been melted, the active substance is homogeneously dispersed therein and the melt is poured into cooled molds.

EXAMPLE 8

Suspension with 50 mg of active substance

| 100 ml of suspension contain: | | |
|---|---|---|
| Active substance | | 1.00 g |
| Carboxymethylcellulose Na salt | | 0.10 g |
| Methyl p-hydroxybenzoate | | 0.05 g |
| Propyl p-hydroxybenzoate | | 0.01 g |
| Sucrose | | 10.00 g |
| Glycerol | | 5.00 g |
| Sorbitol solution, 70% strength | | 20.00 g |
| Flavouring | | 0.30 g |
| Distilled water | ad | 100 ml |

Production:

Distilled water is heated to 70° C. Methyl and propyl p-hydroxybenzoates, and glycerol and carboxymethylcellulose sodium salt are dissolved therein with stirring. The solution is cooled to room temperature and, while stirring, the active substance is added and homogeneously dispersed. After the sugar, the sorbitol solution and the flavouring have been added and dissolved, the suspension is evacuated with stirring for deaeration.

5 ml of suspension contain 50 mg of active substance.

EXAMPLE 9

Ampoules with 10 mg of active substance

| Composition: | | |
|---|---|---|
| Active substance | | 10.0 mg |
| 0.01 N hydrochloric acid q.s. | | |
| Doubled-distilled water | ad | 2.0 ml |

Production:

The active substance is dissolved in the required amount of 0.01N HCl, made isotonic with sodium chloride, sterilized by filtration and dispensed into 2 ml ampoules.

EXAMPLE 10

Ampoules with 50 mg of active substance

| Composition: | | |
|---|---|---|
| Active substance | | 50.0 mg |
| 0.01 N hydrochloric acid q.s. | | |
| Doubled-distilled water | ad | 10.0 ml |

Production:

The active substance is dissolved in the required amount of 0.01N HCl, made isotonic with sodium chloride, sterilized by filtration and dispensed into 10 ml ampoules.

What is claimed is:

1. A compound of the formula I

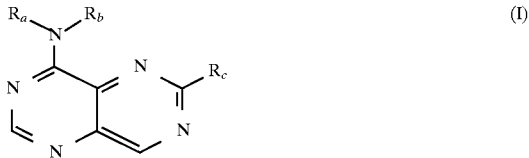

wherein, $R_a$ denotes a hydrogen atom, $R_b$ denotes a 3-chlorophenyl, 3-chloro-4-fluorophenyl, 3-(1,1,2,2-tetrafluoroethoxy)phenyl, 4-amino-3,5-dibromophenyl, 4-amino-3,5-dichlorophenyl, 4-(benzyl)phenyl, 3-(benzyloxy)phenyl, 4-(benzyloxy)phenyl, 4-(benzyloxy)-3-chlorophenyl, 3-(hydroxymethyl)phenyl, 4-biphenylyl, 3-phenoxyphenyl, 4-phenoxyphenyl, 3-chloro-4-phenoxyphenyl, 3-cyanophenyl, 3-trifluoromethoxyphenyl, 3-trifluoromethylphenyl, 3,4-difluorophenyl, 3-nitrophenyl, 3-ethynylphenyl, 4-amino-3-nitrophenyl, 4-chloro-3-nitrophenyl, 3-chloro-4-cyanophenyl or 4-chloro-3-cyanophenyl group or $R_a$ and $R_b$ denote, together with the nitrogen atom located between them, a 1-indolinyl or 1,2,3,4-tetrahydroquinolin-1-yl group and $R_c$ denotes a 3-tetrahydrofuranyloxy or 4-tetrahydropyranyloxy group, a 1-pyrrolidinyl group which is substituted in position 3 by an amino, methylamino or ethylamino group, a 1-pyrrolidinyl group which is substituted in position 4 by a 4-hydroxyphenyl group and additionally in position 2 by a methyl group, a 1-piperidinyl group which is substituted in position 2 by an aminomethyl, (1-pyrrolidinyl)methyl or dimethylaminomethyl group, a 1-piperidinyl group which is substituted in position 3 by an amino, aminomethyl, aminocarbonyl, aminocarbonylmethyl, acetylaminomethyl or methylsulphonylaminomethyl group, a 1-piperidinyl group which is optionally substituted in position 4 by an amino, hydroxyl, formylamino, methoxy, methylamino, ethylamino, morpholinocarbonylamino, methoxycarbonylamino, acetylamino, aminomethyl, methylaminomethyl, ethylaminomethyl, 2-carboxyethyl, 2-methoxycarbonylethyl, 2-(morpholinocarbonyl)ethyl, 2-aminoethyl, 2-aminocarbonylethyl, 2-methylaminocarbonylethyl, 2-dimethylaminocarbonylethyl, 2-(pyrrolidinocarbonyl)ethyl, carboxymethyloxy, methoxycarbonylmethyloxy, aminocarbonylmethyloxy, methylatninombonylmethyloxy, dimethylaminocarbonylmethyloxy, morpholinocarbonylmethyloxy, (1-pyrrolidinyl)carbonylmethyloxy, morpholino, 1-pyrrolidinyl, 1-piperldinyl, 4-piperidinyl, 1-methyl-4-piperidinyl, 1-piperazinyl, 4-methyl-1-piperazinyl, 4-dimethylamino-1-piperidinyl, 4-amino-1-piperidinyl, 2-oxo-1-pyrrolidinyl, 4-hydroxy-1-piperidinyl, 4-methylarnino-1-piperidinyl, 3-oxo-1-piperazinyl, 4-methyl-3-oxo-1-piperazinyl, N-acetyl-N-methylamino, N-methyl-N-methylsulphonylamino, (1-piperidinyl)methyl, (1-piperazinyl)methyl, (4-methyl-1-piperazinyl)methyl, morpholinomethyl, (1-pyrrolidinyl)methyl, dimethylaminomethyl, acetylaminomethyl, methylsulphonylaminomethyl, cyanomethyl, (1-piperazinyl)carbonyl, (4-methyl-1-piperazinyl)carbonyl, 2-oxo-1-imidazolidinyl or 3-methyl-2-oxo-1-imidazolidinyl group, a 1-piperidinyl group which is substituted by a methyl group and additionally in position 4 by an amino group, a 1-azacycloheptyl or 4-amino-1-azacycloheptyl group, a morpholino or 2,6-dimethylmorpholino group, a 1-piperazinyl group which is substituted in position 4 by a 2-aminoethyl, 2-methoxyphenyl, 3-methoxyphenyl, 4-methoxyphenyl or morpholinocarbonyl group, a 1-homopiperazinyl or 4-methyl-1-homopiperazinyl group, an 8-azabicyclo[3.2.1]-8-octyl group which is substituted in position 3 by an amino, methylamino, dimethylamino or acetylamino group or an $(R_4NR_5)$ group in which
$R_4$ denotes a hydrogen atom, a methyl or ethyl group,
$R_5$ denotes a hydrogen atom,
an isopropyl or tert-butyl group, a methyl group which is substituted by a 2-piperidinyl, 3-piperidinyl, 4-piperidinyl, 1-methyl-4-piperidinyl, 1-tert-butyloxycarbonyl-4-piperidinyl, 1-acetyl-4-piperidinyl, 1-(morpholinocarbonyl)-4-piperidinyl, 1-ethyl-2-pyffolidinyl, 1-ethyl-3-pyrrolidinyl, 3-aminomethylcyclopentyl, 3-tetrahydrofuryl, 4-quinuclidinyl, 1-piperazinylcarbonyl, 4-methyl-1-piperazinylearbonyl or 4-acetyl-1-piperazinylcarbonyl group, an ethyl group which is substituted in position 1 by a carboxyl, methoxycarbonyl, aminocarbonyl, methylaminocarbonyl, dimethylaminocarbonyl, 1-pyrrolidinylearbonyl, morpholinocarbonyl, 1-piperazinylcarbonyl, 4-methyl-1-piperazinylcarbonyl, 4-acetyl-1-piperazinylcarbonyl group or in position 2 by a hydroxyl, amino, cyano, 4-piperidinyl, 1-acetyl-4-piperidinyl, 1-methoxycarbonyl-4-piperidinyl, 1-methyl-2-pyrrolidinyl, 1-piperazinyl, 3-oxo-1-piperazinyl, 4-methyl-3-oxo-1-piperazinyl, 4-tert-butyloxycarbonyl-1-piperazinyl, 4-acetyl-1-piperazinyl, 4-(morpholinocarbonyl)-1-piperazinyl, 2-oxo-1-imidazolidinyl, 3-methyl-2-oxo-1-imidazolidinyl or 4-aminocyclohexyl group, a 2,2-dimethoxyethyl group, a 1-propyl group which is substituted in position 2 by an amino group and optionally additionally in position 2 by a methyl group, a 1-propyl group which is substituted in position 3 by an amino, morpholmo, acetylamino, methylsulphonylamino, methoxycarbonylamino or morpholinocarbonylamino group, a 2-propyl group which is substituted in position 1 by an amino, phenoxy, 4-aminophenyl, 1-piperidinyl or diethylamino group, a 2-propyl group which is substituted in position 1 by an amino group and additionally in position 2 by a methyl group, a 2-propyl group which is substituted in position 2 by a (1-piperazinyl)carbonyl, (4-methyl-1-piperazinyl) carbonyl or (4-acetyl-1-piperazinyl)carbonyl group, a 4-aminobutyl or a 5-aminopentyl group, a phenyl group which is substituted in position 4 by an acetylamino, dimethylaminocarbonyl, dimethylaminocarbonylarnino, ethylaminocarbonylarnino or N-(dimethylaminocarbonyl)-N-methylamino group, a cyclohexyl group which is substituted in position 4 by a hydroxyl, amino, methylamino, ethylamino, dimethylamino, methoxycarbonylamino, N-acetyl-N-methylamino, dimethylaminocarbonylamino, ethylaminocarbonylamino, benzoylamino, phenylsulphonylamino, phenylacetylamino, 2-phenylpropionylamino, morpholino, 1-pyrrolidinyl, 1-piperidinyl, 4-amino-1-piperidinyl, 4-dimethylamino-1-piperidinyl, 1-piperazinyl, 1-methyl-4-piperazinyl, 3-oxo-1-piperazinyl, 4-methyl-3-oxo-1-piperazinyl, 4-acetyl-1-piperazinyl, cyano, carboxyl, morpholinocarbonyl, (1-pyrrolidinyl)carbonyl, methoxycarbonyl, (4-methyl-1-piperazinyl)carbonyl, (1-piperazinyl) carbonyl, (2,6-dimethylmorpholino)carbonyl, thiomorpholinocarbonyl, thiomorpholinocarbonyl S-oxide, thiomorpholinocarbonyl S,S-dioxide, (4-acetyl-1-piperazinyl)carbonyl, aminomethyl, methylaminomethyl, ethylaminomethyl, dimethylaminomethyl, 1-piperidinylmethyl, 1-pyrrolidinylmethyl, morpholinomethyl, 1-piperazinylethyl, 4-methyl-1-piperazinylmethyl, 2-aminoethyl, 2-(morpholinocarbonyl)ethyl or 2-(1-pyrrolidinylcarbonyl)ethyl group, a 3-aminocyclohexyl or 3-dimethylaminocyclohexyl group, a 4-oxocyclohexyl group, a cyclohexylmethyl group which is substituted in the cyclohexyl moiety in position 4 by an amino, aminomethyl or benzyloxycarbonylamino group or in position 3 by an aminomethyl group, a 3-piperidinyl group which is optionally substituted in position 1 by a methyl or ethyl group, a 4-piperidinyl group which is optionally substituted in position 1 by a formyl, cyano, methyl, tert-butyloxycarbonyl, methoxycarbonyl, 2-aminoethyl, morpholinocarbonyl or (N,N-dimethylamino) carbonyl group, a cyclopentyl group which is substituted in position 1 by a hydroxymethyl or in position 3 by an amino, carboxyl, methoxycarbonyl or morpholinocarbonyl group, a 4-aminobenzyl group, a 4-tetrahydropyranyl, 4-tetrahydrothiopyranyl S-oxide or 4-tetrahydrothiopyranyl S,S-dioxide group, a 3-quinuclidinyl, 1-benzyl-4-(azacycloheptyl), 1-tert-butyloxycarbonyl-4-(azacycloheptyl), 4-(azacycloheptyl) or 1-(morpholinocarbonyl)-3-pyrrolidinyl group, with the proviso that the compounds
  4-[(4-amino-3,5-dibromophenyl)amino]-6-[(trans-4-hydroxycyclohexyl)amino]pyrimido[5,4-d]pyrimidine,
  4-[(3-chloro-4-fluorophenyl)amino]-6-[4-amino-1-piperidinyl]-pyrimido[5,4-d]pyrimidine,
  4-[(3-chloro-4-fluorophenyl)amino]-6-[3-amino-1-pyrrolidinyl]pyrimido[5,4-d]pyrimidine,
  4-[(3-chloro-4-fluorophenyl)amino]-6-[4-(2-aminoethyl)-1-piperazinyl]pyrimido[5,4-d]pyrimidine,
  4-[(3-chloro-4-fluorophenyl)amino]-6-[3-amino-1-piperidinyl]pyrimido [5,4-d]pyrimidine
  4-[(3-chloro-4-fluorophenyl)amino]-6-[3-piperidinylamino]pyrimido[5,4-d]pyrimidine,
  4-[(3-chloro-4-fluorophenyl)amino]-6-[1-methyl-3-piperidinylamino]pyrimido[5,4-d]pyrimidine, 4-[(3-chloro-4-fluorophenyl)amino]-6-[4-(N-acetyl-N-methylamino)cyclohexylamino]pyrimido[5,4-d]pyrimidine, 4-[(3-chloro-4-fluorophenyl)amino]-6-[4-(1-pyrrolidinyl)cyclohexylamino]pyrimido[5,4-d]pyrimidine, 4-[(3-chloro-4-fluorophenyl)amino]-6-[4-(morpholino)cyclohexylarnino]pyrimido[5,4-d]pyrimidine, 4-[(3-chloro-4-fluorophenyl)amino]-6-[trans-4-(2-(morpholinocarbonyl)ethyl)cyclohexylamino]pyrimido[5,4-d]pyrimidine, 4-[(4-amino-3-nitrophenyl)amino]-6-[(trans-4-hydroxycyclohexyl)amino]pyrimido[5,4-d]pyrimidine, 4-[(4-chloro-3-nitrophenyl)amino]-6-[(trans-4-hydroxycyclohexyl)amino]pyrimido[5,4-d]pyrimidine, 4-[(4-amino-3,5-dichlorophenyl)amino]-6-[(trans-4-hydroxycyclohexyl)amino]pyrimido[5,4-d]pyrimidine, 4-[(3-chloro-4-fluorophenyl)amino]-6-[1-(hydroxymethyl)cyclopentylamino]pyrimido[5,4-d]pyrimidine, 4-[(3-chloro-4-fluorophenyl)amino]-6-[N-methyl-N-(2-hydroxyethyl)amino]pyrimido[5,4-d]pyrimidine, 4-[(3-chloro-4-fluorophenyl)amino]-6-[3-(methoxycarbonylamino)-1-propylamino]pyrimido[5,4-d]pyrimidine, 4-[(3-chloro-4-fluorophenyl)amino]-6-[3-(morpholino)-1-propylamino]pyrimido[5,4-d]pyrimidine, 4-[(3-chloro-4-fluorophenyl)amino]-6-[2-(1-piperazinyl)-1-ethylamino]pynmido[5,4-d]pyrimidine, 4-[(3-chloro-4-fluorophenyl)amino]-6-[2-(1-acetyl-4-piperazinyl)ethylamino]pyrimido[5,4-d]pyrimidine, 4-[(4-amino-3-nitrophenyl)amino]-6-(morpholino)pyrimido[5,4-d]pyrimidine, 4-[(3-chloro-4-fluorophenyl)amino]-6-(4-tetrahydropyranyloxy)pyrimido[5,4-d]pyrimidine, 4-[(3-chloro-4-fluorophenyl)amino]-6-(3-tetrahydrofuranyloxy)pyrimido[5,4-d]pyrimidine and the compounds in which the $R_aNR_b$ group represents a 3-chlorophenylamino, (3-chloro-4-fluorophenyl)amino, (3-nitrophenyl)amino or (3-ethynylphenyl)ainino group when $R_c$ simultaneously represents a 4-tetrahydropyranylamino, tetrahydrofurftirylamino, 4-oxocyclohexylamino, morpholino, 4-piperidinylamino, isopropylamino, 1-methyl-4-piperidinylamino, tert-butylamino, N-(4-hydroxycyclohexyl)-N-methylamino, 4-hydroxycyclohexylarnino, 4-aminocyclohexylamino, 4-dimethylaminocyclohexylamino, trans-4-carboxycyclohexylamino, trans-4-(1-pyrrolidinyl)carbonylcyclohexylamino or trans-4-morpholinocarbonylcyclohexylamino group, are excepted, or a tautomer or pharmaceutically acceptable salt thereof.

2. A compound of the formula I, in accordance with claim 1, in which $R_c$ denotes a 1-pyrrolidinyl group which is substituted in position 4 by a 4-hydroxyphenyl group and additionally in position 2 by a methyl group, a 1-piperidinyl group which is optionally substituted in position 4 by an amino, methylarnino, hydroxyl, formylamino, methoxycarbonylamino, N-methyl-N-methylsulphonylamino, aminomethyl, morpholino, 1-pyrrolidinyl, 1-piperazinyl, 1-methyl-4-piperazinyl, (1-methyl-4-piperazinyl)methyl, 4-dimethylamino-1-piperidinyl, 4-piperidinyl or 1-methyl-4-piperidinyl group, a 4-amino-3-methyl-1-piperidinyl group, a 4-amino-4-methyl-1-piperidinyl group, a 1-piperidinyl group which is substituted in position 3 by an arninomethyl, aminocarbonyl or aminocarbonylmethyl group, a 1-azacycloheptyl or 4-amino-1-azacycloheptyl group, a morpholino group, a 1-piperazinyl group which is substituted in position 4 by a 2-methoxyphenyl, 3-methoxyphenyl or 4-methoxyphenyt group, a 1-homopiperazinyl or 4-methyl-1-homopiperazinyl group, an 8-azabicyclo[3.2.1]-8-octyl group which is substituted in position 3 by an amino or acetylamino group or an $(R_4NR_5)$ group in which $R_4$ represents a hydrogen atom, a methyl or ethyl group, $R_5$ represents a hydrogen atom, a methyl group which is substituted by a 3-tetrahydrofuryl, 4-piperidinyl, 1-methyl-4-piperidinyl, 1-tert-butyloxycarbonyl-4-piperidinyl or 4-quinuclidinyl group, an ethyl group which is substituted in position 2 by hydroxyl, amino, 4-tert-butyloxycarbonyl-1-piperazinyl or 4-(morpholinocarbonyl)-1-piperazinyl group, a 2,2-dimethoxyethyl group, a 1-propyl group which is substituted in position 2 by an amino group and optionally additionally in position 2 by a methyl group, a 1-propyl group which is substituted in position 3 by an amino group, a 2-propyl group which is substituted in position 1 by a phenoxy, 4-aminophenyl, 1-piperidinyl or diethylamino group, a 2-propyl group which is substituted in position 1 by an amino group and additionally in position 2 by a methyl group, a 4-aminobutyl or a 5-aminopentyl group, a cyclohexyl group which is substituted in position 4 by a hydroxyl, dimethylamino, 1-methyl-4-piperazinyl, 1-piperazinylcarbonyl, 1-methyl-4-piperazinylcarbonyl, 4-dimethylamino-1-piperidinyl, carboxyl, morpholinocarbonyl, (1-pyrrolidinyl)carbonyl, methoxycarbonyl, aminomethyl, methylamino, methoxycarbonylamino, 2-(morpholinocarbonyl)ethyl or 2-(1-pyrrolidinylcarbonyl)ethyl group, a cyclohexylmethyl group which is substituted in the cyclohexyl moiety in position 4 by an amino, aminomethyl or benzyloxycarbonylamino group or in position 3 by an arninometbyl group, a 1-methyl-3-piperidinyl group, a 4-piperidinyl group which is substituted in position 1 by a cyano, methyl, tert-butyloxycarbonyl, (N,N-dimethylamino)carbonyl or methoxycarbonyl group, a 4-aminobenzyl group, a 3-quinuclidinyl, 1-benzyl-4-(azacycloheptyl), 1-tert-butyloxycarbonyl-4-(azacycloheptyl) or 4-(azacycloheptyl) group, with the proviso that the compounds 4-[(4-amino-3,5-dibromophenyl)amino]-6-[(trans-4-hydroxycyclohexyl)amino]pyrimido[5,4-d]pyrimidine, 4-[(4-amino-3,5-dichlorophenyl)amino]-6-[(trans-4-hydroxycyclohexyl)amino]pyrimido[5,4-d]pyrimidine, 4-[(4-amino-3-mitrophenyl)amino]-6-[(trans-4-hydroxyxyxlohexyl)amino]pyrimido[5,4-d]pyrimidine, 4-[(4-amino-3-nitrophenyl)amino]-6-(morpholino)
pyrimido[5,4-d]pyrimidine, 4-[(4-chloro-3-nitrophenyl)amino]-6-[(trans-4-
hydroxycyclohexyl)amino]pyrimido[5,4-d]pyrimidine, and the compounds in which the $R_aNR_b$ group represents a (3-chlorophenyl)amino, (3-nitrophenyl)amino or (3-ethnylphenyl)amino group when $R_c$ simultaneously represents a tetrahydrofurfurylanmino, morpholino, 1-methyl-4-piperidinylarnino, N-(4-hydroxycyclohexyl)-N-methylamino, 4-hydroxycyclohexylamino, 4-dimethylaminocyclohexylamino, trans-4-carboxycyclohexylamino, trans-4-(1-pyrrolidinyl)carbonylcyclohexylamino or trans-4-morpholinocarbonylcyclohexylamino group, and the compounds in which the $R_aNR_b$ group represents a (3-chloro-4-fluorophenyl) amino group when $R_c$ simultaneously represents a 1-methyl-3-piperidinylamino, tetrahydrofinfurylamino, 3-(methoxycatbonylamino)-1-propylamino, N-methyl-N-(2-hydroxyethyl)amino, 4-amino-1-piperidinyl, morpholino, 1-methyl-4-piperidinylamino, 4-hydroxycyclohexylamino, 4-dimethylaminocyclohxylamino, N-(4-hydroxycyclohexyl)-N-methylamino, trans-4-carboxycyclohexylamino, trans-4-(2-(morpholinocarbonyl)ethyl)cyclohexylamino, trans-4-(1-pyrrolidinyl)carbonyleyclohexylamino or trans-4-morpholinocarbonylcyclohexylamino group, are excepted, or a tautomer or pharmaceutically acceptable salt thereof.

3. A compound selected from the group consisting of:

4-[(3-chloro-4-fluorophenyl)amino]-6-[4-methoxycarbonylamino-1-piperidinyl]pyrimido[5,4-d]pyrimidine, 4-[(3-chloro-4-fluorophenyl)amino]-6-[4-methoxycarbonylamino-1-piperidinyl]pyrimido[5,4-d]pyrimidine, 4-[(3-chloro-4-fluorophenyl)amino]-6-[(3-quinuclidinyl)-amino]pyrimido[5,4-d]pyrimidine, 4-[(3-chloro-4-fluorophenyl)amino]-6-[4-formylamino-1-piperidinyl]pyrimido[5,4-d]pyrimidine, 4-[(3-chloro-4-fluorophenyl)amino]-6-[4-(aminomethyl)-1-piperidinyl]pyrimido[5,4-d]pyrimidine, 4-[(3-chloro-4-fluorophenyl)amino]-6-[1-methoxycarbonyl-4-piperidinylamino]pyrimido[5,4-d]pyrimidine, 4-[(3-chloro-4-fluorophenyl)amino]-6-[3-aminopropyl-amino]pyrimido[5,4-d]pyrimidine, 4-[(3-chloro-4-fluorophenyl)amino]-6-[4-aminobenzyl-amino]pyrimido[5,4-d]pyrimidine, 4-[(4-amino-3,5-dichlorophenyl)amino]-6-[trans-4-(morpholino-carbonyl)cyclohexylamino]pyrimido[5,4-d]pyrimidine, 4-[(4-amino-3,5-dichlorophenyl)amino]-6-[trans-4-(pyrrolidino-carbonyl)cyclohexylamino]pyrimido[5,4-d]pyrimidine, 4-[(3-chloro-4-fluorophenyl)amino]-6-[4-(4-piperidinyl)-1-piperidinyl]pyrimido[5,4-d]pyrimidine, 4-[(3-chloro-4-fluorophenyl)amino]-6-[4-(aminomethyl)-cyclohexylmethylamino]pyrimido[5,4-d]pyrimidine, 4-[(3-chloro-4-fluorophenyl)amino]-6-[4-quinuclidinyl-methylamino]pyrimido[5,4-d]pyrimidine, 4-[(3-chloro-4-fluorophenyl)amino]-6-[2-amino-2-methyl-1-propylamino]pyrimido[5,4-d]pyrimidine, 4-[(3-chloro-4-fluorophenyl)amino]-6-[N-methyl-N-(1-methyl-4-piperidinyl)amino]pyrimido[5,4-d]pyrimidine, 4-[(3-chloro-4-fluorophenyl)amino]-6-[4-piperidinyl-methylamino]pyrimido[5,4-d]pyrimidine, 4-[(3-chloro-4-fluorophenyl)amino]-6-[4-(morpholino)-1-piperidinyl]pyrimido[5,4-d]pyrimidine, 4-[(3-chloro-4-fluorophenyl)amino]-6-[4-(1-pyrrolidinyl)-1-piperidinyl]pynmido[5,4-d]pyrimidine, 4-[(3-chloro-4-fluorophenyl)amino]-6-[3-(aminomethyl)-cyclohexylmethylamino]pyrimido[5,4-d]pyrimidine, 4-[(3-chloro-4-fluorophenyl)amino]-6-[4-(1-methyl-4-piperidinyl)-1-piperidinyl]pyrimido[5,4-d]pyrimidine, 4-[(3-chloro-4-fluorophenyl)amino]-6-[4-(1-methyl-4-piperazinyl)cyclohexylamino]pyrimido[5,4-d]pyrimidine, 4-[(3-chloro-4-fluorophenyl)amino]-6-[4-hydroxy-1-piperidinyl]pyrimido[5,4-d]pyrimidine, 4-[(3-chloro-4-fluorophenyl)amino]-6-[(1-cyano-4-piperidinyl)amino]pyrimido[5,4-d]pyrimidine, 4-[(3-chloro-4-fluorophenyl)amino]-6-[(1-methyl-4-piperidinyl)methylamino]pyrimido [5,4-d]pyrimidine, 4-[(3-chloro-4-fluorophenyl)amino]-6-[2-(4-(morpholino-carbonyl)-1-piperazinyl)ethylamino]pyrimido[5,4-d]pyrimidine, 4-[(3-chloro-4-fluorophenyl)amino]-6-[4-amino-1-azacyclo-heptyl]pyrimido[5,4-d]pyrimidine, 4-[(3-chloro-4-fluorophenyl)amino]-6-[4-(azacycloheptyl)-amino]pyrimido[5,4-d]pyrimidine, 4-[(3-chloro-4-fluorophenyl)arnino]-6-[trans-4-aminomethyl-cyclohexylamino]pyrimido[5,4-d]pyrimidine, 4-[(3-chloro-4-fluorophenyl)amino]-6-[3-aminomethyl-1-piperidinyl]pyrimido[5,4-d]pyrimidine, 4-[(3-chloro-4-fluorophenyl)amino]-6-[4-amino-4-methyl-1-piperidinyl]pyrimido[5,4-d]pyrimidine, 4-[(3-chloro-4-fluorophenyl)amino]-6-[endo-3-acetylamino-8-azabicyclo[3.2.1]-8-octyl]pyrimido[5,4-d]pyrimidine, 4-[(3-chloro-4-fluorophenyl)amino]-6-[4-(4-methyl-1-piperazinyl)methyl-1-piperidinyl]pyrimido[5,4-d]pyrimidine 4-[(4-benzyloxyphenyl)amino]-6-[trans-4-dimethylamino-cyclohexylamino]pyrimido[5,4-d]pyrimidine, (3'S)-4-[3-chlorophenylamino]-6-[(3'-quinuclidinyl)-amino]pyrimido[5,4-d]pyrimidine, 4-[(3-chloro-4-fluorophenyl)arnino]-6-[1-dimethylaminocarbonyl-4-piperidinylamino]pyrimido[5,4-d]pyrimidine, (3'S)-4-[(3-chloro-4-fluorophenyl)amino]-6-[(3'-quinuelidinyl)-amino]pyrimido[5,4-d]pyrimidine, and (3'R)-4-[(3-chloro-4-fluorophenyl)amino]-6-[(3'-quinuclidinyl)-amino]pynmido[5,4-d]pyrimidine, or a pharmaceutically acceptable salt thereof.

4. 4-[(3-Chloro-4-fluorophenyl)amino]-6-[2-(1-piperazinyl)ethylamino]pyrimido[5,4-d]pyrimidine or a pharmaceutically acceptable salt thereof.

5. 4-[(3-Chloro-4-fluorophenyl)amino]-6-[4-(azacycloheptyl)amino]pyrimido[5,4-d]pyrimidine or a pharmaceutically acceptable salt thereof.

6. A pharmaceutical composition comprising a compound in accordance with claim 1, 2, 3, 4, or 5, and a pharmaceutically acceptable carrier.

* * * * *